(12) United States Patent
Taki

(10) Patent No.: US 12,161,495 B2
(45) Date of Patent: Dec. 10, 2024

(54) ESTIMATION DEVICE, ESTIMATION METHOD, AND ESTIMATION PROGRAM

(71) Applicant: FUJIFILM CORPORATION, Tokyo (JP)

(72) Inventor: Tomoko Taki, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 353 days.

(21) Appl. No.: 17/591,614

(22) Filed: Feb. 3, 2022

(65) Prior Publication Data

US 2022/0287663 A1    Sep. 15, 2022

(30) Foreign Application Priority Data

Mar. 11, 2021    (JP) .................................. 2021-039485

(51) Int. Cl.
*A61B 6/00*        (2006.01)
*A61B 6/50*        (2024.01)
(Continued)

(52) U.S. Cl.
CPC .............. *A61B 6/482* (2013.01); *A61B 6/483* (2013.01); *A61B 6/505* (2013.01); *G06N 3/08* (2013.01);
(Continued)

(58) Field of Classification Search
CPC ....... A61B 6/483; A61B 6/505; A61B 6/5217; G06N 3/08; G06N 3/0464; G06N 3/09;
(Continued)

(56) References Cited

U.S. PATENT DOCUMENTS 6,064,716 A        5/2000  Siffert et al.
2016/0015347 A1    1/2016  Bregman-Amitai et al.
(Continued)

FOREIGN PATENT DOCUMENTS

CN      112089429 A    12/2020
EP      3851048 A1      7/2021
(Continued)

OTHER PUBLICATIONS

Partial English language translation of the following: Notice dated Nov. 7, 2023 from the JPO in a Japanese patent application No. 2021-039485 corresponding to the instant patent application. This office action translation is submitted now in order to supplement the understanding of the cited references which are being disclosed in the instant Information Disclosure Statement.
(Continued)

*Primary Examiner* — Dhaval V Patel
(74) *Attorney, Agent, or Firm* — SOLARIS Intellectual Property Group, PLLC

(57) ABSTRACT

An estimation device includes at least one processor, in which the processor functions as a learned neural network that derives a result of estimation relating to a bone density of a bone part from a simple radiation image acquired by simply imaging a subject including the bone part. The learned neural network is learned by using, as teacher data, (i) two radiation images acquired by imaging the subject including the bone part with radiation having different energy distributions, (ii) the radiation image of the subject and a bone part image representing the bone part of the subject, or (iii) the radiation image of the subject and a bone density image representing the bone density of the bone part of the subject, and information relating to the bone density of the bone part of the subject.

17 Claims, 32 Drawing Sheets

(51) Int. Cl.
*G06N 3/08* (2023.01)
*G06T 7/00* (2017.01)

(52) U.S. Cl.
CPC .. *G06T 7/0012* (2013.01); *G06T 2207/10116* (2013.01); *G06T 2207/30008* (2013.01)

(58) Field of Classification Search
CPC ......... G06T 7/0012; G06T 2207/10116; G06T 2207/30008; G06T 2207/20081; G06T 2207/20084; G06T 7/0014; G06T 2207/20028
See application file for complete search history.

(56) References Cited

U.S. PATENT DOCUMENTS

| | | |
|---|---|---|
| 2016/0089094 A1 | 3/2016 | Kawamura et al. |
| 2019/0362492 A1* | 11/2019 | Kawamura ........... G06T 7/0016 |
| 2019/0374186 A1 | 12/2019 | Oda |
| 2020/0305829 A1 | 10/2020 | Takahashi |
| 2020/0305830 A1 | 10/2020 | Takahashi |
| 2021/0015421 A1 | 1/2021 | Cicero et al. |
| 2022/0091050 A1 | 3/2022 | Iwashita et al. |

FOREIGN PATENT DOCUMENTS

| | | | |
|---|---|---|---|
| JP | H05-161633 A | 6/1993 | |
| JP | 2000-232611 A | 8/2000 | |
| JP | 2008-125691 A | 6/2008 | |
| JP | 2016-67586 A | 5/2016 | |
| JP | 2019-202035 A | 11/2019 | |
| JP | 2019-209054 A | 12/2019 | |
| JP | 2020-162857 A | 10/2020 | |
| JP | 2020-162972 A | 10/2020 | |
| JP | 2020-203083 A | 12/2020 | |
| WO | WO-2019208037 A1 * | 10/2019 | ............. A61B 6/032 |
| WO | WO-2020054738 A1 * | 3/2020 | ............. A61B 6/505 |

OTHER PUBLICATIONS

English language translation of the following: Office action dated May 21, 2024 from the JPO in a Japanese patent application No. 2021-039485 corresponding to the instant patent application. This office action translation is submitted now in order to supplement the understanding of the cited reference which is being disclosed in the instant Information Disclosure Statement.

English language translation of the following: Office action dated Jul. 30, 2024 from the JPO in a Japanese patent application No. 2021-039485 corresponding to the instant patent application. This office action translation is submitted now in order to supplement the understanding of the cited reference which is being disclosed in the instant Information Disclosure Statement.

* cited by examiner

ESTIMATION DEVICE, ESTIMATION METHOD, AND ESTIMATION PROGRAM

CROSS REFERENCE TO RELATED APPLICATIONS

The present application claims priority under 35 U.S.C. § 119 to Japanese Patent Application No. 2021-039485, filed on Mar. 11, 2021. The above application is hereby expressly incorporated by reference, in its entirety, into the present application.

BACKGROUND

Technical Field

The present disclosure relates to an estimation device, an estimation method, and an estimation program.

Related Art

A dual x-ray absorptiometry (DXA) method is known as one of typical bone mineral quantification methods used for diagnosing a bone density in a bone disease, such as osteoporosis. The DXA method is a method for calculating bone mineral density from a pixel value of a radiation image obtained by performing imaging by the radiation of two types of energies by using radiation incident on and transmitted through a human body, which is attenuated by an attenuation coefficient $\mu$ (cm$^2$/g), density $\rho$ (g/cm$^3$) and a thickness t (cm), which depend on a substance (for example, a bone) that configures the human body.

In addition, various methods for evaluating the bone density using a radiation image acquired by imaging a subject have been proposed. For example, U.S. Pat. No. 6,064,716A and WO2020/054738A propose a method for estimating information relating to the bone density from an image in which the bone appears by using a learned neural network constructed by learning a neural network. In the method disclosed in U.S. Pat. No. 6,064,716A, the neural network is learned by using the image in which the bone appears acquired by simple imaging and the bone density as teacher data. In addition, in the method disclosed in U.S. Pat. No. 6,064,716A, the neural network is learned by using the image in which the bone appears acquired by the simple imaging, the bone density, and the information relating to the bone density (for example, age, gender, weight, drinking habit, smoking habit, fracture history, body fat percentage, and subcutaneous fat percentage) as the teacher data.

Note that the simple imaging is an imaging method for acquiring one two-dimensional image, which is a transmission image of the subject, by emitting the radiation to the subject once. In the following description, the radiation image acquired by simple imaging will be referred to as a simple radiation image.

However, it is desired to estimate a bone density with higher accuracy.

SUMMARY OF THE INVENTION

The present disclosure has been made in view of the above circumstances, and is to enable estimation of the bone density with high accuracy.

An aspect of the present disclosure relates to an estimation device comprising at least one processor, in which the processor functions as a learned neural network that derives a result of estimation relating to a bone density of a bone part from a simple radiation image acquired by simply imaging a subject including the bone part, and the learned neural network is learned by using, as teacher data, (i) two radiation images acquired by imaging the subject including the bone part with radiation having different energy distributions, (ii) the radiation image of the subject and a bone part image representing the bone part of the subject, or (iii) the radiation image of the subject and a bone density image representing the bone density of the bone part of the subject, and information relating to the bone density of the bone part of the subject.

Note that in the estimation device according to the aspect of the present disclosure, the information relating to the bone density may be derived based on a body thickness distribution of the subject estimated based on at least one radiation image of the two radiation images acquired by imaging the subject including the bone part and a soft part with the radiation having different energy distributions, an imaging condition in a case in which the two radiation images are acquired, and a pixel value of a bone region in the bone part image obtained by extracting the bone part, the bone part image being derived by energy subtraction processing of performing weighting subtraction on the two radiation images.

In addition, in the estimation device according to the aspect of the present disclosure, the bone part image may be derived by recognizing the bone part and the soft part of the subject by using at least one radiation image of the two radiation images, deriving attenuation coefficients of the bone part and the soft part by using results of recognition of the bone part and the soft part and the two radiation images, and performing the energy subtraction processing by using the attenuation coefficients.

In addition, in the estimation device according to the aspect of the present disclosure, the bone part image may be derived by deriving a new weighting coefficient used for the weighting subtraction based on a pixel value of the bone part included in the bone part image, deriving a new bone part image by performing the weighting subtraction on the two radiation images by using the new weighting coefficient, and repeating derivation of a further new weighting coefficient based on the new bone part image and derivation of a further new bone part image based on the further new weighting coefficient.

In addition, in the estimation device according to the aspect of the present disclosure, the bone part image may be derived by deriving, for each of different energy distributions, a difference between a value of an attenuation coefficient of the soft part×a thickness of the soft part+an attenuation coefficient of the bone part×a thickness of the bone part, and each pixel value of the radiation image while changing, from initial values, the attenuation coefficient of the soft part for each of different energy distributions, the thickness of the soft part, the attenuation coefficient of the bone part for each of different energy distributions, and the thickness of the bone part, deriving the attenuation coefficient of the soft part and the attenuation coefficient of the bone part for each of different energy distributions, at which the difference is minimized or the difference is smaller than a predetermined threshold value, and performing the energy subtraction processing by using a weighting coefficient derived based on the attenuation coefficient of the soft part and the attenuation coefficient of the bone part.

In addition, in the estimation device according to the aspect of the present disclosure, the bone part image may be derived by deriving a composition ratio of a plurality of compositions included in the soft part of the subject, deriving, for each pixel of the two radiation images, an attenuation coefficient of the soft part for each of different energy distributions depending on the composition ratio, and performing the energy subtraction processing by using a weighting coefficient derived based on the derived attenuation coefficient of the soft part and a predetermined attenuation coefficient of the bone part.

In addition, in the estimation device according to the aspect of the present disclosure, the composition ratio may be obtained by deriving a body thickness of the subject as a first body thickness and a second body thickness for each pixel of each of the two radiation images and deriving the composition ratio for each pixel of the radiation image based on the first body thickness and the second body thickness.

In addition, in the estimation device according to the aspect of the present disclosure, the composition ratio may be obtained by deriving the first body thickness and the second body thickness based on an attenuation coefficient of each of the plurality of compositions for each of different energy distributions, deriving the first body thickness and the second body thickness while changing a thickness of the composition and the attenuation coefficient of each composition, and deriving the composition ratio based on the thickness of the composition in which a difference between the first body thickness and the second body thickness is equal to or smaller than a predetermined threshold value.

In addition, in the estimation device according to the aspect of the present disclosure, the bone part image may be derived by performing scattered ray removal processing of removing a scattered ray component of the radiation emitted to the subject, which is scattered by the subject, from the two radiation images, and performing the energy subtraction processing on the two radiation images from which the scattered ray component is removed.

In addition, in the estimation device according to the aspect of the present disclosure, the scattered ray removal processing may be performed by acquiring a radiation characteristic of an object interposed between the subject and a radiation detector that detects the radiation image depending on the body thickness distribution, deriving a primary ray distribution and a scattered ray distribution of the radiation included in each of the two radiation images by using the imaging condition, the body thickness distribution, and the radiation characteristic of the object, deriving an error between a sum of the primary ray distribution and the scattered ray distribution of each of the two radiation images and a pixel value at each position of the two radiation images, updating the body thickness distribution such that the error is smaller than a predetermined threshold value, repeating derivation of the radiation characteristic based on the updated body thickness distribution and derivation of the primary ray distribution and the scattered ray distribution included in each of the two radiation images, and subtracting the scattered ray distribution in a case in which the error is smaller than the predetermined threshold value from each of the two radiation images.

In addition, in the estimation device according to the aspect of the present disclosure, the scattered ray removal processing may be performed by deriving a first primary ray distribution and a scattered ray distribution of the radiation transmitted through the subject by using the two radiation images, deriving a second primary ray distribution and a scattered ray distribution of the radiation transmitted through an object interposed between the subject and a radiation detector that detects the radiation image by using the first primary ray distribution, the scattered ray distribution, and a radiation characteristic of the object, and deriving the radiation images after transmission through the subject and the object by using the second primary ray distribution and the scattered ray distribution.

In addition, in the estimation device according to the aspect of the present disclosure, the scattered ray removal processing may be performed by deriving a region detection image by detecting a subject region in which the radiation is transmitted through the subject and reaches a radiation detector and a direct radiation region in which the radiation directly reaches the radiation detector without being transmitted through the subject in the two radiation images, deriving a scattered ray image relating to the scattered ray component based on the region detection image and scattered ray spread information relating to spread of a scattered ray, and subtracting the scattered ray image from the two radiation images.

In addition, in the estimation device according to the aspect of the present disclosure, the bone part image may be obtained by deriving a processing content of first granulation suppression processing on a first radiation image having higher S/N among the two radiation images, deriving a processing content of second granulation suppression processing on a second radiation image having lower S/N based on the processing content of the first granulation suppression processing, performing granulation suppression processing on the first radiation image based on the processing content of the first granulation suppression processing, performing granulation suppression processing on the second radiation image based on the processing content of the second granulation suppression processing, and deriving the bone part image by using the two radiation images subjected to the granulation suppression processing.

In this case, the processing content of the first granulation suppression processing may be derived based on a physical quantity map of the subject derived based on at least one of the first radiation image or the second radiation image.

In addition, in the estimation device according to the aspect of the present disclosure, the information relating to the bone density may include at least one of the bone density, an evaluation value of a fracture risk of the subject, or information representing a recovery state of the bone part after treatment.

Another aspect of the present disclosure relates to an estimation method comprising using a learned neural network that derives a result of estimation relating to a bone density of a bone part from a simple radiation image acquired by simply imaging a subject including the bone part to derive the result of estimation relating to the bone density from the simple radiation image, in which the learned neural network is learned by using, as teacher data, (i) two radiation images acquired by imaging the subject including the bone part with radiation having different energy distributions, (ii) the radiation image of the subject and a bone part image representing the bone part of the subject, or (iii) the radiation image of the subject and a bone density image representing the bone density of the bone part of the subject, and information relating to the bone density of the bone part of the subject.

Note that the estimation method according to the present disclosure may be provided as a program causing a computer to execute.

According to the present disclosure, it is possible to estimate the bone density with high accuracy.

DETAILED DESCRIPTION

Figure 1:
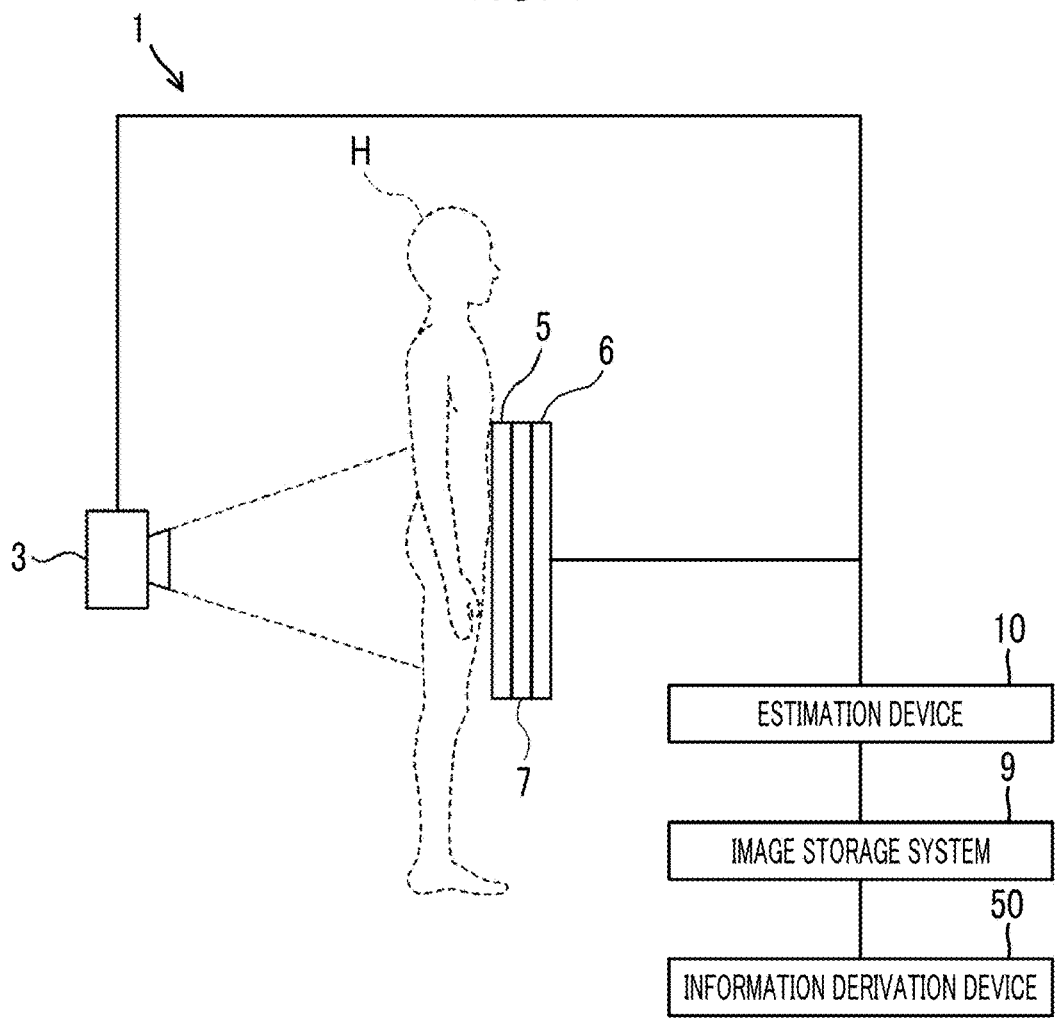
FIG. 1 is a schematic block diagram showing a configuration of a radiography system to which an estimation device according to a first embodiment of the present disclosure is applied.

Hereinafter, embodiments of the present disclosure will be described with reference to the drawings. FIG. 1 is a schematic block diagram showing a configuration of a radiography system to which an estimation device according to a first embodiment of the present disclosure is applied. As shown in FIG. 1, the radiography system according to the first embodiment comprises an imaging apparatus 1, an image storage system 9, an estimation device 10 according to the first embodiment, and an information derivation device 50. The imaging apparatus 1, the estimation device 10, and the information derivation device 50 are connected to the image storage system 9 via a network (not shown).

The imaging apparatus 1 is an imaging apparatus that can perform energy subtraction by a so-called one-shot method for converting radiation, such as X-rays, emitted from a radiation source 3 and transmitted through a subject H into energy and irradiating a first radiation detector 5 and a second radiation detector 6 with the converted radiation. At the time of imaging, as shown in FIG. 1, the first radiation detector 5, a radiation energy conversion filter 7 made of a copper plate or the like, and the second radiation detector 6 are disposed in order from a side closest to the radiation source 3, and the radiation source 3 is driven. Note that the first and second radiation detectors 5 and 6 are closely attached to the radiation energy conversion filter 7.

As a result, in the first radiation detector 5, a first radiation image G1 of the subject H by low-energy radiation including so-called soft rays is acquired. In addition, in the second radiation detector 6, a second radiation image G2 of the subject H by high-energy radiation from which the soft rays are removed is acquired. Therefore, the first radiation image G1 and the second radiation image G2 are acquired by imaging the subject H with the radiation having different energy distributions. The first and second radiation images G1 and G2 are input to the estimation device 10. Both the first radiation image G1 and the second radiation image G2 are front images including a periphery of a crotch of the subject H.

The first and second radiation detectors 5 and 6 can perform recording and reading-out of the radiation image repeatedly. A so-called direct-type radiation detector that directly receives emission of the radiation and generates an electric charge may be used, or a so-called indirect-type radiation detector that converts the radiation into visible light and then converts the visible light into an electric charge signal may be used. In addition, as a method for reading out a radiation image signal, it is desirable to use a so-called thin film transistor (TFT) readout method in which the radiation image signal is read out by turning a TFT switch on and off, or a so-called optical readout method in which the radiation image signal is read out by emission of read out light. However, other methods may also be used without being limited to these methods.

In addition, the imaging apparatus 1 can acquire a simple radiation image G0 which is a simple two-dimensional image of the subject H by performing a simple imaging of the subject H by using only the first radiation detector 5. The imaging for acquiring the first and second radiation images G1 and G2 is referred to as energy subtraction imaging in order to distinguish the imaging from simple imaging. In the present embodiment, the first and second radiation images G1 and G2 acquired by the energy subtraction imaging are used as learning data to be described below. In addition, the simple radiation image G0 acquired by the simple imaging is used for deriving a result of estimation relating to a bone density as described below.

The image storage system 9 is a system that stores image data of the radiation image acquired by the imaging apparatus 1. The image storage system 9 extracts an image corresponding to a request from the estimation device 10 from the stored radiation image and transmits the extracted image to a request source device. Specific examples of the image storage system 9 include picture archiving and communication systems (PACS). Note that in the present embodiment, the image storage system 9 stores a large amount of teacher data for learning the neural network described below.

Figure 2:
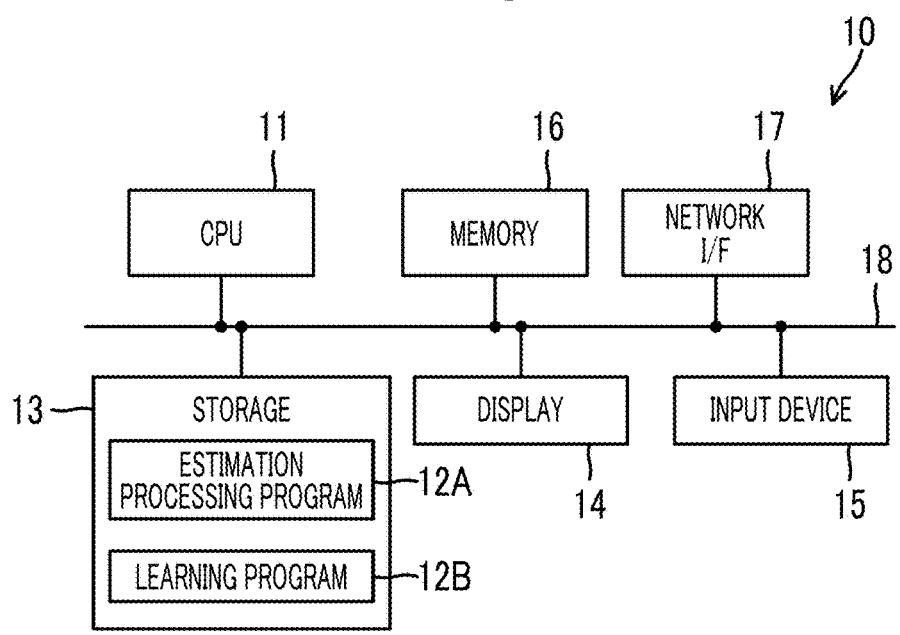
FIG. 2 is a diagram showing a schematic configuration of the estimation device according to the first embodiment.

Then, the estimation device according to the first embodiment will be described. First, a hardware configuration of the estimation device according to the first embodiment will be described with reference to FIG. 2. As shown in FIG. 2, the estimation device 10 is a computer, such as a workstation, a server computer, and a personal computer, and comprises a central processing unit (CPU) 11, a non-volatile storage 13, and a memory 16 as a transitory storage region. In addition, the estimation device 10 comprises a display 14, such as a liquid crystal display, an input device 15, such as a keyboard and a mouse, and a network interface (I/F) 17 connected to a network (not shown). The CPU 11, the storage 13, the display 14, the input device 15, the memory 16, and the network I/F 17 are connected to a bus 18. Note that the CPU 11 is an example of a processor according to the present disclosure.

The storage 13 is realized by a hard disk drive (HDD), a solid state drive (SSD), a flash memory, and the like. The storage 13 as a storage medium stores an estimation program 12A and a learning program 12B installed in the estimation device 10. The CPU 11 reads out the estimation program 12A and the learning program 12B from the storage 13, expands the estimation program 12A and the learning program 12B in the memory 16, and executes the expanded estimation program 12A and the expanded learning program 12B.

Note that the estimation program 12A and the learning program 12B are stored in a storage device of the server computer connected to the network or in a network storage in a state of being accessible from the outside, and are downloaded and installed in the computer that configures the estimation device 10 in response to the request. Alternatively, the estimation program 12A and the learning program 12B are distributed in a state of being recorded on a recording medium, such as a digital versatile disc (DVD) or a compact disc read only memory (CD-ROM), and are installed in the computer that configures the estimation device 10 from the recording medium.

Figure 3:
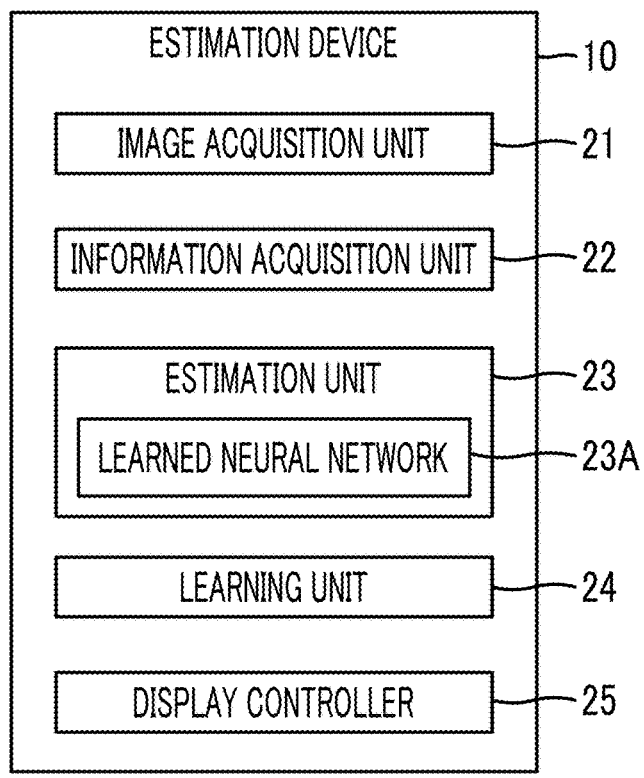
FIG. 3 is a diagram showing a functional configuration of an estimation device according to the first embodiment.

Then, a functional configuration of the estimation device according to the first embodiment will be described. FIG. 3 is a diagram showing the functional configuration of the estimation device according to the first embodiment. As shown in FIG. 3, the estimation device 10 comprises an image acquisition unit 21, an information acquisition unit 22, an estimation unit 23, a learning unit 24, and a display controller 25. Further, the CPU 11 functions as the image acquisition unit 21, the information acquisition unit 22, the estimation unit 23, and the display controller 25 by executing the estimation program 12A. In addition, the CPU 11 functions as the learning unit 24 by executing the learning program 12B.

The image acquisition unit 21 acquires, for example, the first radiation image G1 and the second radiation image G2 which are the front images of the periphery of the crotch of the subject H from the first and second radiation detectors 5 and 6 by causing the imaging apparatus 1 to perform the energy subtraction imaging of the subject H. In a case in which the first radiation image G1 and the second radiation image G2 are acquired, an imaging conditions, such as an imaging dose, a radiation quality, a tube voltage, a source image receptor distance (SID) which is a distance between the radiation source 3 and surfaces of the first and second radiation detectors 5 and 6, a source object distance (SOD) which is a distance between the radiation source 3 and a surface of the subject H, and the presence or absence of a scattered ray removal grid are set.

The SOD and the SID are used to calculate a body thickness distribution as described below. It is preferable that the SOD be acquired by, for example, a time of flight (TOF) camera. It is preferable that the SID be acquired by, for example, a potentiometer, an ultrasound range finder, a laser range finder, or the like.

The imaging conditions need only be set by input from the input device 15 by an operator. The set imaging conditions are stored in the storage 13. The first and second radiation images G1 and G2 acquired by the energy subtraction imaging and the imaging conditions are also transmitted to and stored in the image storage system 9. The first and second radiation images G1 and G2 are used for deriving the teacher data described below.

In addition, the image acquisition unit 21 acquires the simple radiation image G0 which is the front image of the vicinity of the crotch of the subject H by causing the imaging apparatus 1 to perform the simple imaging of the subject H by using only the first radiation detector 5.

Note that in the present embodiment, the first and second radiation images G1 and G2 and the simple radiation image G0 may be acquired by a program separate from the estimation program 12A and stored in the storage 13. In this case, the image acquisition unit 21 acquires the first and second radiation images G1 and G2 stored in the storage 13 by reading out the first and second radiation images G1 and G2 and the simple radiation image G0 from the storage 13 for processing.

The information acquisition unit 22 acquires the teacher data for learning a neural network, which will be described below, from the image storage system 9 via the network I/F 17.

The estimation unit 23 derives the result of estimation relating to the bone density of the bone part included in the subject H from the simple radiation image G0. In the present embodiment, the result of estimation of the bone density of a target bone in a bone region included in the simple radiation image G0 is derived as the result of estimation of the bone density. Therefore, the estimation unit 23 derives the result of estimation relating to the bone density by using a learned neural network 23A that outputs the bone density in a case in which the simple radiation image G0 is input.

The learning unit 24 constructs the learned neural network 23A by machine learning the neural network by using the teacher data. Examples of the neural network include a simple perceptron, a multi-layer perceptron, a deep neural network, a convolutional neural network, a deep belief network, a recurrent neural network, and a stochastic neural network. In the present embodiment, the convolutional neural network is used as the neural network.

Figure 4:
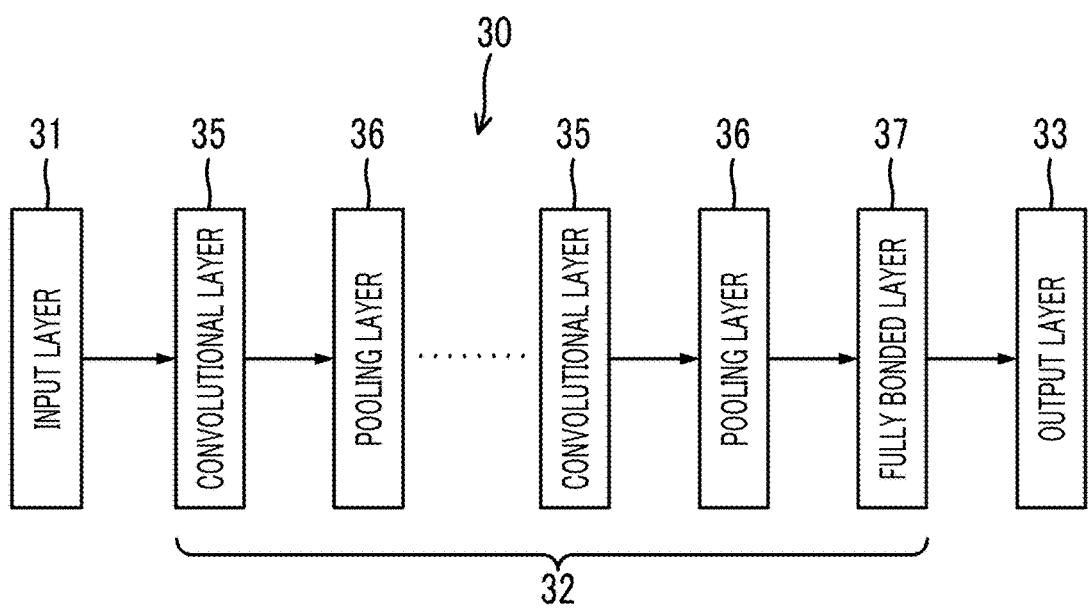
FIG. 4 is a diagram showing a schematic configuration of a neural network used in the present embodiment.

FIG. 4 is a diagram showing the neural network used in the present embodiment. As shown in FIG. 4, a neural network 30 comprises an input layer 31, an interlayer 32, and an output layer 33. The interlayer 32 comprises, for example, a plurality of convolutional layers 35, a plurality of pooling layers 36, and a fully bonded layer 37. In the neural network 30, the fully bonded layer 37 is present in front of the output layer 33. Further, in the neural network 30, the convolutional layer 35 and the pooling layer 36 are alternately disposed between the input layer 31 and the fully bonded layer 37.

Note that a configuration of the neural network 30 is not limited to the example of FIG. 4. For example, the neural network 30 may comprise one convolutional layer 35 and one pooling layer 36 between the input layer 31 and the fully bonded layer 37.

Figure 5:
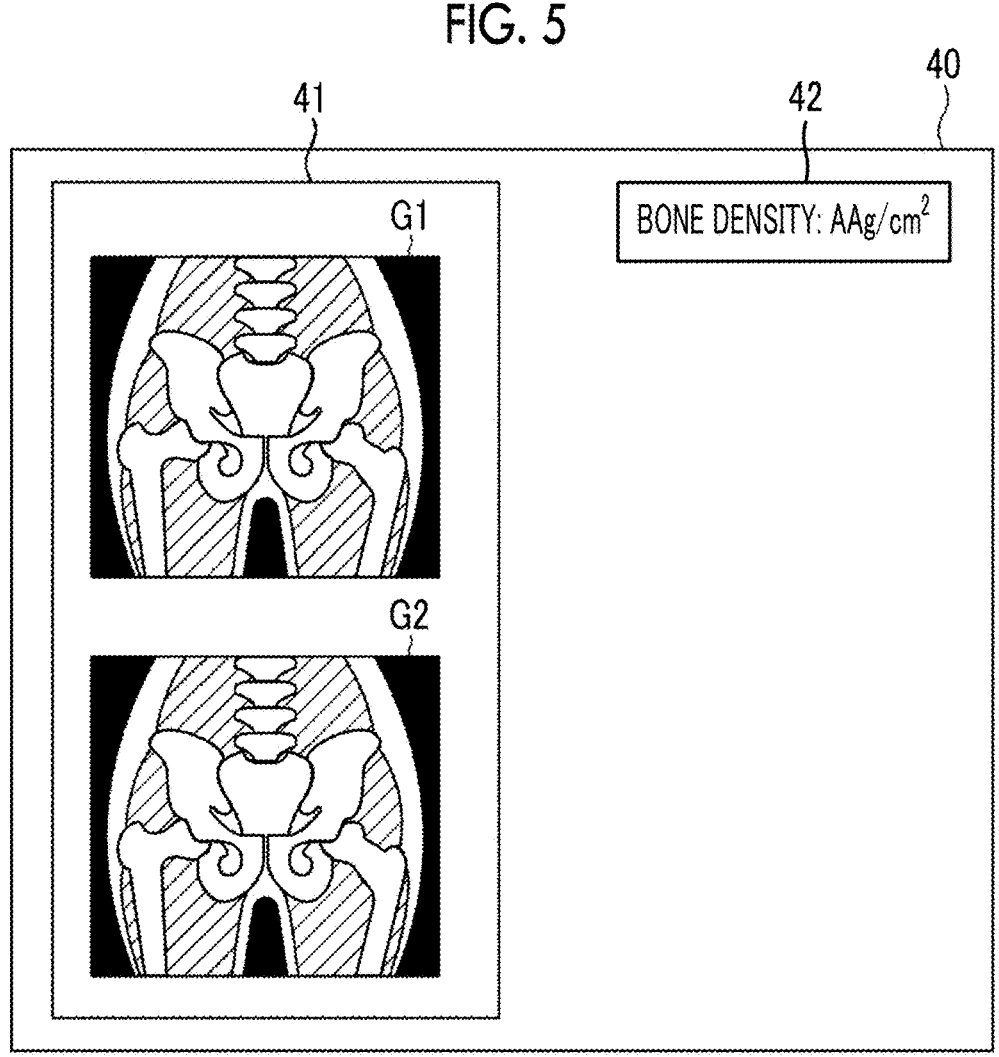
FIG. 5 is a diagram showing teacher data.

FIG. 5 is a diagram showing an example of the teacher data used for learning the neural network. As shown in FIG. 5, teacher data 40 consists of learning data 41 and correct answer data 42. In the present embodiment, the data input to the learned neural network 23A in order to obtain the result of estimation of the bone density is the simple radiation image G0, but the learning data 41 includes two radiation images of the first radiation image G1 and the second radiation image G2 acquired by the energy subtraction imaging.

The correct answer data 42 is the bone density of the target bone (that is, a femur) of the subject from which the learning data 41 is acquired. Note that in the present embodiment, since the bone density per unit area is estimated from the two-dimensional simple radiation image G0, the unit of the bone density is (g/cm$^2$). The bone density, which is the correct answer data 42, is derived by the information derivation device 50. In the present embodiment, for example, by using a method disclosed in JP2019-202035A, the bone density, which is the correct answer data 42, is derived. Note that the bone density, which is the correct answer data 42, is an example of information relating to the bone density of the bone part of the subject. Hereinafter, the information derivation device 50 will be described.

Figure 6:
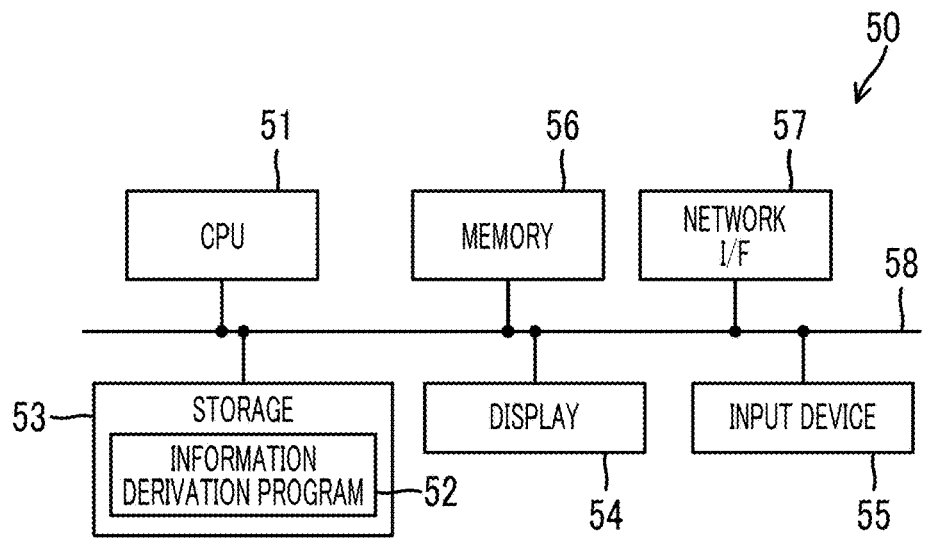
FIG. 6 is a diagram showing a schematic configuration of an information derivation device according to the first embodiment.

FIG. 6 is a schematic block diagram showing a configuration of the information derivation device according to the first embodiment. As shown in FIG. 6, the information derivation device 50 according to the first embodiment is a computer, such as a workstation, a server computer, and a personal computer, and includes a CPU 51, a non-volatile storage 53, and a memory 56 as a transitory storage region. In addition, the information derivation device 50 includes a display 54, such as a liquid crystal display, an input device 55 including a pointing device, such as a keyboard and a mouse, and a network I/F 57 connected to a network (not shown). The CPU 51, the storage 53, the display 54, the input device 55, the memory 56, and the network I/F 57 are connected to a bus 58.

Similar to the storage 13, the storage 53 is realized by the HDD, the SSD, the flash memory, and the like. An information derivation program 52 is stored in the storage 53 as the storage medium. The CPU 51 reads out the information derivation program 52 from the storage 53, expands the read out information derivation program 52 in the memory 56, and executes the expanded information derivation program 52.

Figure 7:
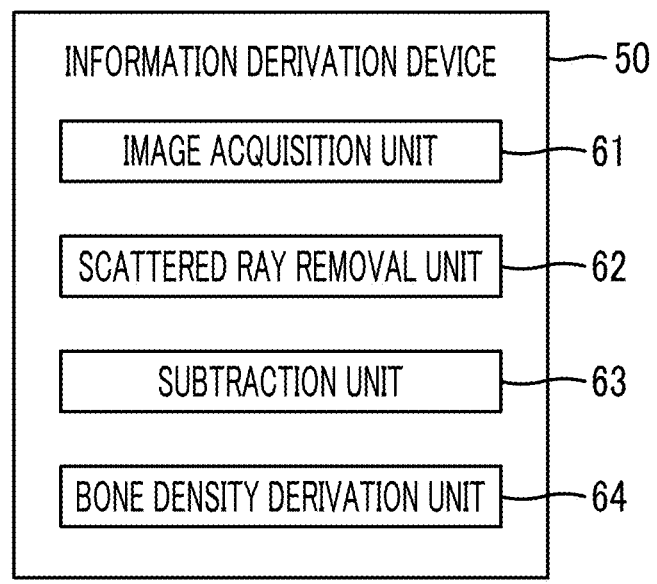
FIG. 7 is a diagram showing a functional configuration of the information derivation device according to the first embodiment.

Then, a functional configuration of the information derivation device according to the first embodiment will be described. FIG. 7 is a diagram showing the functional configuration of the information derivation device according to the first embodiment. As shown in FIG. 7, the information derivation device 50 according to the first embodiment comprises an image acquisition unit 61, a scattered ray removal unit 62, a subtraction unit 63, and a bone density derivation unit 64. Further, the CPU 51 executes the information derivation program 52, so that the CPU 51 functions as the image acquisition unit 61, the scattered ray removal unit 62, the subtraction unit 63, and the bone density derivation unit 64.

The image acquisition unit 61 acquires the first radiation image G1 and the second radiation image G2, which are the learning data 41, stored in the image storage system 9. Note that the image acquisition unit 61 may acquire the first radiation image G1 and the second radiation image G2 by causing the imaging apparatus 1 to image the subject H in the same manner as the image acquisition unit 21 of the estimation device 10.

The image acquisition unit 61 also acquires the imaging conditions in a case in which the first and second radiation images stored in the image storage system 9 are acquired. The imaging conditions include the imaging dose in a case in which the first radiation image G1 and the second radiation image G2 are acquired, the tube voltage, the SID, the SOD, the presence or absence of the scattered ray removal grid, and the like.

Here, each of the first radiation image G1 and the second radiation image G2 includes a scattered ray component based on the radiation scattered in the subject H in addition to a primary ray component of the radiation transmitted through the subject H. Therefore, the scattered ray removal unit 62 removes the scattered ray component from the first radiation image G1 and the second radiation image G2. For example, the scattered ray removal unit 62 may remove the scattered ray component from the first radiation image G1 and the second radiation image G2 by applying a method disclosed in JP2015-043959A. In a case in which a method disclosed in JP2015-043959A or the like is used, the derivation of the body thickness distribution of the subject H and the derivation of the scattered ray component for removing the scattered ray component are performed at the same time.

Hereinafter, the removal of the scattered ray component from the first radiation image G1 will be described, but the removal of the scattered ray component from the second radiation image G2 can also be performed in the same manner. First, the scattered ray removal unit 62 acquires a virtual model of the subject H having an initial body thickness distribution $T0(x,y)$. The virtual model is data virtually representing the subject H of which a body thickness in accordance with the initial body thickness distribution $T0(x,y)$ is associated with a coordinate position of each pixel of the first radiation image G1. Note that the virtual model of the subject H having the initial body thickness distribution $T0(x,y)$ may be stored in the storage 53 of the information derivation device 50 in advance. In addition, the scattered ray removal unit 62 may calculate a body thickness distribution $T(x,y)$ of the subject H based on the SID and the SOD included in the imaging conditions. In this case, the initial body thickness distribution $T0(x,y)$ can be obtained by subtracting the SOD from the SID.

Next, the scattered ray removal unit 62 generates, based on the virtual model, an image obtained by synthesizing an estimated primary ray image in which a primary ray image obtained by imaging the virtual model is estimated and an estimated scattered ray image in which a scattered ray image obtained by imaging the virtual model is estimated as an estimated image in which the first radiation image G1 obtained by imaging the subject H is estimated.

Next, the scattered ray removal unit 62 corrects the initial body thickness distribution $T0(x,y)$ of the virtual model such that a difference between the estimated image and the first radiation image G1 is small. The scattered ray removal unit 62 repeatedly performs the generation of the estimated image and the correction of the body thickness distribution until the difference between the estimated image and the first radiation image G1 satisfies a predetermined termination condition. The scattered ray removal unit 62 derives the body thickness distribution in a case in which the termination condition is satisfied as the body thickness distribution $T(x,y)$ of the subject H. In addition, the scattered ray removal unit 62 removes the scattered ray component included in the first radiation image G1 by subtracting the scattered ray component in a case in which the termination condition is satisfied from the first radiation image G1.

Figure 8:
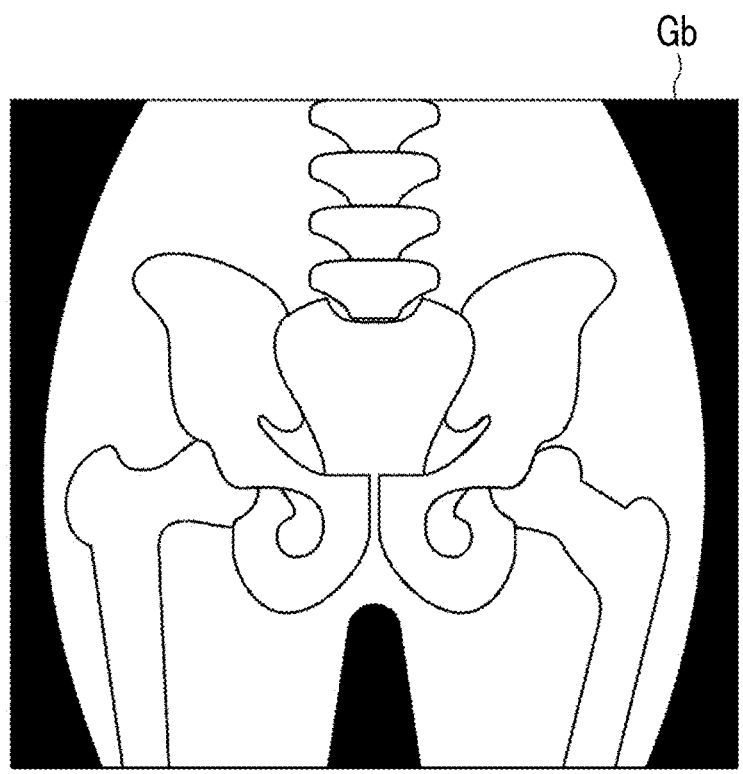
FIG. 8 is a diagram showing a bone part image.

The subtraction unit 63 derives a bone part image Gb obtained by extracting the bone part of the subject H from the first and second radiation images G1 and G2 by performing the energy subtraction processing. Note that in the first and second radiation images G1 and G2 in the subsequent processing, the scattered ray component is removed. In a case in which the bone part image Gb is derived, the subtraction unit 63 performs weighting subtraction between the corresponding pixels with respect to the first and second radiation images G1 and G2 as shown in Expression (1) to generate the bone part image Gb in which the bone part of the subject H included in each of the radiation images G1 and G2 is extracted, as shown in FIG. 8. In Expression (1), α is a weighting coefficient. Note that a pixel value of each pixel in a bone region in the bone part image Gb is a bone part pixel value.

$$Gb(x,y) = \alpha G2(x,y) - G1(x,y) \quad (1)$$

The bone density derivation unit 64 derives the bone density for each pixel of the bone part image Gb. In the present embodiment, the bone density derivation unit 64 derives a bone density B by converting each pixel value of the bone part image Gb into the pixel value of the bone part image acquired under standard imaging conditions. Specifically, the bone density derivation unit 64 derives the bone density by correcting each pixel value of the bone part image Gb by using a correction coefficient acquired from a look-up table described below.

Here, a contrast between the soft part and the bone part in the radiation image is lower as the tube voltage in the radiation source 3 is higher and the energy of the radiation emitted from the radiation source 3 is higher. In addition, in a procedure of the radiation transmitted through the subject H, a low-energy component of the radiation is absorbed by the subject H, and beam hardening occurs in which the radiation energy is increased. The increase in the radiation energy due to the beam hardening is larger as the body thickness of the subject H is larger.

Figure 9:
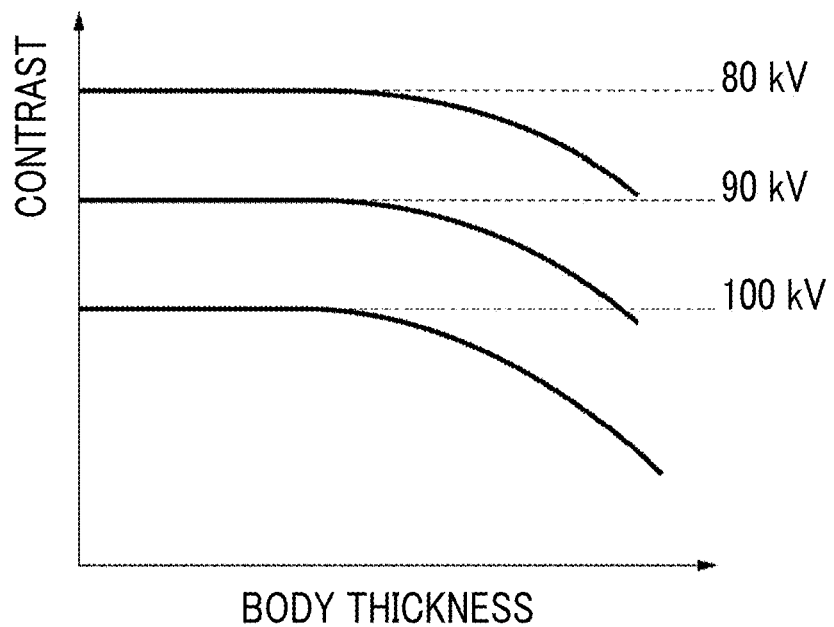
FIG. 9 is a diagram showing a relationship of a contrast between a bone part and a soft part with respect to a body thickness of a subject.

FIG. 9 is a diagram showing a relationship of the contrast between the bone part and the soft part with respect to the body thickness of the subject H. Note that FIG. 9 shows the relationship of the contrast between the bone part and the soft part with respect to the body thickness of the subject H at the three tube voltages of 80 kV, 90 kV, and 100 kV. As shown in FIG. 9, the contrast is lower as the tube voltage is higher. In addition, in a case in which the body thickness of the subject H exceeds a certain value, the contrast is lower as the body thickness is larger. Note that contrast between the bone part and the soft part is higher as the pixel value of the bone region in the bone part image Gb is larger. Therefore, the relationship shown in FIG. 9 shifts to a higher contrast side as the pixel value of the bone region in the bone part image Gb is increased.

In the first embodiment, the look-up table for acquiring the correction coefficient for correcting the difference in the contrast depending on the tube voltage at the time of imaging and the reduction in the contrast due to the influence of the beam hardening in the bone part image Gb is stored in the storage 53 of the information derivation device 50. The correction coefficient is the coefficient for correcting each pixel value of the bone part image Gb.

Figure 10:
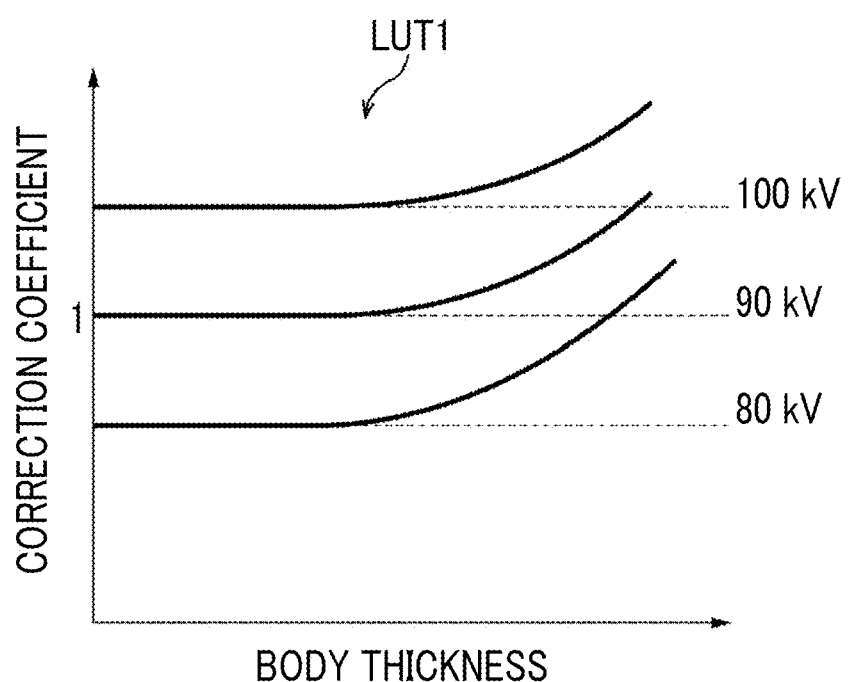
FIG. 10 is a diagram showing an example of a look-up table for acquiring a correction coefficient.

FIG. 10 is a diagram showing an example of the look-up table for acquiring the correction coefficient. In FIG. 10, a look-up table (hereinafter simply referred to as a table) LUT1 in which the standard imaging condition is set to the tube voltage of 90 kV is shown. As shown in FIG. 10, in the table LUT1, the correction coefficient is set to be larger as the tube voltage is higher and the body thickness of the subject H is larger. In the example shown in FIG. 10, since the standard imaging condition is the tube voltage of 90 kV, the correction coefficient is 1 in a case in which the tube voltage is 90 kV and the body thickness is 0. Note that although the table LUT1 is shown in two dimensions in FIG. 10, the correction coefficient differs depending on the pixel value of the bone region. Therefore, the table LUT1 is actually a three-dimensional table to which an axis representing the pixel value of the bone region is added.

The bone density derivation unit 64 extracts the body thickness distribution $T(x,y)$ of the subject H and a correction coefficient $C0(x,y)$ for each pixel depending on the imaging conditions including a set value of the tube voltage stored in the storage 13 from the table LUT1. Further, as shown in Expression (2), the bone density derivation unit 64 multiplies each pixel $(x,y)$ of the bone region in the bone part image Gb by the correction coefficient $C0(x,y)$ to derive the bone density $B(x,y)$ ($g/cm^2$) for each pixel of the bone part image Gb. The bone density $B(x,y)$ derived in this way is acquired by imaging the subject H by the tube voltage of 90 kV, which is the standard imaging condition, and shows the pixel value of the bone region included in the radiation image from which the influence of the beam hardening is removed. Therefore, a bone density image in which the derived bone density is used as the pixel value of each pixel is derived by the bone density derivation unit 64.

$$B(x,y)=C0(x,y)\times Gb(x,y) \qquad (2)$$

Moreover, in the present embodiment, the bone density derivation unit 64 derives a representative value of bone density B only for the target bone. For example, in a case in which the target bone is the femur, the bone density derivation unit 64 derives the representative value of the bone density B of the femur region by deriving the representative value of the bone density B of each pixel in the femur region in the bone part image Gb. An average value, a median value, a minimum value, a maximum value, and the like can be used as the representative value. In the present embodiment, the representative value of the bone density of the femur, which is the target bone, is used as the correct answer data 42.

The bone density, which is used as the correct answer data 42, is derived at the same time as the time when the learning data 41 is acquired, and is transmitted to the image storage system 9. In the image storage system 9, the learning data 41 and the correct answer data 42 are stored in association with each other as the teacher data 40. Note that in order to improve the robustness of the learning, the teacher data 40 including, as learning data 41, an image obtained by performing at least one of enlargement/reduction, contrast change, movement, in-plane rotation, inversion, or noise addition on the same image may be additionally created and stored.

Figure 11:
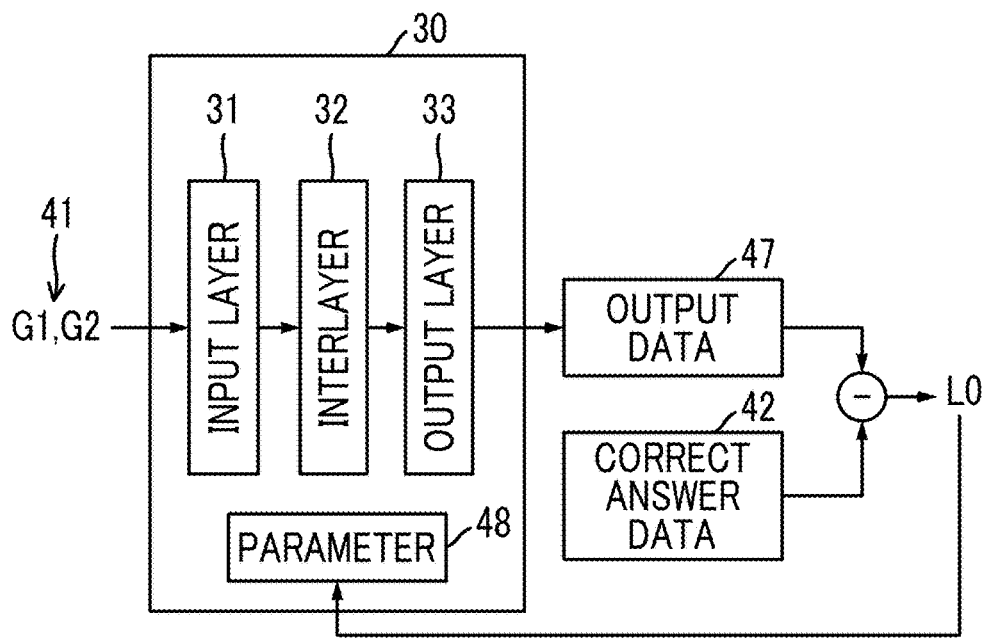
FIG. 11 is a diagram for describing learning of the neural network.

The description will be returned to the estimation device 10. The learning unit 24 learns the neural network by using a large amount of the teacher data 40. FIG. 11 is a diagram for describing learning of the neural network 30. In a case in which the neural network 30 is learned, the learning unit 24 inputs the learning data 41, that is, the first and second radiation images G1 and G2 to the input layer 31 of the neural network 30. Further, the learning unit 24 outputs the bone density of the target bone as output data 47 from the output layer 33 of the neural network 30. Further, the learning unit 24 derives a difference between the output data 47 and the correct answer data 42 as a loss L0.

The learning unit 24 learns the neural network 30 based on the loss L0. Specifically, the learning unit 24 adjusts a kernel coefficient in the convolutional layer 35, a weight of the bond between the layers, a weight of the bond in the fully bonded layer 37, and the like (hereinafter referred to as a parameter 48) such that the loss L0 is reduced. For example, an error backpropagation method can be used as a method for adjusting the parameter 48. The learning unit 24 repeats the adjustment of the parameter 48 until the loss L0 is equal to or smaller than a predetermined threshold value. As a result, in a case in which the simple radiation image G0 is input, the parameter 48 is adjusted so as to output the bone density of the target bone, and the learned neural network 23A is constructed. The constructed learned neural network 23A is stored in the storage 13.

Figure 12:
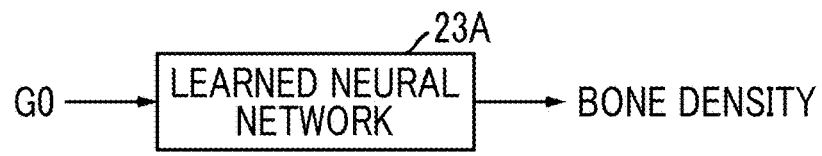
FIG. 12 is a conceptual diagram of processing performed by a learned neural network.

FIG. 12 is a conceptual diagram of processing performed by the learned neural network 23A. As shown in FIG. 12, in a case in which the simple radiation image G0 of a patient is input to the learned neural network 23A constructed as described above, the learned neural network 23A outputs the bone density for the target bone (that is, the femur) included in the input simple radiation image G0.

Figure 13:
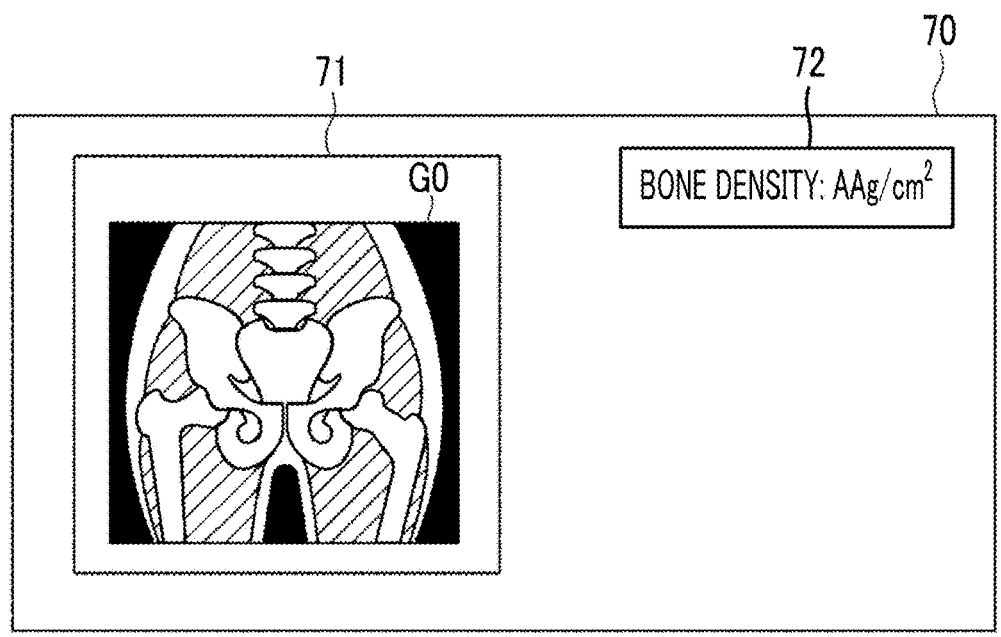
FIG. 13 is a diagram showing a display screen of a result of estimation.

The display controller 25 displays the result of estimation of the bone density estimated by the estimation unit 23 on the display 14. FIG. 13 is a diagram showing a display screen of the result of estimation. As shown in FIG. 13, a display screen 70 has an image display region 71 and a bone density display region 72. The simple radiation image G0 of the subject H is displayed in the image display region 71. In addition, in the bone density display region 72, the representative value of the bone density in the vicinity of the joint of the femur in the bone density estimated by the estimation unit 23 is displayed.

Figure 14:
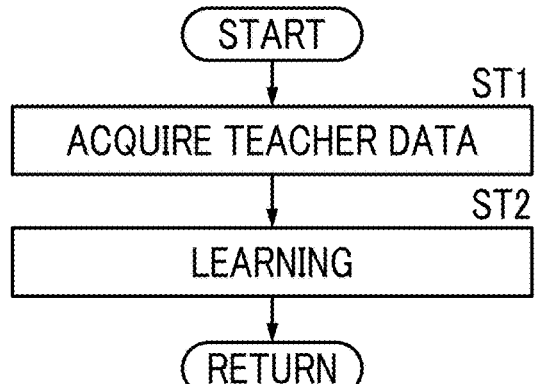
FIG. 14 is a flowchart of learning processing performed in the first embodiment.

Then, the processing performed in the first embodiment will be described. FIG. 14 is a flowchart showing learning processing performed in the first embodiment. First, the information acquisition unit 22 acquires the teacher data 40 from the image storage system 9 (step ST1), and the learning unit 24 inputs the learning data 41 included in the teacher data 40 to the neural network 30 to output the bone density and learns the neural network 30 by using the loss L0 based on the difference from the correct answer data 42 (step ST2), and the processing returns to step ST1. Further, the learning unit 24 repeats the processing of steps ST1 and ST2 until the loss L0 reaches the predetermined threshold value, and terminates the learning processing. Note that the learning unit 24 may terminate the learning processing by repeating the learning a predetermined number of times. As a result, the learning unit 24 constructs the learned neural network 23A.

Figure 15:
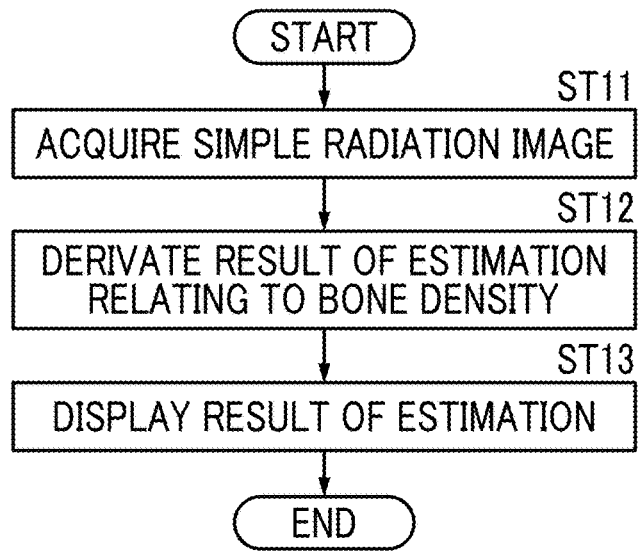
FIG. 15 is a flowchart showing estimation processing performed in the first embodiment.

Then, estimation processing in the first embodiment will be described. FIG. 15 is a flowchart showing the estimation processing in the first embodiment. Note that the simple radiation image G0 is acquired by the imaging and stored in the storage 13. In a case in which an instruction for starting the processing is input from the input device 15, the image acquisition unit 21 acquires the simple radiation image G0 from the storage 13 (step ST11). Then, the estimation unit 23 derives the result of estimation relating to the bone density from the simple radiation image G0 (step ST12). Further, the display controller 25 displays the result of estimation relating to the bone density derived by the estimation unit 23 on the display 14 together with the simple radiation image G0 (step ST13), and terminates the processing.

As described above, in the present embodiment, the result of estimation relating to the bone density of the subject H included in the simple radiation image G0 is derived by using the learned neural network 23A constructed by performing learning with the first and second radiation images G1 and G2 as teacher data. Here, in the present embodiment, the two radiation images, the first and second radiation images G1 and G2, are used for learning the neural network. Therefore, the learned neural network 23A can derive the result of estimation relating to the bone density from the simple radiation image G0 with higher accuracy as compared with a case in which one radiation image and the information relating to the bone density are used as the teacher data. Therefore, according to the present embodiment, the result of estimation relating to the bone density can be derived with higher accuracy.

Note that in the first embodiment, as the bone density of the correct answer data 42, a value measured by the DXA method or an ultrasound method may be used. A device that measures the bone density by using the ultrasound method applies ultrasound waves to a lumbar region to measure the bone density of the lumbar region, or applies the ultrasound waves to a heel to measure the bone density of the heel, for example.

In addition, in the first embodiment, in a case in which the bone density of the correct answer data 42 is derived, the bone part image Gb may be derived by recognizing the bone part and the soft part of the subject H by using at least one radiation image of the first radiation image G1 or the second radiation image G2, deriving an attenuation coefficient of the radiation for the bone part and the soft part by using results of recognition of the bone part and the soft part and the first and second radiation images G1 and G2, performing the energy subtraction processing by using the derived attenuation coefficient. Hereinafter, this case will be described as a second embodiment. Note that the energy subtraction processing in the second embodiment is disclosed in, for example, WO2020/175319A.

Figure 16:
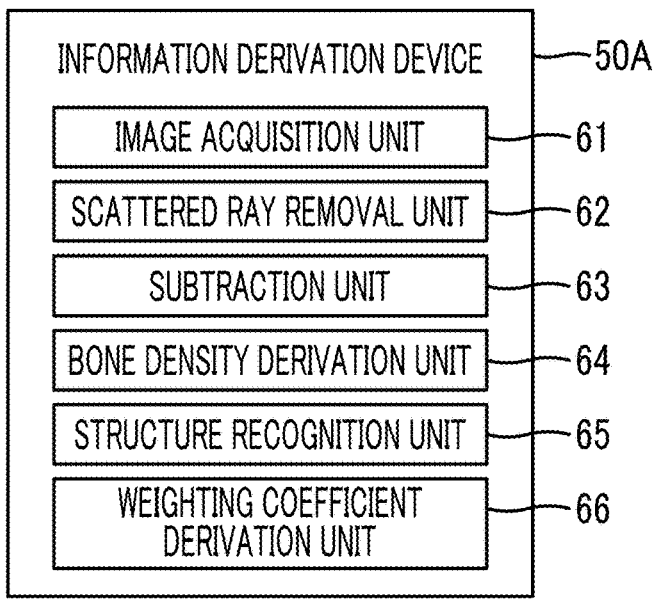
FIG. 16 is a diagram showing a functional configuration of an information derivation device according to a second embodiment.

FIG. 16 is a diagram showing a functional configuration of an information derivation device according to the second embodiment. Note that in FIG. 16, the same reference numerals are assigned to the same configurations as those in FIG. 7, and the detailed description thereof will be omitted. As shown in FIG. 16, an information derivation device 50A according to the second embodiment further comprises a structure recognition unit 65 and a weighting coefficient derivation unit 66 with respect to the information derivation device 50 according to the first embodiment.

The structure recognition unit 65 recognizes a structure included in the subject H by using at least one of the first radiation image G1 or second radiation image G2. In the second embodiment, the structure to be recognized is the bone part and the soft part. In the second embodiment, the structure recognition unit 65 uses both the first and second radiation images G1 and G2 acquired by the image acquisition unit 61 for recognition processing, but any one of the first radiation image G1 or the second radiation image G2 may be used for the recognition processing. Note that the structure recognition unit 65 may recognize the structure by using the first and second radiation images G1 and G2 after scattered ray removal processing, or may recognize the structure by using the first and second radiation images G1 and G2 before the scattered ray removal processing.

The structure recognition unit 65 recognizes a position, a size, and/or a shape of the structure included in the subject H appearing in the first and second radiation images G1 and G2. That is, the recognition processing performed by the structure recognition unit 65 is processing of specifying the position, the size, and/or the shape of the structure having a boundary with another tissue or the like in the subject H appearing in the radiation image. In the second embodiment, the bone part and the soft part of the subject H are recognized as the structure.

The weighting coefficient derivation unit 66 derives an index value representing attenuation of the radiation as a weighting coefficient α to be used for the subtraction processing by using the result of recognition of the structure recognition unit 65 and the first and second radiation images G1 and G2, for the structure recognized by the structure recognition unit 65. The attenuation coefficient is a so-called linear attenuation coefficient, and represents a degree (ratio) of the radiation attenuation due to absorption or scattering. The attenuation coefficient differs depending on a specific composition (density or the like) and the thickness (mass) of the structure through which radiation is transmitted.

Figure 17:
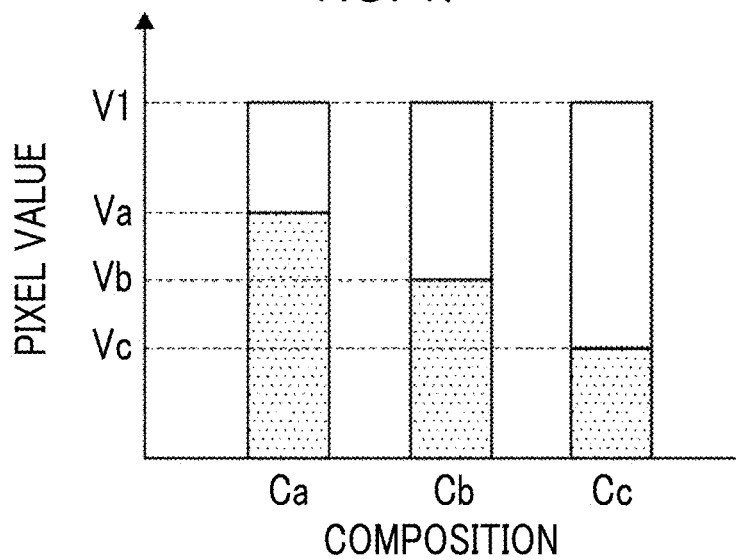
FIG. 17 is a diagram for describing calculation of an index value representing attenuation.
Figure 18:
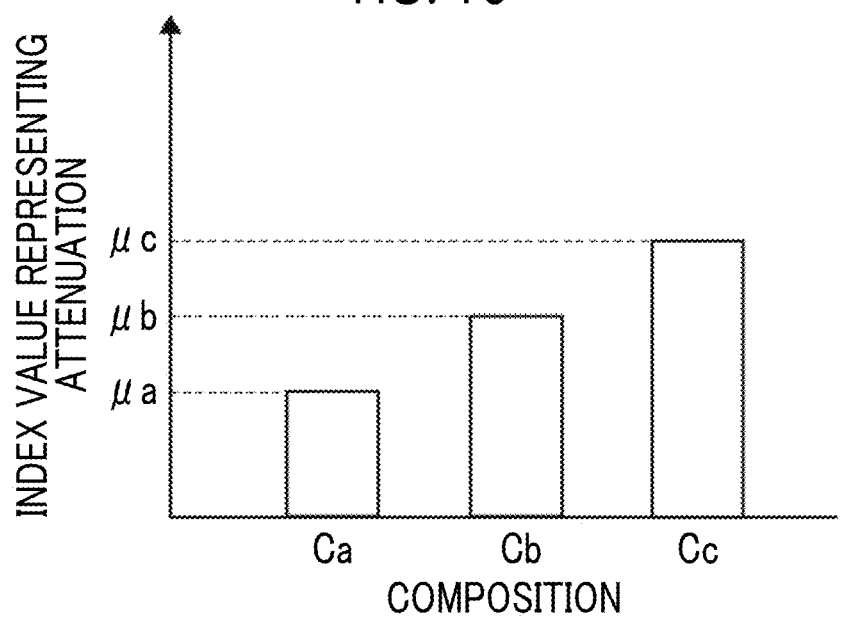
FIG. 18 is a diagram for describing the calculation of the index value representing the attenuation.

The weighting coefficient derivation unit 66 calculates the index value representing the attenuation by using a ratio or a difference of the pixel values in the corresponding pixels of the first and second radiation images G1 and G2. FIGS. 17 and 18 are diagrams for describing the calculation of the index value representing the attenuation. Note that in FIG. 17 and FIG. 18, the calculation of the index value representing the attenuation for the three structures will be described. As shown in FIG. 17, it is assumed that three types of structures having the compositions "Ca", "Cb", and "Cc" are present in the first radiation image G1 and these pixel values in the first radiation image G1 are all "V1". On the other hand, in the second radiation image G2, the pixel values of the corresponding pixels are "Va", "Vb", and "Vc", respectively. A degree of decrease in the pixel value corresponds to a degree of the attenuation of the radiation by each structure (each composition). Therefore, as shown in FIG. 18, the weighting coefficient derivation unit 66 can calculate an index value μa representing the attenuation of the structure of the composition "Ca", an index value μb representing the attenuation of the structure of the composition "Cb", and an index value μc representing the attenuation of the structure of the composition "Cc" by using the ratio or the difference of the pixel value of the first radiation image G1 and the pixel value of the corresponding second radiation image G2. In the second embodiment, the weighting coefficient derivation unit 66 calculates the index value representing the attenuation of the bone part and the index value representing the attenuation of the soft part by using the bone part and the soft part as the composition.

Note that in a case in which the ratio or the difference of the pixel value of the first radiation image G1 and the pixel value of the corresponding pixel of the second radiation image G2 is known, the index value μ representing the attenuation can be calculated. Therefore, for the sake of description, the pixel values of the compositions "Ca", "Cb", and "Cc" are set to be "V1" common in the first radiation image G1, but it is not necessary to set the pixel values of the compositions "Ca", "Cb", and "Cc" to be common in the first radiation image G1.

In the present embodiment, the bone part image Gb is derived by the subtraction unit 63. Therefore, the weighting coefficient derivation unit 66 derives a ratio Gs1($x,y$)/Gs2($x,y$) of a pixel value Gs1($x,y$) of the first radiation image G1, which is the low-energy image, and a pixel value Gs2($x,y$) of the second radiation image G2, which is the high-energy image, as the index value representing the attenuation, that is, the weighting coefficient α in Expression (1) for the soft region in the first and second radiation images G1 and G2. Note that the ratio Gs1($x,y$)/Gs2($x,y$) represents a ratio μls/μhs of an attenuation coefficient μls for the low-energy radiation to an attenuation coefficient μhs for the high-energy radiation in the soft part.

In the second embodiment, the subtraction unit 63 derives the bone part image Gb by performing the energy subtraction processing by Expression (1) by using the weighting coefficient α derived by the weighting coefficient derivation unit 66. The weighting coefficient α in Expression (1) is derived from the attenuation coefficient of the bone part and the attenuation coefficient of the soft part derived by the weighting coefficient derivation unit 66.

Further, in the second embodiment, the bone density derivation unit 64 derives the bone density B and the representative value of the bone density B in the target bone by using the bone part image Gb derived by the subtraction unit 63.

Figure 19:
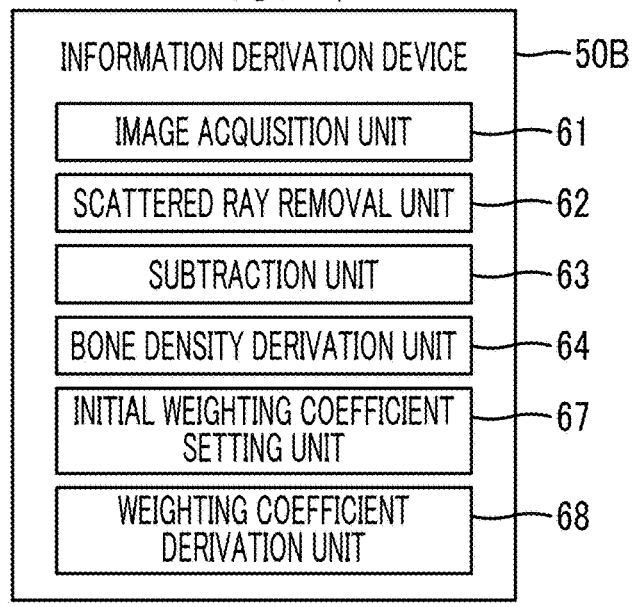
FIG. 19 is a diagram showing a functional configuration of an information derivation device according to a third embodiment.

Then, a third embodiment of the present disclosure will be described. FIG. 19 is a diagram showing a functional configuration of an information derivation device according to the third embodiment. Note that in FIG. 19, the same reference numerals are assigned to the same configurations as those in FIG. 7, and the detailed description thereof will be omitted. In the third embodiment, in a case in which the bone density, which is the correct answer data 42, is derived, the bone part image Gb is derived by deriving a new weighting coefficient used for the weighting subtraction based on the pixel value of the bone part included in the bone part image Gb, deriving a new bone part image by performing the weighting subtraction on the first and second radiation images G1 and G2 by using the new weighting coefficient, and repeating the derivation of a further new weighting coefficient based on the new bone part image and the derivation of a further new bone part image based on the further new weighting coefficient.

Therefore, as shown in FIG. 19, an information derivation device 50B according to the third embodiment further comprises an initial weighting coefficient setting unit 67 and a weighting coefficient derivation unit 68 with respect to the information derivation device 50 according to the first embodiment.

The initial weighting coefficient setting unit 67 sets the initial weighting coefficient, which is the initial value of the weighting coefficient in a case in which the subtraction unit 63 performs the subtraction processing, based on the body thickness distribution in a case in which the scattered ray removal unit 62 satisfies the termination condition. Here, in the third embodiment, the subtraction unit 63 derives the bone part image Gb by Expression (1) by using the initial weighting coefficient set by the initial weighting coefficient setting unit 67 and the weighting coefficient α derived by the weighting coefficient derivation unit 68.

Figure 20:
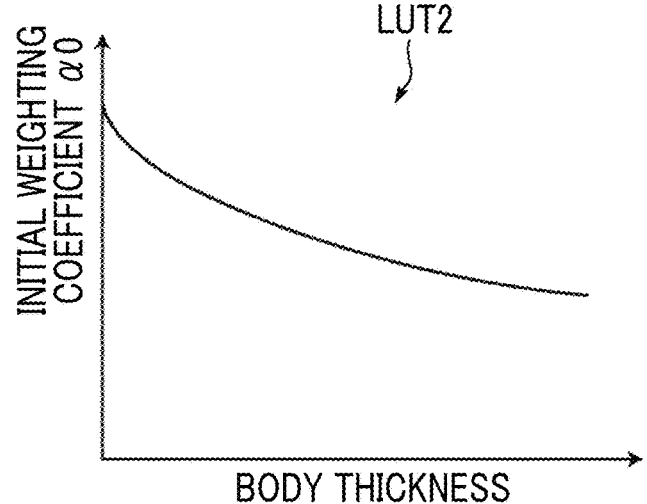
FIG. 20 is a diagram showing a table that defines a relationship between a body thickness distribution and an initial weighting coefficient.

The initial weighting coefficient setting unit 67 sets an initial weighting coefficient α0, which is the initial value of the weighting coefficient, based on the body thickness distribution in a case in which the scattered ray removal unit 62 satisfies the termination condition. In the third embodiment, as shown in FIG. 20, a table LUT2 that defines a relationship between the body thickness distribution and the initial weighting coefficient α0 is stored in the storage 53. The initial weighting coefficient setting unit 67 sets the initial weighting coefficient α0 based on the body thickness distribution with reference to the table LUT2.

Here, since a degree of the beam hardening described above depends on a thickness ts of the soft part and a thickness tb of the bone part in the subject H, an attenuation coefficient μs of the soft part and an attenuation coefficient μb of the bone part can be defined μs(ts, tb) and μb(ts, tb) as functions of ts and tb.

In the energy subtraction processing, since there are the images having two different energy distributions, the attenuation coefficient of the soft part of the low-energy image (first radiation image G1 in the present embodiment) can be represented by μls(ts, tb), and the attenuation coefficient of the bone part thereof can be represented by μlb(ts, tb). In addition, the attenuation coefficient of the soft part of the high-energy image (second radiation image G2 in the present embodiment) can be represented by μhs(ts, tb), and the attenuation coefficient of the bone part thereof can be represented by μhb(ts, tb).

In order to derive the bone part image Gb, it is necessary to eliminate the contrast of the soft part included in the radiation image. Therefore, the weighting coefficient α can be obtained by α=μls(ts, tb)/μhs(ts, tb) by using the ratio of the attenuation coefficient of the soft part. That is, the weighting coefficient α can be represented as a function of the thickness ts of the soft part and the thickness tb of the bone part.

In the third embodiment, the subtraction unit 63 first performs the subtraction processing of performing the weighting subtraction on the first and second radiation images G1 and G2 between the corresponding pixels by using the initial weighting coefficient α0 set by the initial weighting coefficient setting unit 67. Thereafter, as will be described below, the subtraction processing is performed by using a weighting coefficient anew derived by the weighting coefficient derivation unit 68.

Figure 21:
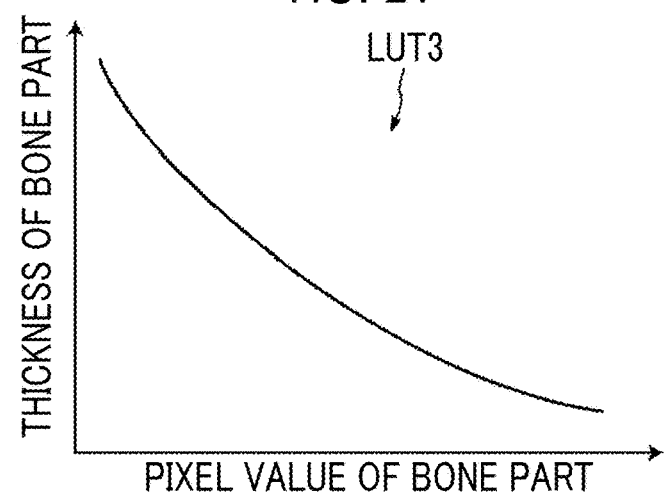
FIG. 21 is a diagram showing a table that defines a relationship between a pixel value of the bone part and a thickness of the bone part.

The weighting coefficient derivation unit 68 derives the new weighting coefficient anew based on the pixel value Gb(x,y) of the bone part included in the bone part image Gb. Here, the pixel value Gb(x,y) of the bone part corresponds to the thickness of the bone part of the subject H. Therefore, in the third embodiment, the radiation image of a standard object is acquired as a standard radiation image by imaging the standard object simulating the bone part having various thicknesses in advance. Further, in advance, a table that defines the relationship between the pixel value of the bone part and the thickness thereof is derived by using a relationship between the pixel value of the region of the standard object and the thickness of the standard object in the standard radiation image and stored in the storage 53. FIG. 21 is a diagram showing the table that defines the relationship between the pixel value of the bone part and the thickness of the bone part. In a table LUT3 shown in FIG. 21, the bone part is thicker as the pixel value Gb(x,y) of the bone part is lower (that is, the brightness is higher).

The weighting coefficient derivation unit 68 derives the thickness tb of the bone part in each pixel of the bone part image Gb from each pixel value Gb(x,y) of the bone part image Gb with reference to the table LUT3. Note that the region in the bone part image Gb in which the bone part is not present consists only of the soft part, the thickness tb of the bone part is 0. On the other hand, in the bone part image Gb, in the pixel in which the thickness tb of the bone part is not 0, the weighting coefficient derivation unit 68 derives the thickness ts of the soft part by subtracting the thickness tb of the bone part from the body thickness distribution in a case in which the scattered ray removal unit 62 satisfies the termination condition.

Figure 22:
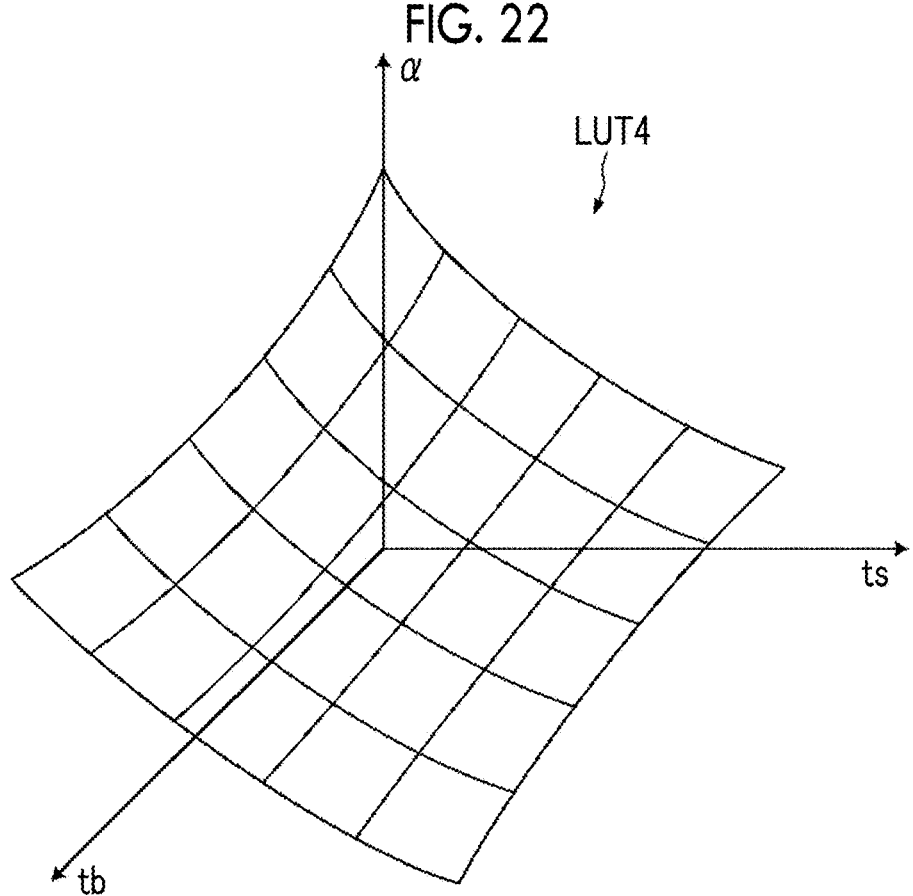
FIG. 22 is a diagram showing a table that defines a relationship between a thickness of the soft part, the thickness of the bone part, and a weighting coefficient.

As described above, the weighting coefficient α can be represented as the function of the thickness ts of the soft part and the thickness tb of the bone part. In the third embodiment, the storage 53 stores a table that defines a relationship between the thickness ts of the soft part, the thickness tb of the bone part, and the weighting coefficient α. FIG. 22 is a diagram showing a table that defines the relationship between the thickness ts of the soft part, the thickness tb of the bone part, and the weighting coefficient α. As shown in FIG. 22, a table LUT4 three-dimensionally represents the relationship between the thickness ts of the soft part, the thickness tb of the bone part, and the weighting coefficient α. Here, in the table LUT4, the weighting coefficient α is smaller as the thickness ts of the soft part and the thickness tb of the bone part are larger.

Note that in the third embodiment, a plurality of the tables LUT4 are prepared and stored in the storage of the information derivation device 50B in accordance with the energy distribution of the radiation used at the time of imaging. The weighting coefficient derivation unit 68 acquires information on the energy distribution of the radiation used at the time of imaging based on the imaging conditions, reads out the table LUT4 corresponding to the acquired information of the energy distribution from the storage, and uses the read out table LUT4 for deriving the weighting coefficient. Further, the weighting coefficient derivation unit 68 derives the new weighting coefficient anew with reference to the table LUT4 based on the derived thickness tb of the bone part and the thickness ts of the soft part.

The subtraction unit 63 derives a new bone part image Gbnew by Expression (1) by using the new weighting coefficient anew derived by the weighting coefficient derivation unit 68.

Note that the new bone part image Gbnew may be used as the final bone part image Gb, but in the third embodiment, the derivation of the weighting coefficient α and the subtraction processing are repeatedly performed.

That is, the weighting coefficient derivation unit 68 derives a new thickness tbnew of the bone part with reference to the table LUT3 based on the pixel value of the bone part in the new bone part image Gbnew. Further, the weighting coefficient derivation unit 68 derives a difference Δtb between a new thickness tbnew of the bone part and the thickness tb of the bone part obtained in the previous processing, and determines whether or not the difference Δtb is smaller than a predetermined threshold value. In a case in which the difference Δtb is equal to or larger than the threshold value, the weighting coefficient derivation unit 68 derives a new thickness tsnew of the soft part from the new thickness tbnew of the bone part, and derives a further new weighting coefficient anew with reference to the table LUT4 based on the new thickness tbnew of the bone part and the new thickness tsnew of the soft part.

The subtraction unit 63 performs the subtraction processing by using the further new weighting coefficient anew, and derives a further new bone part image Gbnew.

Then, the weighting coefficient derivation unit 68 derives a further new thickness tbnew of the bone part based on the further new bone part image Gbnew, and derives a difference Δtb between the further new thickness tbnew of the bone part and the thickness tb of the bone part obtained in the previous processing.

In the third embodiment, the subtraction unit 63 and the weighting coefficient derivation unit 68 repeat the subtraction processing and the derivation of the weighting coefficient anew until the difference Δtb derived by the weighting coefficient derivation unit 68 is smaller than the predetermined threshold value.

Further, in the third embodiment, the bone density derivation unit 64 derives the bone density B and the representative value of the bone density B in the target bone by using the bone part image Gb in a case in which the difference Δtb is smaller than the threshold value.

Figure 23:
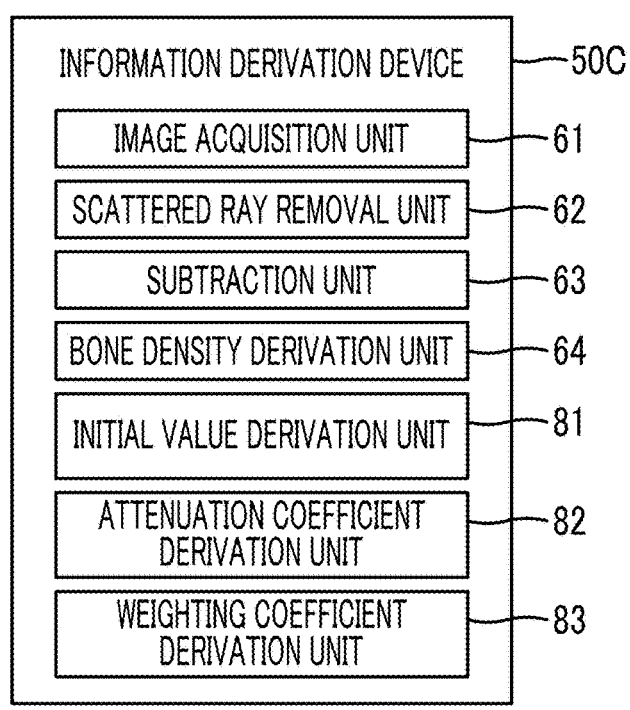
FIG. 23 is a diagram showing a functional configuration of an information derivation device according to a fourth embodiment.

Then, a fourth embodiment of the present disclosure will be described. FIG. 23 is a diagram showing a functional configuration of an information derivation device according to the fourth embodiment. Note that in FIG. 23, the same reference numerals are assigned to the same configurations as those in FIG. 7, and the detailed description thereof will be omitted. In the fourth embodiment of the present disclosure, in a case in which the bone density, which is the correct answer data 42, is derived, the bone part image Gb is derived by deriving, for each of different energy distributions, the difference between a value of the attenuation coefficient of the soft part×the thickness of the soft part+the attenuation coefficient of the bone part×the thickness of the bone part, and each pixel value of the radiation image while changing, from initial values, the attenuation coefficient of the soft part for each of different energy distributions, the thickness of the soft part, the attenuation coefficient of the bone part for each of different energy distributions, and the thickness of the bone part, deriving the attenuation coefficient of the soft part and the attenuation coefficient of the bone part for each of different energy distributions, at which the difference is minimized or the difference is smaller than the predetermined threshold value, and performing the energy subtraction processing by using the weighting coefficient derived based on the attenuation coefficient of the soft part and the attenuation coefficient of the bone part.

Therefore, as shown in FIG. 23, an information derivation device 50C according to the fourth embodiment further comprises an initial value derivation unit 81, an attenuation coefficient derivation unit 82, and a weighting coefficient derivation unit 83 with respect to the information derivation device 50 according to the first embodiment.

The initial value derivation unit 81 derives the initial values of the attenuation coefficient of the soft part for each of different energy distributions, the thickness of the soft part, the attenuation coefficient of the bone part for each of different energy distributions, and the thickness of the bone part for deriving the weighting coefficient in a case of performing the energy subtraction processing. Specifically, the initial values $\mu ls0$, $\mu hs0$, $ts0$, $\mu lb0$, $\mu hb0$, and $tb0$ of the attenuation coefficient $\mu ls$ of the soft part for the low-energy radiation, the attenuation coefficient $\mu hs$ of the soft part for the high-energy radiation, the thickness $ts$ of the soft part, the attenuation coefficient $\mu lb$ of the bone part for the low-energy radiation, the attenuation coefficient $\mu hb$ of the bone part for the high-energy radiation, and the thickness $tb$ of the bone part are derived.

In the fourth embodiment, as shown in Expression (1), the subtraction unit 63 derives the bone part image Gb obtained by extracting the bone part in the subject H by performing the subtraction processing of performing the weighting subtraction on the first and second radiation images G1 and G2 between the corresponding pixels by using the weighting coefficient derived by the weighting coefficient derivation unit 83 as described below.

Here, as described above, the attenuation coefficient $\mu s$ of the soft part and the attenuation coefficient $\mu b$ of the bone part can be defined as $\mu s(ts, tb)$ and $\mu b(ts, tb)$ as functions of $ts$ and $tb$. Therefore, in the fourth embodiment as well as in the third embodiment, the attenuation coefficient of the soft part of the low-energy image (first radiation image G1 in the present embodiment) can be represented by $\mu ls(ts, tb)$, and the attenuation coefficient of the bone part can be represented by $\mu lb(ts, tb)$. In addition, the attenuation coefficient of the soft part of the high-energy image (second radiation image G2 in the present embodiment) can be represented by $\mu hs(ts, tb)$, and the attenuation coefficient of the bone part thereof can be represented by $\mu hb(ts, tb)$.

In order to derive the bone part image Gb, it is necessary to eliminate the contrast of the soft part included in the radiation image. Therefore, the weighting coefficient $\alpha$ can be obtained by $\alpha=\mu ls(ts, tb)/\mu hs(ts, tb)$ by using the ratio of the attenuation coefficient of the soft part. Note that in the following description, the attenuation coefficients $\mu ls(ts, tb)$, $\mu hs(ts, tb)$, $\mu lb(ts, tb)$, and $\mu hb(ts, tb)$ will be simply represented by the attenuation coefficients $\mu ls$, $\mu hs$, $\mu lb$, and $\mu hb$ by omitting $(ts, tb)$.

The initial value derivation unit 81 uses the body thickness distribution in a case in which the scattered ray removal unit 62 satisfies the termination condition as the initial value $ts0$ of the thickness $ts$ of the soft part. Note that in the fourth embodiment, the body thickness distribution used in a case of performing the scattered ray removal processing is the body thickness distribution assuming that the subject H consists of only the soft part. Therefore, the initial value $tb0$ of the thickness $tb$ of the bone part is 0. In addition, as the initial values $\mu ls0$, $\mu hs0$, $\mu lb0$, and $\mu hb0$ of the attenuation coefficients, values corresponding to the initial values $ts0$ and $tb0$ of the thicknesses $ts$ and $tb$ of the soft part and bone part are derived. In the fourth embodiment, since the initial value $tb0$ of the thickness $tb$ of the bone part is 0, the attenuation coefficients $\mu lb0$ and $\mu hb0$ of the bone part are 0. As the attenuation coefficients $\mu ls0$ and $\mu hs0$ of the soft part, a value corresponding to the initial value $ts0$ of the thickness $ts$ of the soft part is derived. Therefore, in the fourth embodiment, a table that defines a relationship between the initial value $ts0$ of the thickness $ts$ of the soft part and the initial values $\mu ls0$ and $\alpha hs0$ of the attenuation coefficients of the soft part is stored in the storage 53.

Figure 24:
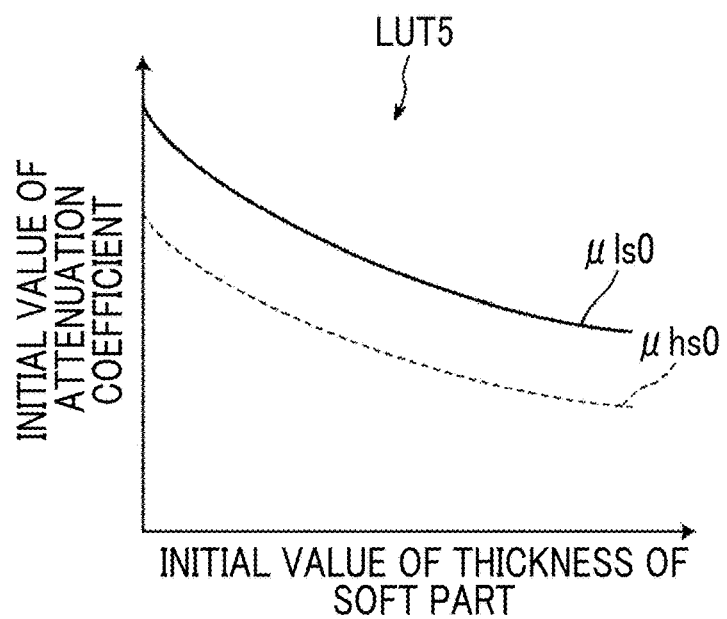
FIG. 24 is a diagram showing a table that defines a relationship between an initial value of the thickness of the soft part and an initial value of an attenuation coefficient of the soft part.

FIG. 24 is a diagram showing a table that defines the relationship between the initial value $ts0$ of the thickness $ts$ of the soft part and the initial values $\mu ls0$ and $\mu hs0$ of the attenuation coefficients of the soft part. The initial value derivation unit 81 derives the initial values $\mu ls0$ and $\mu hs0$ of the attenuation coefficient of the soft part depending on the initial value $ts0$ of the thickness $ts$ of the soft part with reference to a table LUT5 stored in the storage 53.

The attenuation coefficient derivation unit 82 derives the attenuation coefficients $\mu ls$ and $\mu hs$ of the soft part and the attenuation coefficients $\mu lb$ and $\mu hb$ of the bone part for each of different energy distributions. Here, for the energy subtraction processing, the low-energy image and the high-energy image are acquired by imaging the subject H with the radiation having different energy distributions. In the present embodiment, the first radiation image G1 is the low-energy image and the second radiation image G2 is the high-energy image. The pixel value $G1(x,y)$ of each pixel of the first radiation image G1, which is the low-energy image, and the pixel value $G2(x,y)$ of each pixel of the second radiation image G2, which is the high-energy image, are represented by Expression (3) and Expression (4) by using the thickness $ts(x,y)$ of the soft part, the thickness $tb(x,y)$ of the bone part, and the attenuation coefficients $\mu ls(x,y)$, $\mu hs(x,y)$, $\mu lb(x,y)$, and $\mu hb(x,y)$ at the corresponding pixel position. Note that in Expression (3) and Expression (4), the description of $(x,y)$ is omitted.

$$G1 = \mu ls \times ts + \mu lb \times tb \quad (3)$$

$$G2 = \mu hs \times ts + \mu hb \times tb \quad (4)$$

In order to derive the weighting coefficient $\alpha$ for performing the energy subtraction processing, it is necessary to derive the attenuation coefficients $\mu ls(x,y)$, $\mu hs(x,y)$, $\mu lb(x,y)$, and $\mu hb(x,y)$. The attenuation coefficients $\mu ls(x,y)$, $\mu hs(x,y)$, $\mu lb(x,y)$, and $\mu hb(x,y)$ are represented as functions of the thickness $ts$ of the soft part and the thickness $tb$ of the bone part as described above. Therefore, in order to derive the attenuation coefficients $\mu ls(x,y)$, $\mu hs(x,y)$, $\mu lb(x,y)$, and $\mu hb(x,y)$, it is necessary to derive the thickness $ts$ of the soft part and the thickness $tb$ of the bone part. $ts$ and $tb$ in Expression (3) and Expression (4) are solved by Expression (5) and Expression (6).

$$ts = \{\mu hb \times G1 - \mu lb \times G2\}/\{\mu ls \times \mu hb - \mu lb \times \mu hs\} \quad (5)$$

$$tb = \{\mu ls \times G2 - \mu hs \times G1\}/\{\mu ls \times \mu hb - \mu lb \times \mu hs\} \quad (6)$$

Here, the attenuation coefficients $\mu ls(x,y)$, $\mu hs(x,y)$, $\mu lb(x,y)$, and $\mu hb(x,y)$ on the right side of Expression (5) and Expression (6) are represented as the functions of the thickness $ts$ of the soft part and the thickness $tb$ of the bone part, and thus Expression (5) and Expression (6) cannot be solved algebraically.

Therefore, in the fourth embodiment, error functions EL and EH shown in Expression (7) and Expression (8) are set. The error functions EL and EH correspond to the difference between the value of the attenuation coefficient of the soft part×the thickness of the soft part+the attenuation coefficient of the bone part×the thickness of the bone part and each pixel value of the radiation image for each of different energy distributions. Further, in order to minimize the error functions EL and EH at the same time, in the fourth embodiment, an error function E0 shown in Expression (9) is set. Further, while changing the thickness ts of the soft part, the thickness tb of the bone part, and the attenuation coefficients μls, μhs, μlb, and μhb from the initial values, the error function E0 is minimized, or a combination of the thickness ts of the soft part and the thickness tb of the bone part at which the error function E0 is smaller than a predetermined threshold value is derived. In this case, it is preferable to derive the thickness ts of the soft part and the thickness tb of the bone part by using an optimization algorithm, such as the steepest descent method and the conjugate gradient method. As the initial values of the thickness ts of the soft part, the thickness tb of the bone part, and the attenuation coefficients μls, μhs, μlb, and μhb used in this case, ts0, tb0, μls0, μhs0, μlb0, and μhb0 derived by the initial value derivation unit 81 are used.

$$EL = G1 - \{\mu ls \times ts + \mu lb \times tb\} \quad (7)$$

$$EH = G2 - \{\mu hs \times ts + \mu hb \times tb\} \quad (8)$$

$$E0 = EL^2 + Eh^2 \quad (9)$$

Note that the attenuation coefficient used in the process for deriving the thickness ts of the soft part and the thickness tb of the bone part is derived with reference to a table that defines a relationship between the thickness ts of the soft part, the thickness tb of the bone part, which are predetermined, and the attenuation coefficient. Such a table is stored in the storage 53 of the information derivation device.

Figure 25:
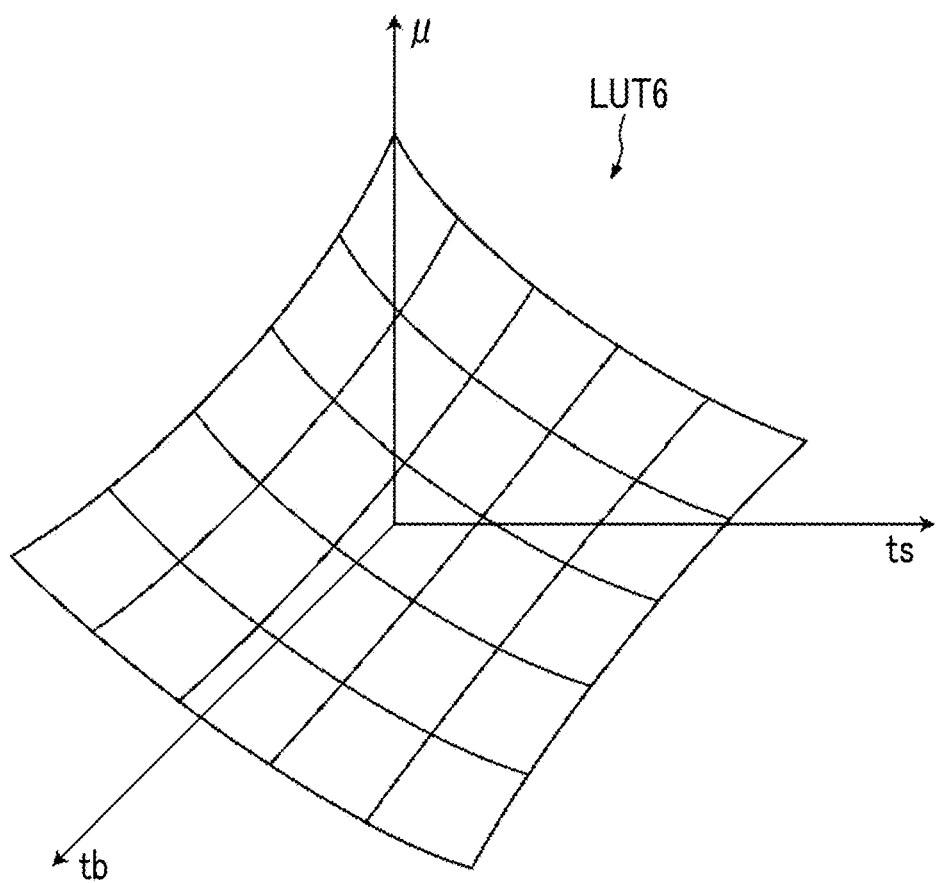
FIG. 25 is a diagram showing a table that defines a relationship between the thickness of the soft part, the thickness of the bone part, and the attenuation coefficient.

FIG. 25 is a diagram showing the table that defines the relationship between the thickness ts of the soft part, the thickness tb of the bone part, and the attenuation coefficient. As shown in FIG. 25, a table LUT6 three-dimensionally represents the relationship between the thickness ts of the soft part, the thickness tb of the bone part, and the attenuation coefficient μ. Note that although only one LUT6 is shown in FIG. 25, the table is prepared for each of the attenuation coefficients μls, μhs, μlb, and μhb and stored in the storage. Here, in the table LUT6, the attenuation coefficient μ is smaller as the thickness ts of the soft part and the thickness tb of the bone part are larger.

In a case in which the thickness ts of the soft part and the thickness tb of the bone part in a case in which the error function E0 is minimized or the error function E0 is smaller than the predetermined threshold value are derived, the attenuation coefficient derivation unit 82 derives the attenuation coefficients μls, μhs, μlb, and μhb with reference to the table LUT6.

The weighting coefficient derivation unit 83 derives the weighting coefficient α used by the subtraction unit 63 in a case of performing the subtraction processing. That is, the weighting coefficient derivation unit 83 derives the weighting coefficient α by performing a calculation of α=μls/μhs by using the attenuation coefficients μls, μhs, μlb, and μhb derived by the attenuation coefficient derivation unit 82.

In the fourth embodiment, the subtraction unit 63 derives the bone part image Gb by Expression (1) by using the weighting coefficient α derived by the weighting coefficient derivation unit 83. Further, the bone density derivation unit 64 derives the bone density B and the representative value of the bone density B in the target bone.

Figure 26:
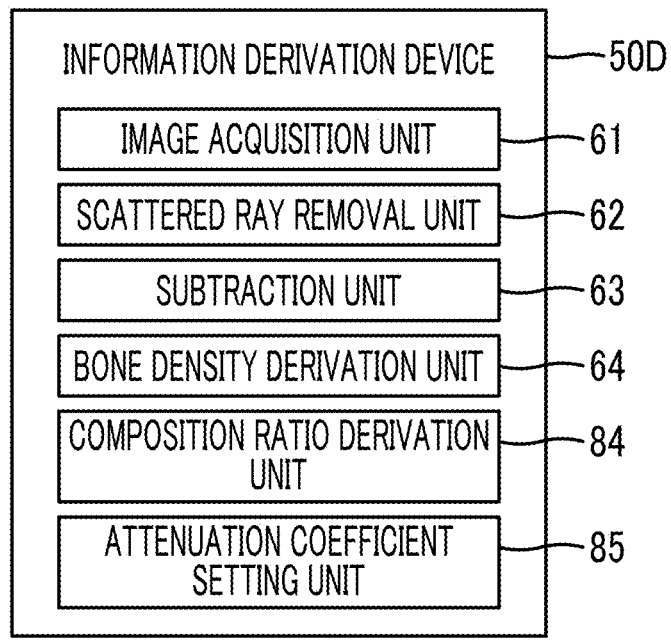
FIG. 26 is a diagram showing a functional configuration of an information derivation device according to a fifth embodiment.

Then, a fifth embodiment of the present disclosure will be described. FIG. 26 is a diagram showing a functional configuration of an information derivation device according to the fifth embodiment. Note that in FIG. 26, the same reference numerals are assigned to the same configurations as those in FIG. 7, and the detailed description thereof will be omitted. In the fifth embodiment of the present disclosure, in a case in which the bone density, which is the correct answer data 42, is derived, the bone part image Gb is derived by deriving a composition ratio of a plurality of compositions included in the soft part of the subject H, deriving, for each pixel of the first and second radiation images G1 and G2, the attenuation coefficient of the soft part for each of different energy distributions depending on the composition ratio, and performing the subtraction processing by using the weighting coefficient derived based on the derived attenuation coefficient of the soft part and the predetermined attenuation coefficient of the bone part.

Therefore, as shown in FIG. 26, an information derivation device 50D according to the fifth embodiment further comprises a composition ratio derivation unit 84 and an attenuation coefficient setting unit 85 with respect to the information derivation device 50 according to the first embodiment.

The composition ratio derivation unit 84 acquires the composition ratio of the subject H. In the fifth embodiment, the composition ratio derivation unit 84 acquires the composition ratio by deriving the composition ratio of the subject H based on the first and second radiation images G1 and G2. Note that in the fifth embodiment, the composition ratio of the fat is derived as the composition ratio. Therefore, although the subject H includes the bone part, for the sake of description, the description will be made on assumption that the first and second radiation images G1 and G2 do not include the bone part and include only the soft part.

In order to derive the composition ratio, the composition ratio derivation unit 84 first derives the body thicknesses of the subject H for each pixel of the first and second radiation images G1 and G2 as the first body thickness and the second body thickness. Specifically, the composition ratio derivation unit 84 derives a first body thickness t1 of the subject H by assuming that a brightness distribution of the first radiation image G1 coincides with the body thickness distribution of the subject H, and converting the pixel value of the first radiation image G1 into the thickness by using the attenuation coefficient of the radiation in the muscle of the subject H. In addition, the composition ratio derivation unit 84 derives a second body thickness t2 of the subject H by assuming that a brightness distribution of the second radiation image G2 coincides with the body thickness distribution of the subject H, and converting the pixel value of the second radiation image G2 into the thickness by using the attenuation coefficient in the muscle of the subject H.

Here, since the degree of the beam hardening described above depends on a thickness tf of the fat and a thickness tm of the muscle in the subject H, an attenuation coefficient μf of the fat and an attenuation coefficient μm of the muscle are can be defined as μf(tf, tm) and μm(tf, tm) as non-linear functions of the thickness tf of the fat and the thickness tm of the muscle.

In the fifth embodiment, the attenuation coefficient of the fat of the first radiation image G1, which is the low-energy image, can be represented as μlf(tf, tm), and the attenuation coefficient of the muscle can be represented as μlm(tf, tm). In addition, the attenuation coefficient of the fat of the second radiation image G2, which is the high-energy image, can be represented as μhf(tf, tm), and the attenuation coefficient of the muscle can be represented as μhm(tf, tm).

In addition, the pixel value G1(x,y) of each pixel in the soft region of the first radiation image G1, which is the low-energy image, and the pixel value G2(x,y) of each pixel in the soft region of the second radiation image G2, which is the high-energy image, are represented by Expression (10)

and Expression (11), respectively, by using the thickness tf(x,y) of the fat, the thickness tm(x,y) of the muscle, and the attenuation coefficients μlf(x,y), μhf(x,y), μlm(x,y), and μhm (x,y) at the corresponding pixel position. Note that in Expression (10) and Expression (11), the description of (x,y) is omitted.

$$G1=\mu lf \times tf + \mu lm \times tm \quad (10)$$

$$G2=\mu hf \times tf + \mu hm \times tm \quad (11)$$

As described above, in the fifth embodiment, in a case of deriving the first body thickness t1 and the second body thickness t2, the pixel values of the first radiation image G1 and the second radiation image G2 are converted into the thicknesses by using the attenuation coefficient of the muscle in the subject H. Therefore, in the fifth embodiment, the composition ratio derivation unit 84 derives the first body thickness t1 and the second body thickness t2 by Expression (12) and Expression (13). Note that in Expression (12) and Expression (13), the description of (x,y) is omitted.

$$t1=G1/\mu lm \quad (12)$$

$$t2=G2/\mu hm \quad (13)$$

In a case in which the subject H includes only the muscle at the pixel positions from which the first and second body thicknesses t1 and t2 are derived, the first body thickness t1 and the second body thickness t2 coincide with each other. However, in the actual subject H, both the muscle and the fat are included at the same pixel positions of the first and second radiation images G1 and G2. Therefore, the first and second body thicknesses t1 and t2 derived by Expression (12) and Expression (13) do not coincide with the actual body thickness of the subject H. In addition, in the first body thickness t1 derived from the first radiation image G1, which is the low-energy image, and the second body thickness t2 derived from the second radiation image G2, which is the high-energy image, the first body thickness t1 has a larger value than the second body thickness t2.

Figure 27:
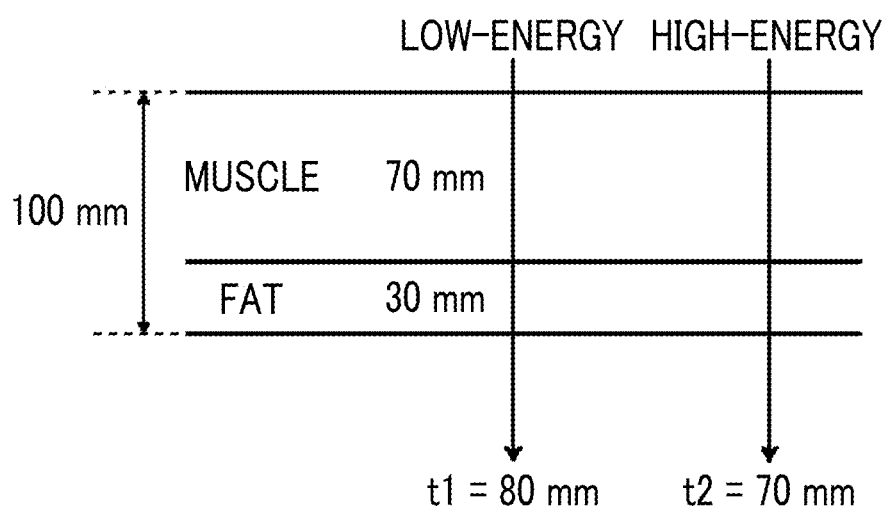
FIG. 27 is a diagram for describing a difference between body thicknesses derived from a low-energy image and a high-energy image.

For example, as shown in FIG. 27, it is assumed that the actual body thickness is 100 mm and the thicknesses of the fat and the muscle are 30 mm and 70 mm, respectively. In this case, the first body thickness t1 derived from the first radiation image G1 acquired by the low-energy radiation is derived to be, for example, 80 mm, and the second body thickness t2 derived by the second radiation image G2 acquired by the high-energy radiation is derived to be, for example, 70 mm. In addition, a difference between the first body thickness t1 and the second body thickness t2 is larger as the composition ratio of the fat is larger.

Here, the difference between the first body thickness t1 and the second body thickness t2 is changed depending on the composition ratio of the fat and the muscle in the subject H. Therefore, in the fifth embodiment, a subject model in which the composition ratio of the fat is variously changed is imaged with the radiation having different energy distributions, the body thicknesses are derived from the two radiation images acquired in this way, respectively, and a table in which a difference between the body thicknesses derived from the two radiation images and the composition ratio of the fat are associated with each other is created in advance and stored in the storage 53.

Figure 28:
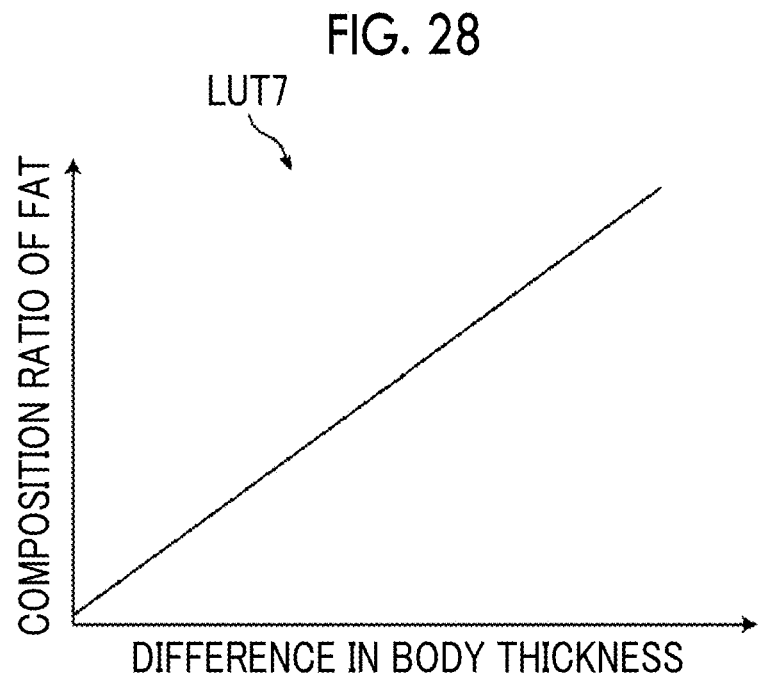
FIG. 28 is a diagram showing a table in which a difference between the body thicknesses derived from two radiation images and a composition ratio of fat are associated with each other.

FIG. 28 is a diagram showing the table in which the difference between the body thicknesses derived from the two radiation images and the composition ratio of the fat are associated with each other. As shown in FIG. 28, in a table LUT7, a horizontal axis is the difference between the body thicknesses derived from the two radiation images, and a vertical axis is the composition ratio of the fat. As shown in FIG. 28, the composition ratio of the fat is larger as the larger the difference between the body thicknesses derived from the two radiation images is larger. Note that the table in which the difference between the body thicknesses derived from the two radiation images and the composition ratio of the fat are associated with each other is prepared for each radiation energy distribution used at the time of imaging and stored in the storage 53.

The composition ratio derivation unit 84 derives the difference between the first body thickness t1 and the second body thickness t2, which are derived, and derives a composition ratio R(x,y) of the fat with reference to the LUT7 stored in the storage of the information derivation device 50D. Note that the composition ratio of the muscle can be derived by subtracting the derived composition ratio R(x,y) of the fat from 100%.

The attenuation coefficient setting unit 85 sets the attenuation coefficient of the radiation used in a case of acquiring the first and second radiation images G1 and G2 for each pixel of the first and second radiation images G1 and G2 depending on the composition ratio R(x,y) of the fat. Specifically, the attenuation coefficient of the soft part of the subject H is set. Here, in the fifth embodiment, the first radiation image G1 corresponds to the low-energy image, and the second radiation image G2 corresponds to the high-energy image. Therefore, the attenuation coefficient setting unit 85 derives the attenuation coefficient μls(x,y) of the soft part of the low-energy image and the attenuation coefficient μhs(x,y) of the soft part of the high-energy image by Expression (14) and Expression (15). Note that in Expression (14) and Expression (15), the description of (x,y) is omitted. In addition, μlm is the attenuation coefficient of the muscle in the low-energy image, μlf is the attenuation coefficient of the fat in the low-energy image, Om is the attenuation coefficient of the muscle in the high-energy image, and μhf is the attenuation coefficient of the fat in the high-energy image.

$$\mu ls=(1-R)\times\mu lm+R\times\mu lf \quad (14)$$

$$\mu hs=(1-R)\times\mu hm+R\times\mu hf \quad (15)$$

In the fifth embodiment, the subtraction unit 63 performs the subtraction processing by using the attenuation coefficients μls and μhs set by the attenuation coefficient setting unit 85. In this case, the subtraction unit 63 derives the weighting coefficient α in Expression (1). The weighting coefficient α used in the fifth embodiment is derived by α=μls/μhs by using the attenuation coefficient set by the attenuation coefficient setting unit 85. Further, the subtraction unit 63 derives the bone part image Gb by Expression (1) by using the derived weighting coefficient α. Further, the bone density derivation unit 64 derives the bone density B and the representative value of the bone density B in the target bone.

Figure 29:
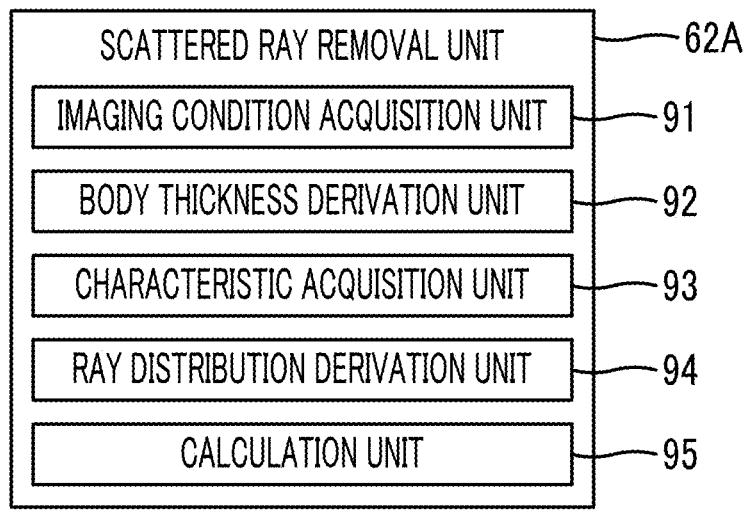
FIG. 29 is a diagram showing a functional configuration of a scattered ray removal unit of an information derivation device according to a sixth embodiment.

Then, an information derivation device according to a sixth embodiment of the present disclosure will be described. Note that a configuration of the information derivation device according to the sixth embodiment is the same as the configuration of the information derivation device 50 according to the first embodiment, and only the processing performed by the scattered ray removal unit 62 is different, so that the detailed description will be omitted here. FIG. 29 is a diagram showing a functional configuration of the scattered ray removal unit of the information derivation device according to the sixth embodiment. As shown in FIG. 29, a scattered ray removal unit 62A of the information derivation device according to the sixth embodiment comprises an imaging condition acquisition unit 91, a body thickness derivation unit 92, a characteristic acquisition unit 93, a ray distribution derivation unit 94, and a calculation unit 95.

Figure 30:
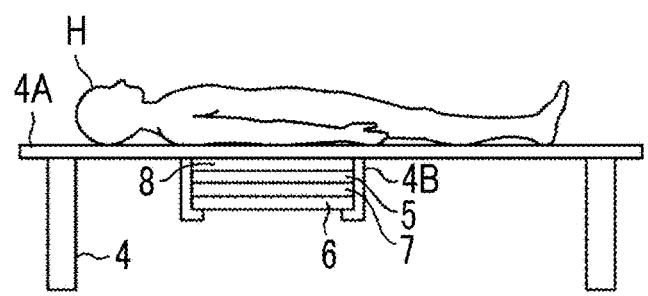
FIG. 30 is a diagram for describing imaging in the sixth embodiment.

Note that in the sixth embodiment, the first and second radiation images G1 and G2 are acquired by imaging the subject H lying on an imaging table 4 by using an imaging apparatus 1A shown in FIG. 30 by further using a scattered ray removal grid 8, and the first and second radiation images G1 and G2 are used as the teacher data 40. Note that in FIG. 30, the imaging table 4 has a top plate 4A, and the scattered ray removal grid (hereinafter, simply referred to as a grid) 8, the first radiation detector 5, the radiation energy conversion filter 7, and the second radiation detector 6 are disposed below the top plate 4A in order from the side of the radiation source 3, and these components are attached below the top plate 4A by an attachment portion 4B.

In a case of generating the teacher data 40, the imaging condition acquisition unit 91 acquires the imaging conditions used at the time of the energy subtraction imaging of the subject H from the image storage system 9 in order to acquire the first and second radiation images G1 and G2 as the learning data 41. Note that in the sixth embodiment, a radiation quality of the radiation is also included as the imaging condition. The radiation quality is defined by using one or more of the tube voltage [kV] of a radiation generator in the radiation source 3, a total filtration amount [mmA1 equivalent], or a half-value layer [mmA1]. The tube voltage means the maximum value of the generated radiation energy distribution. The total filtration amount is obtained by converting the filtration amount of each constituting component which configures the imaging apparatus 1, such as a radiation generator and a collimator, in the radiation source 3 into a thickness of the aluminum. The influence of the beam hardening in the imaging apparatus 1 is larger and the total amount of high-energy components in the wavelength distribution of the radiation is larger as the total filtration amount is larger. The half-value layer is defined by the thickness of the aluminum necessary to attenuate the dose in half with respect to the generated radiation energy distribution. The high-energy components in the wavelength distribution of the radiation is larger as the aluminum in the half-value layer is thicker.

The body thickness derivation unit 92 derives the body thickness distribution of the subject H based on at least one of the first radiation image G1 or the second radiation image G2 and the imaging conditions. Hereinafter, the body thickness distribution derived by the body thickness derivation unit 92 is referred to as the initial body thickness distribution T0. Hereinafter, the derivation of the initial body thickness distribution T0 will be described. Note that in the following description, the derivation of the body thickness and the removal of the scattered ray by using the first radiation image G1 will be described, but the derivation of the body thickness and the removal of the scattered ray can be similarly performed by using the second radiation image G2.

First, in a case in which the radiation source 3 is driven to emit the radiation to the radiation detector 5 in a state in which the subject H is not present, a reaching dose $I0(x,y)$ of the radiation emitted from the radiation source 3 to the radiation detector 5 is represented by Expression (16). In Expression (16), mAs included in the imaging conditions is a tube current-time product, and kV is the tube voltage. Note that the half-value layer is also taken into consideration, the reaching dose $I0(x,y)$ is represented by Expression (16-1). Here, F is a non-linear function that represents the radiation dose that reaches to the radiation detector 5 in a case in which the dose (for example, 1 mAs), which is a standard, is emitted to the radiation detector 5 at the SID (for example, 100 cm), which is a standard, in a state in which the subject H is not present. F is changed for each tube voltage or depending on the tube voltage and the half-value layer. In addition, since the reaching dose I0 is derived for each pixel of the radiation image acquired by the radiation detector 5, (x,y) represents the pixel position of each pixel. In addition, in the following description, in order to include both a case in which the half-value layer is considered and a case in which the half-value layer is not considered, each expression is represented by including mmA1 in parentheses as shown in Expression (16-2).

$$I0(x,y)=mAs \times F(kV)/SID^2 \qquad (16)$$

$$I0(x,y)=mAs \times F(kV,mmA1)/SID^2 \qquad (16-1)$$

$$I0(x,y)=mAs \times F(kV(,mmA1))/SID^2 \qquad (16-2)$$

In addition, in a case in which the initial body thickness distribution is defined as T0, the attenuation coefficient of the subject H in a case of having the initial body thickness distribution T0 is defined as $\mu(T0)$, and a scattered-to-primary ratio, which is a ratio between the scattered ray dose included in the radiation after being transmitted through the subject H having the initial body thickness distribution T0 and a primary ray dose in a case in which a scattered ray spread is not considered is defined as STPR(T0), the dose I1 after being transmitted through the subject H is represented by Expression (17). Note that in Expression (17), the initial body thickness distribution T0, the reaching dose T0, and the dose I1 are derived for each pixel of the simple radiation image G0, but (x,y) is omitted. In addition, STPR is a non-linear function that depends on the tube voltage [kV] and the half-value layer [mmA1] in addition to the body thickness, but in Expression (17), kV and mmA1 are omitted.

$$I1=I0 \times \exp\{-\mu(T0) \times T0\} \times \{1+STPR(T0)\} \qquad (17)$$

In Expression (17), the dose I1 is a pixel value in each pixel of the simple radiation image G0, and the reaching dose I0 is derived by Expression (16) and Expression (16-1). On the other hand, since F and STPR are non-linear functions, Expression (17) cannot be algebraically solved for T0. Therefore, the body thickness derivation unit 92 defines an error function E1 shown in Expression (18) or Expression (18-1). Further, T0 at which the error function E1 is minimized or the error function E1 is smaller than a predetermined threshold value is derived as the initial body thickness distribution. In this case, the body thickness derivation unit 92 derives the initial body thickness distribution T0 by using an optimization algorithm, such as the steepest descent method and the conjugate gradient method.

$$E1=[I1-I0 \times \exp\{-\mu(T0) \times T0\} \times \{1+STPR(T0)\}]^2 \qquad (18)$$

$$E1=|I1-I0 \times \exp\{-\mu(T0) \times T0\} \times \{1+STPR(T0)\}| \qquad (18-1)$$

The characteristic acquisition unit 93 acquires a radiation characteristic of an object interposed between the subject H and the first and second radiation detectors 5 and 6 at the time of imaging. Here, in a case in which the radiation after being transmitted through the subject H is transmitted through the object interposed between the subject H and the radiation detector 5, a transmittance of the radiation is changed depending on the radiation quality of the radiation after being transmitted through the subject H. In addition, a primary ray transmittance and a scattered ray transmittance included in the radiation after being transmitted through the subject H are different due to the difference in the traveling direction of the radiation and the quality of the radiation. Therefore, in the sixth embodiment, as the radiation characteristics of the object, the primary ray transmittance and the scattered ray transmittance of the object are used.

Note that, as described above, in a case in which the radiation after being transmitted through the subject H is transmitted through the object interposed between the subject H and the radiation detector 5, a transmittance of the radiation is changed depending on the radiation quality of the radiation after being transmitted through the subject H. In addition, the radiation quality of the radiation after being transmitted through the subject H depends on the body thickness distribution T of the subject H. Therefore, the primary ray transmittance and the scattered ray transmittance can be represented by Tp(T) and Ts(T), respectively, as functions of the body thickness distribution T of the subject H.

In addition, the radiation quality of the radiation after being transmitted through the subject H also depends on the radiation quality of the radiation source 3 included in the imaging conditions. The radiation quality depends on the tube voltage and the half-value layer. Therefore, strictly speaking, the primary ray transmittance and the scattered ray transmittance are represented by Tp(kV(, mmA1), T) and Ts(kV(, mmA1), T), respectively. Note that in the following description, the primary ray transmittance and the scattered ray transmittance may be simply represented by Tp and Ts.

Here, as described above, the primary ray transmittance Tp and the scattered ray transmittance Ts of the object interposed between the subject H and the radiation detector 5 depend on the body thickness distribution T of the subject H. Therefore, in the sixth embodiment, the primary ray transmittance Tp and the scattered ray transmittance Ts of the object depending on the body thickness distribution T of the subject H are measured by using phantom with various thicknesses that imitate the body thickness distribution T of the subject, a table that defines a relationship between the body thickness distribution T of the subject H and the primary ray transmittance Tp and the scattered ray transmittance Ts of the object is generated based on a result of measurement and stored in the storage of the information derivation device according to the sixth embodiment. Hereinafter, the measurement of the primary ray transmittance Tp and the scattered ray transmittance Ts of the object depending on the body thickness distribution T of the subject H will be described.

Figure 31:
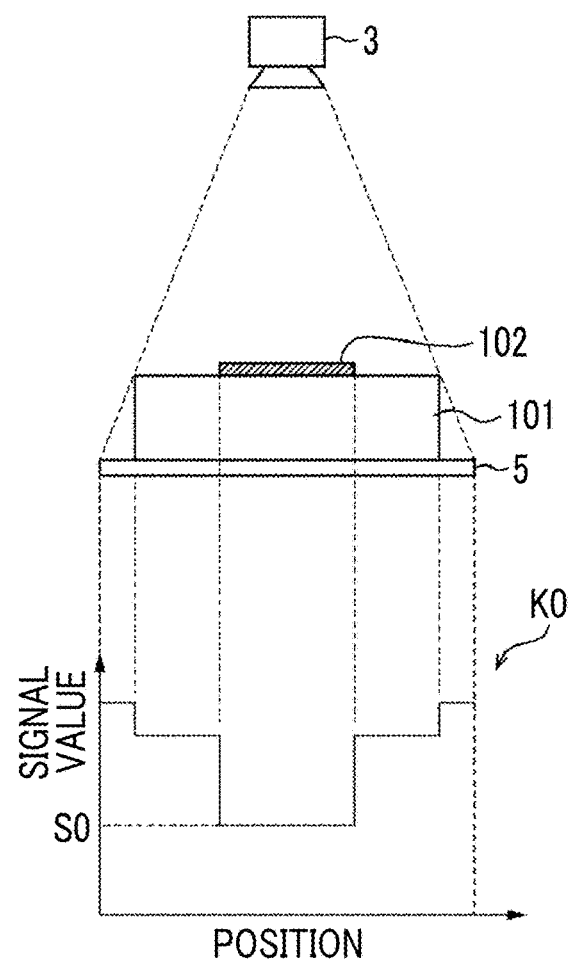
FIG. 31 is a diagram for describing measurement of a scattered ray transmittance depending on the body thickness of the subject.
Figure 32:
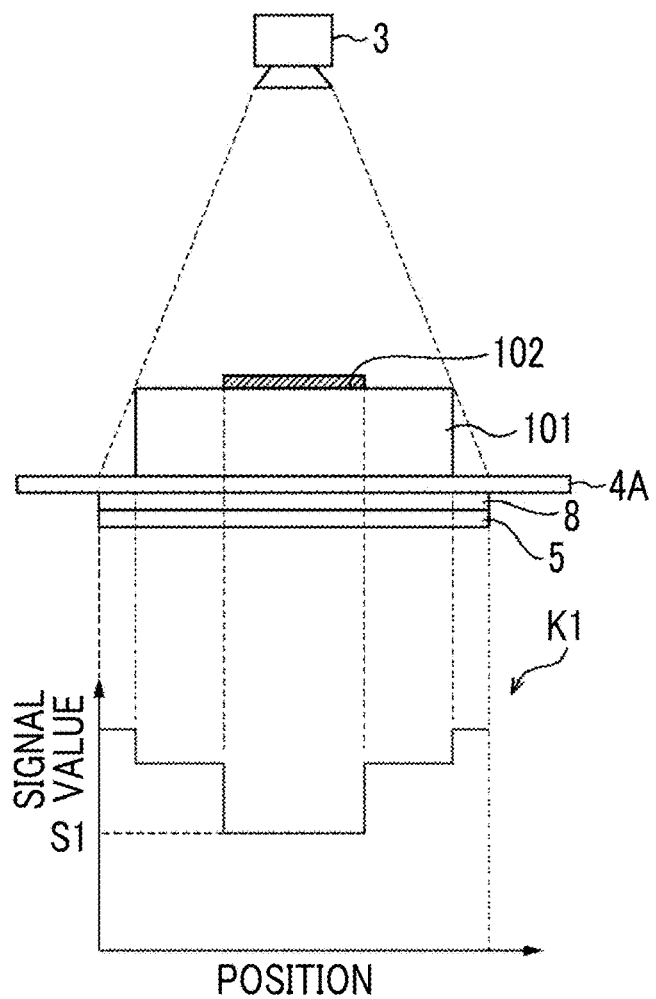
FIG. 32 is a diagram for describing the measurement of the scattered ray transmittance depending on the body thickness of the subject.

First, the calculation of the scattered ray transmittance Ts will be described. FIGS. 31 and 32 are diagrams for describing the measurement of the scattered ray transmittance Ts depending on the body thickness of the subject H. First, as shown in FIG. 31, a phantom 101 that imitates the human body is placed on a surface of the radiation detector 5, and a lead plate 102 is further placed on the phantom 101. Here, the phantom 101 has various thicknesses, such as 5 cm, 10 cm, and 20 cm, and is made of a material, such as acrylic, having a radiation transmittance similar to that of water, for example. In this state, by driving the radiation source 3 and irradiating the radiation detector 5 with the radiation, the characteristic acquisition unit 93 acquires a radiation image K0 for measurement. A signal value of the radiation image K0 is larger in the region in which the radiation is directly emitted to the radiation detector 5, and the signal value is smaller in the order of the region of the phantom 101 and the region of the lead plate 102.

Note that since the lead plate 102 does not transmit the radiation, the signal value should be 0 in a region of the lead plate 102 in the radiation image K0. However, the radiation scattered by the phantom 101 reaches a region corresponding to the lead plate 102 of the radiation detector 5. Therefore, the region of the lead plate 102 in the radiation image K0 has a signal value S0 corresponding to the scattered ray component by the phantom 101.

Next, as shown in FIG. 32, the phantom 101 is placed on the top plate 4A of the imaging apparatus 1, and the lead plate 102 is further placed on the phantom 101. Further, as in a case of imaging the subject H, the characteristic acquisition unit 93 acquires a radiation image K1 for measurement by driving the radiation source 3 to irradiate the radiation detector 5 with the radiation in a state in which the radiation detector 5 and the grid 8 are disposed below the top plate 4A. Similar to the radiation image K0, a signal value of the radiation image K1 is larger in the region in which the radiation is directly emitted to the radiation detector 5, and the signal value is smaller in the order of the region of the phantom 101 and the region of the lead plate 102. Here, as shown in FIG. 32, in a case in which imaging is performed in a state in which the top plate 4A and the grid 8 are interposed between the phantom 101 and the radiation detector 5, the radiation scattered by the top plate 4A and the grid 8 also reaches the region corresponding to the lead plate 102 of the radiation detector 5 in addition to the radiation scattered by the phantom 101. Therefore, the region of the lead plate 102 in the radiation image K1 has a signal value S1 corresponding to the scattered ray component by the phantom 101, the top plate 4A, and the grid 8.

Note that since the signal value S1 includes the scattered ray component due to the top plate 4A and the grid 8, the signal value S1 is larger than the signal value S0 shown in FIG. 31. Therefore, in a case of imaging the phantom 101 having a thickness of t, the scattered ray transmittance Ts of the object interposed between the subject H and the radiation detector 5, that is, the top plate 4A and the grid 8 can be calculated by S1/S0.

Figure 33:
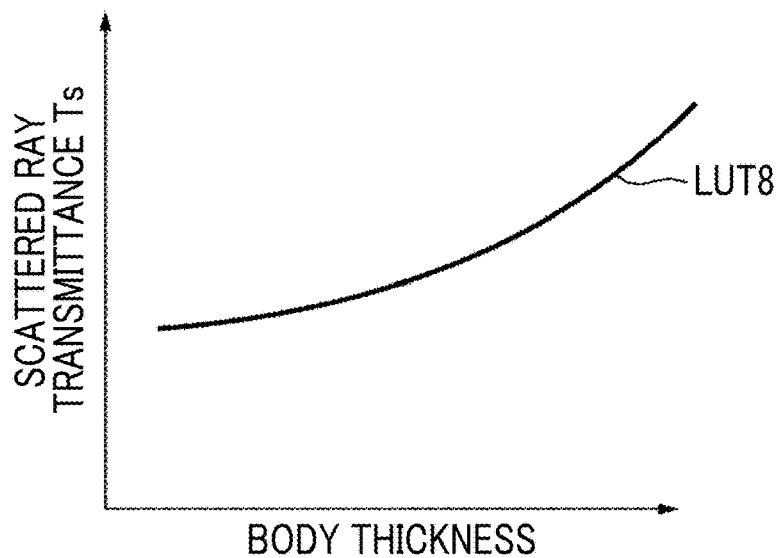
FIG. 33 is a table showing a relationship between the body thickness distribution of the subject and the scattered ray transmittance of an object interposed between the subject and a radiation detector.

In the sixth embodiment, the characteristic acquisition unit 93 calculates the scattered ray transmittance Ts corresponding to each thickness as shown in FIGS. 31 and 32 by using at least two types of phantoms having different thicknesses. In addition, the characteristic acquisition unit 93 derives the scattered ray transmittance Ts having a thickness that is not present in the phantom 101 by interpolating the scattered ray transmittance Ts for a plurality of measured thicknesses. As a result, as shown in FIG. 33, the characteristic acquisition unit 93 generates a table LUT8 that represents a relationship between the body thickness of the subject H and the scattered ray transmittance Ts of the object interposed between the subject H and the radiation detector 5 by interpolating the scattered ray transmittance for the thickness between the thicknesses.

Figure 34:
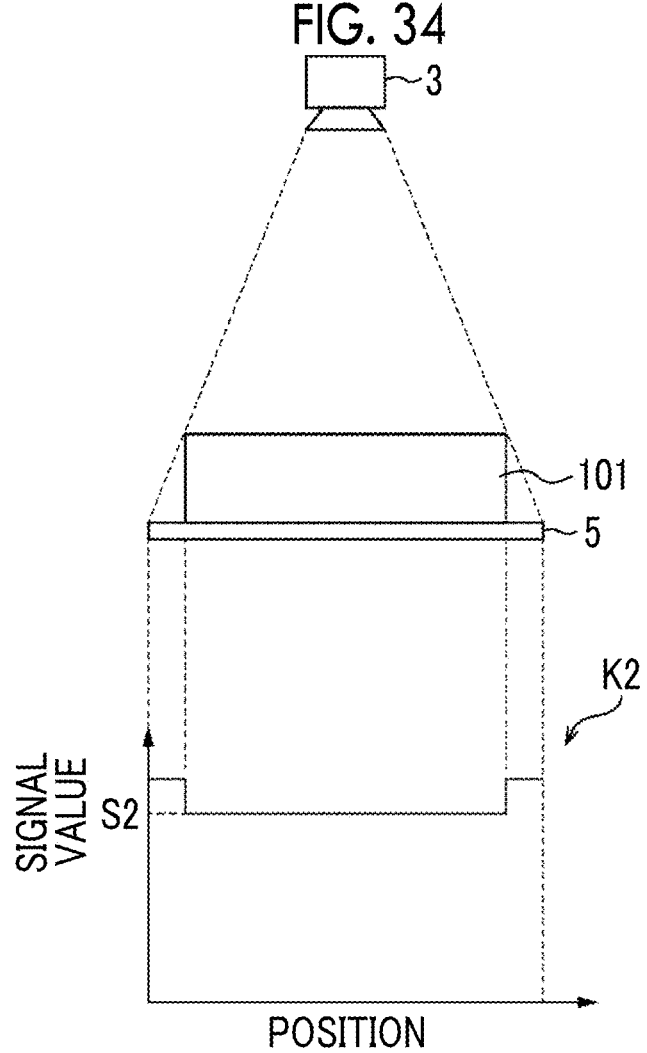
FIG. 34 is a diagram for describing measurement of a primary ray transmittance depending on the body thickness of the subject.
Figure 35:
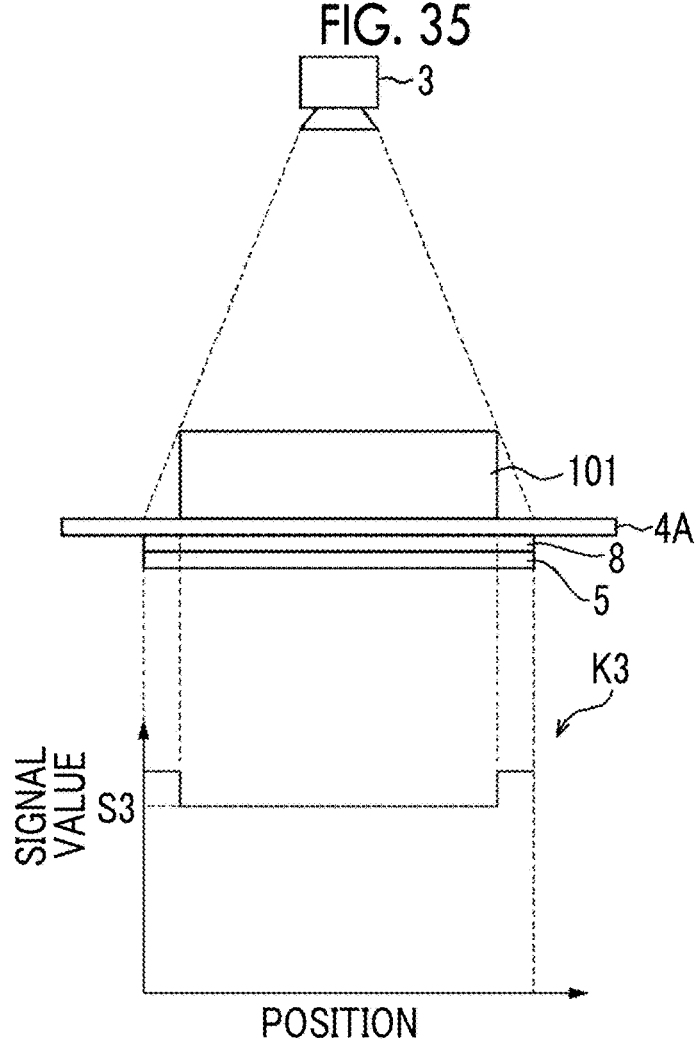
FIG. 35 is a diagram for describing the measurement of the primary ray transmittance depending on the body thickness of the subject.

Next, the calculation of the primary ray transmittance will be described. FIGS. 34 and 35 are diagrams for describing the measurement of the primary ray transmittance Tp depending on the body thickness of the subject H. First, as shown in FIG. 34, the phantom 101 that imitates the human body is placed on the surface of the radiation detector 5. Here, as the phantom 101, the same phantom as in a case in which the scattered ray transmittance Ts is derived is used. Further, in this state, by driving the radiation source 3 and irradiating the radiation detector 5 with the radiation, the characteristic acquisition unit 93 acquires a radiation image K2 for measurement. A signal value S2 in a region corresponding to the phantom 101 in the radiation image K2 includes both the primary ray component and the scattered ray component of the radiation transmitted through the phantom 101. Here, the scattered ray component of the radiation transmitted through the phantom 101 is the signal value S0 in the radiation image K0 obtained by the method shown in FIG. 31. Therefore, the primary ray component of the radiation transmitted through the phantom 101 is derived by S2−S0.

Next, as shown in FIG. 35, the phantom 101 is placed on the top plate 4A of the imaging apparatus 1, and as in a case of imaging the subject H, the characteristic acquisition unit 93 acquires a radiation image K3 for measurement by driving the radiation source 3 to irradiate the radiation detector 5 with the radiation in a state in which the radiation detector 5 and the grid 8 are disposed below the top plate 4A. A signal value S3 in a region corresponding to the phantom 101 in the radiation image K3 includes both the primary ray component and the scattered ray component of the radiation transmitted through the phantom 101, the top plate 4A, and the grid 8. Here, the scattered ray component of the radiation transmitted through the phantom 101, the top plate 4A, and the grid 8 is the signal value S1 in the radiation image K1 obtained by the method shown in FIG. 32. Therefore, the primary ray component of the radiation transmitted through the phantom 101, the top plate 4A, and the grid 8 is derived by S3−S1.

Figure 36:
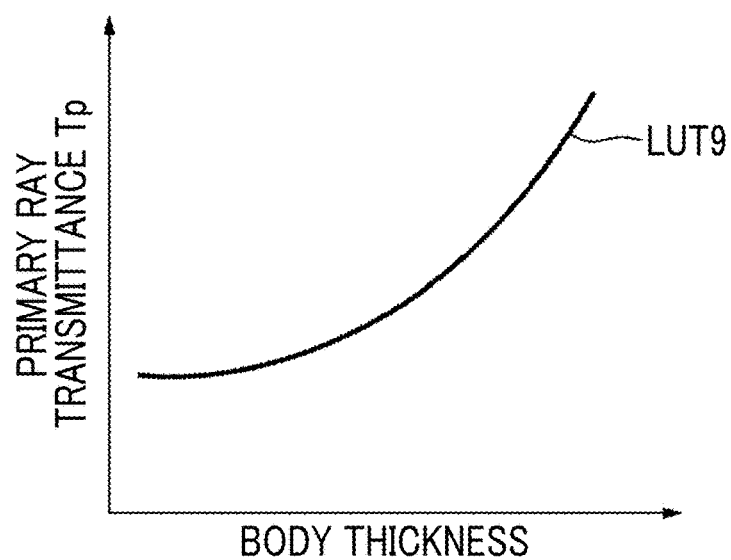
FIG. 36 is a table showing a relationship between the body thickness distribution of the subject and the primary ray transmittance of the object interposed between the subject and the radiation detector.

Therefore, it is possible to calculate, by (S3−S1)/(S2−S0), the primary ray transmittance Tp of the top plate 4A and the grid 8 interposed between the subject H and the radiation detector 5 in a case in which the phantom 101 is imaged. Further, in the sixth embodiment, the characteristic acquisition unit 93 calculates the primary ray transmittance Tp corresponding to each thickness as shown in FIGS. 34 and 35 by using at least two types of phantoms having different thicknesses. In addition, the characteristic acquisition unit 93 derives the primary ray transmittance Tp having a thickness that is not present in the phantom 101 by interpolating the primary ray transmittance Tp for a plurality of measured thicknesses. As a result, as shown in FIG. 36, the characteristic acquisition unit 93 generates a table LUT9 that represents a relationship between the body thickness of the subject H and the primary ray transmittance Tp of the object interposed between the subject H and the radiation detector 5.

The tables LUT8 and LUT9, which are generated as described above, are stored in the storage 53 of the information derivation device according to the sixth embodiment. Note that the table is generated depending on various imaging conditions (that is, the radiation quality, the dose, and the radiation source distance), and the type of grid 8 to be used, and is stored in the storage 13.

The characteristic acquisition unit 93 acquires the primary ray transmittance Tp(T0) and the scattered ray transmittance Ts(T0) corresponding to the initial body thickness distribution T0 for the object interposed between the subject H and the radiation detector 5 with reference to the tables LUT8 and LUT9 stored in the storage 53 depending on the imaging conditions acquired by the imaging condition acquisition unit 91. Note that since the primary ray transmittance Tp and the scattered ray transmittance Ts also depend on the radiation quality, the primary ray transmittance Tp and the scattered ray transmittance Ts can be represented by Tp(kV(, mmA1), T0) and Ts(kV(, mmA1), T0), respectively.

The ray distribution derivation unit 94 derives the primary ray distribution and the scattered ray distribution of the radiation detected by the radiation detector 5 by using the imaging conditions, the body thickness distribution, and the radiation characteristic of the object interposed between the subject H and the radiation detector 5. Here, a primary ray distribution Ip0 and a scattered ray distribution Is0 after being transmitted through the subject H are represented by Expression (19) and Expression (20) in a case in which the body thickness distribution is defined as T. PSF in Expression (20) is a point spread function that represents the distribution of the scattered rays spreading from one pixel, and is defined depending on the radiation quality and the body thickness. In addition, * indicates a convolution operation. The primary ray distribution Ip0 and the scattered ray distribution Is0 are derived for each pixel of the simple radiation image G0, but (x,y) are omitted in Expression (19) and Expression (20). In addition, in the sixth embodiment, derivation of the body thickness distribution, the primary ray distribution Ip0, and the scattered ray distribution Is0 is repeatedly performed as described below, but the first primary ray distribution Ip0 and the scattered ray distribution Is0 At the time of the derivation, the initial body thickness distribution T0 is used as the body thickness distribution T.

$$Ip0=I0\times\exp\{-\mu(T)\times T\} \qquad (19)$$

$$Is0=Ip0\times STPR(kV(,mmA1),T)*PSF(kV(,mmA1),T) \qquad (20)$$

Moreover, the ray distribution derivation unit 94 derives a primary ray distribution Ip1 and a scattered ray distribution Is1 reaching to the radiation detector 5 by Expression (21) and Expression (22) by using the primary ray transmittance Tp and the scattered ray transmittance Ts of the object interposed between the subject H and the radiation detector 5. Moreover, a sum Iw1 of the primary ray distribution Ip1 and the scattered ray distribution Is1 is derived by Expression (23). Also in Expression (21) and Expression (22), the initial body thickness distribution T0 is used as the body thickness distribution T in a case of first derivation of the first primary ray distribution Ip1 and the scattered ray distribution Is1.

$$Ip1=Ip0\times Tp(kV(,mmA1),T) \qquad (21)$$

$$Is1=Is0\times Ts(kV(,mmA1),T) \qquad (22)$$

$$Iw1=Ip1+Is1 \qquad (23)$$

The calculation unit 95 derives an error E2 between the sum Iw1 of the primary ray distribution Ip1 and the scattered ray distribution Is1 and the dose at each pixel position of the first radiation image G1, that is, a pixel value I1. The derivation of the error E2 is performed by Expression (24) or Expression (24-1). In Expression (24) and Expression (24-1), N represents the number of pixels of the first radiation image G1 and Σ represents a sum of all of the pixels of the first radiation image G1. Note that since in Expression (24-1), I1/Iw1 is calculated in the log, the error E2 can be derived without depending on the emitted dose to the subject H, that is, the reaching dose I0.

$$E2=(1/N)\times\Sigma\{I1-Iw1\}^2 \qquad (24)$$

$$E2=(1/N)\times\Sigma|\log\{I1/Iw1\}| \qquad (24\text{-}1)$$

Further, the calculation unit 95 updates the body thickness distribution T such that the error E2 is minimized or the error E2 is smaller than a predetermined threshold value. Further, the calculation unit 95 repeats the acquisition of the primary ray transmittance Tp and the scattered ray transmittance Ts based on the updated body thickness distribution, and the derivation of the primary ray distribution Ip1 and the scattered ray distribution Is1. Here, the calculation performed by the calculation unit 95 is referred to as a repetition calculation. In addition, in the sixth embodiment, the calculation unit 95 repeatedly performs the repetition calculation such that the error E2 is smaller than the predetermined threshold value. Further, the calculation unit 95 outputs a processed first radiation image Gc1 which has, as the pixel value, the primary ray distribution Ipc derived based on the body thickness distribution Tc of the subject H in which the error E2 is smaller than the predetermined threshold value.

Note that the characteristic acquisition unit 93 and the ray distribution derivation unit 94 perform the repetition acquisition of the primary ray transmittance Tp and the scattered ray transmittance Ts and the repetition derivation of the primary ray distribution Ip1 and the scattered ray distribution Is1, respectively.

On the other hand, for the second radiation image G2, the primary ray distribution Ipc is derived in the same manner as for the first radiation image G1. Note that the primary ray distribution for the first radiation image G1 is defined as Ipc-1, and the primary ray distribution for the second radiation image G2 is defined as Ipc-2. Then, the calculation unit 95 outputs a processed second radiation image Gc2 which has the primary ray distribution Ipc-2 as the pixel value.

In the sixth embodiment, the subtraction unit 63 derives the bone part image Gb by using the processed first and second radiation images Gc1 and Gc2. Further, the bone density derivation unit 64 derives the bone density B and the representative value of the bone density B in the target bone by using the bone part image Gb derived by the subtraction unit 63.

Note that in a case in which the simple radiation image G0 obtained by simply imaging the subject H by the imaging apparatus 1A shown in FIG. 30 is input, the learned neural network 23A constructed by performing the learning by using the bone density B derived in the sixth embodiment as the correct answer data outputs the bone density in which the object interposed between the subject H and the radiation detector is considered.

Figure 37:
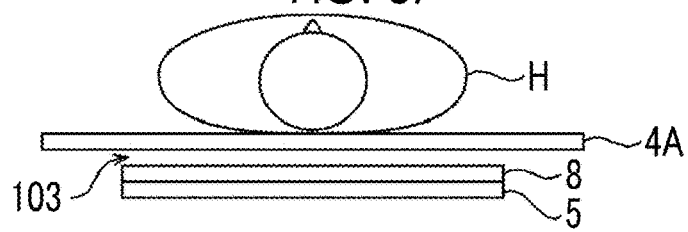
FIG. 37 is a diagram showing a state in which an air layer is interposed between a top plate and a grid.

In addition, in the sixth embodiment, the top plate 4A and the grid 8 of the imaging table 4 are used as the objects interposed between the subject H and the radiation detector 5, but as shown in FIG. 37, an air layer 103 may be interposed between the top plate 4A and the grid 8. In such a case, it is preferable that the ray distribution derivation unit 94 derive the primary ray distribution Ip1 and the scattered ray distribution Is1 by including the air layer 103 as the object interposed between the subject H and the radiation detector 5. In this case, as shown in Expression (21-1) and Expression (22-1), the primary ray distribution Ip1 and the scattered ray distribution Is1 need only be derived by performing convolution operation on a point spread function PSFair(kV(, mmA1), tair) depending on the thickness tair of the air layer 103 with respect to Expression (21) and Expression (22). Note that the thickness tair of the air layer 103 is the distance between the lower surface of the top plate 4A and the surface of the grid 8 on the subject H side.

$$Ip1 = Ip0 \times Tp(kV(,mmA1),T) * \text{PSF}_{air}(kV(,mmA1),t_{air}) \quad (21\text{-}1)$$

$$Is1 = Is0 \times Ts(kV(,mmA1),T) * \text{PSF}_{air}(kV(,mmA1),t_{air}) \quad (22\text{-}1)$$

Figure 38:
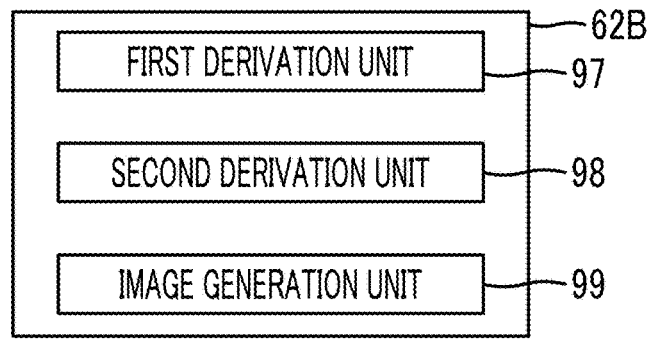
FIG. 38 is a diagram showing a functional configuration of a scattered ray removal unit of an information derivation device according to a seventh embodiment.

Then, an information derivation device according to a seventh embodiment of the present disclosure will be described. Note that a configuration of the information derivation device according to the seventh embodiment is the same as the configuration of the information derivation device according to the first embodiment, and only the processing performed by the scattered ray removal unit 62 is different, so that the detailed description will be omitted here. FIG. 38 is a diagram showing a functional configuration of the scattered ray removal unit of the information derivation device according to the seventh embodiment. As shown in FIG. 38, a scattered ray removal unit 62B of the information derivation device according to the seventh embodiment comprises a first derivation unit 97, a second derivation unit 98, and an image generation unit 99.

The information derivation device according to the seventh embodiment performs the scattered ray removal processing by causing the first derivation unit 97 to derive the first primary ray distribution and the scattered ray distribution of the radiation transmitted through the subject H by using the first and second radiation images G1 and G2, causing the second derivation unit 98 to derive the second primary ray distribution and the scattered ray distribution of the radiation transmitted through the object by using the first primary ray distribution, the scattered ray distribution, and the radiation characteristic of the object interposed between the subject H and the radiation detector that detects the radiation image, and causing the image generation unit 99 to derive the radiation images after transmission through the subject and the object by using the second primary ray distribution and the scattered ray distribution. Note that the scattered ray removal processing performed by the information derivation device according to the seventh embodiment is disclosed in WO2020/241664A. Hereinafter, the scattered ray removal processing from the first radiation image G1 will be described, but the scattered ray removal processing can also be performed on the second radiation image G2 in the same manner.

The first derivation unit 97 uses the first radiation image G1 to estimate the components (the primary ray component and the scattered ray component) of the radiation transmitted through the subject H. In derivation processing performed by the first derivation unit 97 (hereinafter referred to as first derivation processing), the "radiation transmitted through the subject H" refers to the radiation transmitted through the subject H after being transmitted through the subject H and before transmitted through the object, such as the top plate 4A and the grid 8.

Figure 39:
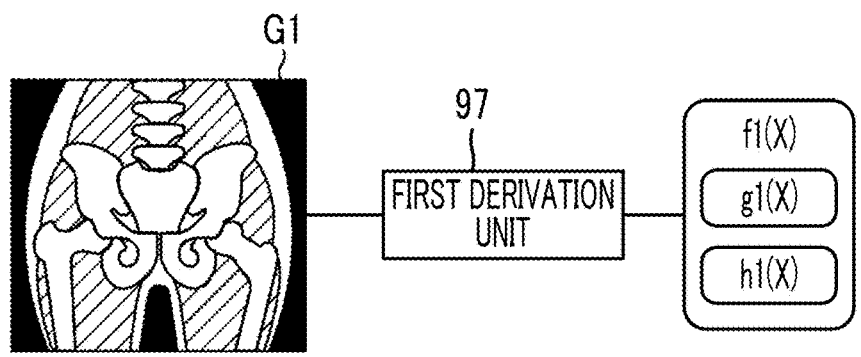
FIG. 39 is a diagram for describing a function of a first derivation unit according to the seventh embodiment.

In addition, the component of the radiation transmitted through the subject H specifically means the component of the radiation transmitted through the subject H and/or the component of the radiation scattered by the subject H. That is, the component of the radiation transmitted through the subject H is the primary ray component after being transmitted through the subject H. The component of the radiation scattered by the subject H is the scattered ray component after being transmitted through the subject H. Regarding the radiation incident on the subject H toward any position X, in a case in which the subject H is regarded as an operator g1 that generates the primary ray component and an operator h1 that generates the scattered ray component, as shown in FIG. 39, the primary ray component after being transmitted through the subject H is g1(X) and the scattered ray component after being transmitted through the subject H is h1(X).

The first derivation unit 97 uses the first radiation image G1 to estimate the primary ray component g1(X) after being transmitted through the subject H, the scattered ray component h1(X) after being transmitted through the subject H, or both the primary ray component g1(X) and the scattered ray component h1(X). In the seventh embodiment, the first derivation unit 97 uses the first radiation image G1 to estimate each of the primary ray component g1(X) after being transmitted through the subject H and the scattered ray component h1(X) after being transmitted through the subject H.

Note that in a case in which the primary ray component g1(X) after being transmitted through the subject H is estimated from the first radiation image G1, the first derivation unit 97 estimates the scattered ray component h1(X) after transmitted through the subject H by subtracting the estimated primary ray component g1(X) from the first radiation image G1. In addition, in a case in which the scattered ray component h1(X) after being transmitted through the subject H is estimated from the first radiation image G1, the first derivation unit 97 estimates the primary ray component g1(X) after transmitted through the subject H by subtracting the estimated scattered ray component h1(X) from the first radiation image G1.

The first derivation processing performed by the first derivation unit 97 can be performed by, for example, estimating the body thickness of the subject H by using the first radiation image G1, and estimating the components of the radiation transmitted through the subject H by using the estimated body thickness of the subject H. In this case, the first derivation unit 97 estimates the primary ray component g1(X) of the radiation transmitted through the subject H and the scattered ray component h1(X) of the radiation scattered by the subject H for each pixel of the first radiation image G1 (or for each predetermined compartment consisting of a plurality of pixels) based on the estimated body thickness of the subject H.

Figure 40:
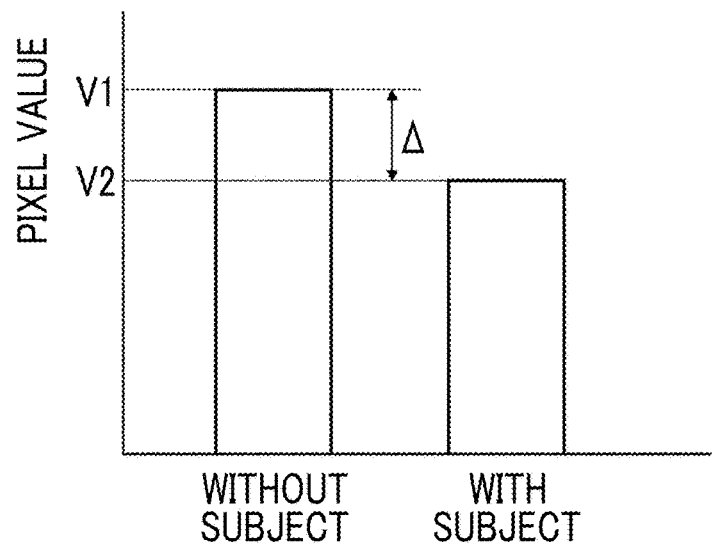
FIG. 40 is a diagram for describing a method for estimating the body thickness of the subject.

For example, as shown in FIG. 40, a pixel value V2 in a case in which the subject H is present ("with the subject") is smaller than a pixel value V1 in a case in which the subject H is not present ("without the subject"). This is due to absorption of the subject H and the like. Therefore, a difference $\Delta$ (=V1−V2) between the pixels values relates to the body thickness of the subject H. On the other hand, the pixel value V1 in a case in which the subject H is not present can be known by, such as the pixel value of the region (direct region) in which the radiation reaches the radiation detector 5 without being transmitted through the subject H, or the experiment performed in advance (imaging without the subject H). Therefore, the first derivation unit 97 can estimate the body thickness of the subject H from the pixel value V2 of the first radiation image G1 imaged with the subject H.

In addition, the primary ray component g1(X) and the scattered ray component h1(X) after being transmitted through the subject H both relate to the body thickness of the subject H. For example, as the body thickness of the subject H is thicker, the primary ray component g1(X) is smaller due to the absorption of the subject H and the like, and the scattered ray component h1(X) is larger with respect to the incident radiation. Such properties of the subject H, that is, a transmission amount and a scattering amount of the subject H with respect to the radiation having a specific energy can be obtained in advance by an experiment or the like before radiography.

For this reason, the first derivation unit 97 holds the characteristics relating to the transmission amount and the scattering amount (hereinafter, referred to as the subject scattering characteristics) in the form of a function or a table or the like, for example, for each subject H or for each imaging part of the subject H. Further, by using the energy of the radiation used for imaging and the estimated actual body thickness of the subject H to obtain the transmission amount and the scattering amount of the radiation, the primary ray component g1(X) and the scattered ray component h1(X) after being transmitted through the subject H are estimated.

Results of derivation output by the first derivation unit 97 (hereinafter referred to as the first result of derivation) are the primary ray component g1(X) after being transmitted through the subject H at a position P1, the scattered ray component h1(X) after being transmitted through the subject H at the position P1, or an intensity distribution f1(X) of the radiation after being transmitted through the subject H at the position P1. The intensity distribution f1(X) of the radiation at the position P1 is, for example, the sum or weighted sum of the primary ray component g1(X) and the scattered ray component h1(X). In the seventh embodiment, the first derivation unit 97 outputs the intensity distribution f1(X) of the radiation after being transmitted through the subject H at the position P1 as a first result of derivation in the form of an image or the form of a collection of data capable of constructing an image, for example. Note that the first derivation unit 97 can also output one of the primary ray component g1(X) or the scattered ray component h1(X) after being transmitted through the subject H as the result of derivation.

The second derivation unit 98 estimates the components of the radiation transmitted through the object by using the result of derivation of the first derivation unit 97 and the scattering characteristics of the object through which the radiation transmitted through the subject H is further transmitted, such as the top plate 4A and the grid 8. In derivation processing of the second derivation unit 98 (hereinafter referred to as second derivation processing), "transmitted through the object" means that the radiation is transmitted through a certain position in which the subject H is present and then transmitted through the object. Therefore, depending on a specific shape of the subject H, the radiation is directly transmitted through the object without being transmitted through the subject H.

Specifically, the second derivation unit 98 estimates the component of the radiation transmitted through the subject H and the object, or the component of the radiation scattered by at least one of the subject H or the object. The component of the radiation transmitted through the subject H and the object is the primary ray component after being transmitted through the object. The radiation component scattered by at least one of the subject H or the object is the scattered ray component after being transmitted through the object.

The scattering characteristics of the object determine the distribution of the radiation doses transmitted through the object and/or the radiation dose scattered by the object. In the seventh embodiment, a scattering characteristic f2(X) including a first characteristic g2(X) that determines the distribution of the radiation doses transmitted through the object and a second characteristic h2(X) that determines the distribution of the radiation doses scattered by the object is used. Specifically, the scattering characteristic f2(X) is the sum or weighted sum of the first characteristic g2(X) and the second characteristic h2(X), for example, f2(X)=g2(X)+h2(X).

The first characteristic g2(X) is a function or a table or the like that determines the transmitted dose of the radiation directly incident on the object toward any position X without being transmitted through the subject H. In addition, the second characteristic h2(X) is a function or a table or the like that determines the transmitted dose of the radiation directly incident on the object toward any position X without being transmitted through the subject H. For example, in a case in which the object is only the top plate 4A of the imaging table 4, the first characteristic g2(X) determines the distribution of the transmitted doses of the top plate 4A, and the second characteristic h2(X) determines the distribution of the scattered ray doses of the top plate 4A. A state of a specific configuration of the object (use or non-use of the imaging table 4 or the like) is known before radiography. Therefore, the first characteristic g2(X) and the second characteristic h2(X) can be obtained in advance by experiments or the like, for example, for each specific configuration of the object or for each combination of the objects. In addition, in a case in which the object is regarded to generate the primary ray component and the scattered ray component from the incident radiation, the first characteristic g2(X) is the operator that generates the primary ray component depending on the incident radiation, and the second characteristic h2(X) is the operator that generates the scattered ray component depending on the incident radiation.

In the seventh embodiment, the second derivation unit 98 holds the first characteristic g2(X) and the second characteristic h2(X) in advance for each specific configuration of the object, for example. As a result, the second derivation unit 98 holds the scattering characteristic f2(X) of the object in advance. Note that the second derivation unit 98 can acquire the first characteristic g2(X), the second characteristic h2(X), and/or the scattering characteristic f2(X), as needed.

Figure 41:
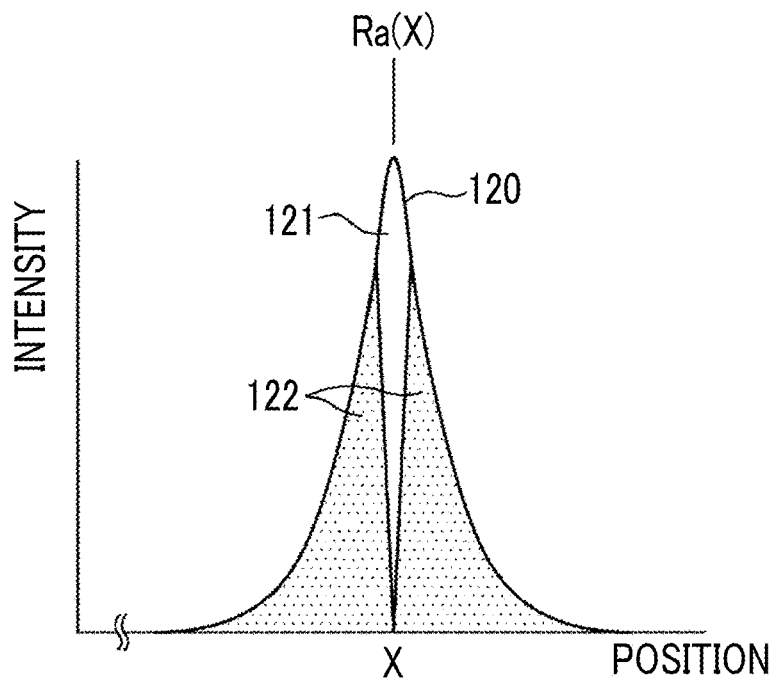
FIG. 41 is a diagram showing a point spread function.

As shown in FIG. 41, the intensity distribution after the radiation (X) incident toward any point X0 is transmitted through the object can be approximated by a point spread function (PSF) 120. For example, the PSF 120 is a Gaussian function. Further, of the radiation (X) incident on the object toward any point X0, the component reaching any point X0 and its vicinity is a distribution 121 of the primary ray component, and a portion excluding the distribution 121 of the primary ray component from the PSF 120 is a distribution 122 of the scattered ray component.

Moreover, since the energy of the radiation used for imaging, the material (density and the like), and the thickness (mass) of the top plate 4A, which is the object, are known, the specific shape of the PSF 120, such as peak height and full width at half maximum, is predetermined. Therefore, for example, the second characteristic h2(X) can be obtained in advance by performing a deconvolution operation of the distribution 122 of the scattered ray component on the radiation image obtained by performing imaging without the subject H. In addition, the first characteristic g2(X) can be obtained in advance by subtracting the second characteristic h2(X) from the radiation image obtained by performing imaging without the subject H, or by performing the deconvolution operation of the distribution 121 of the primary ray component.

The second derivation unit 98 estimates the component of the radiation transmitted through the object by applying the scattering characteristic of the object to the first result of derivation which is the result of derivation of the first derivation unit 97. Specifically, the object receives the incidence of the radiation of the distribution represented by the first result of derivation. Therefore, the second derivation unit 98 estimates the component of the radiation transmitted through the object by setting an argument of the scattering characteristic f2(X) of the object as the first result of derivation (f1(X)). That is, the second derivation unit 98 estimates the component of the radiation transmitted through the object by the calculation based on Expression (25). In the seventh embodiment, since the first result of derivation is f1(X)=g1(X)+h1(X), Expression (25) can be represented as Expression (26), and can be expanded as in Expression (27).

$$f2(f1(X))=g2(f1(X))+h2(f1(X)) \quad (25)$$

$$f2(f1(X))=g2(g1(X)+h1(X))+h2(g1(X)+h1(X)) \quad (26)$$

$$f2(f1(X))=g2g1(X)+g2h1(X)+h2g1(X)+h2h1(X) \quad (27)$$

Figure 42:
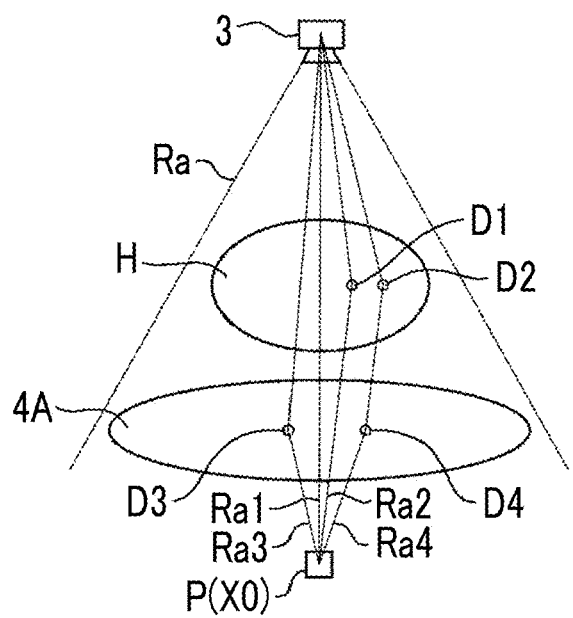
FIG. 42 is a diagram showing a radiation path.

As shown in FIG. 42, the first term "g2g1(X)" on the right side of Expression (27) represents radiation Ra1 of the radiation used for imaging, which is transmitted through the subject H and transmitted through the object (top plate 4A in FIG. 42), and then reaches a pixel P(X0) at any point X0. The second term "g2h1(X)" on the right side of Expression (27) represents radiation Ra2 of the radiation used for imaging, which is scattered by a scattering body D1 included in the subject H and then is transmitted through the object to reach the pixel P(X0) at any point X0. The third term "h2g1(X)" on the right side of Expression (27) represents radiation Ra3 of the radiation used for imaging, which is transmitted through the subject H and then is scattered by a scattering body D3 included in the object to reach the pixel P(X0) at any point X0. In addition, the fourth term "h2h1(X)" on the right side of Expression (27) represents radiation Ra4 of the radiation used for imaging, which is scattered by a scattering body D2 included in the subject H and then is further scattered by a scattering body D4 included in the object to reach the pixel P(X0) at any point X0.

As described above, the second derivation unit 98 obtains the first term "g2g1(X)" of Expression (27) and/or the sum of the second to fourth terms "g2h1(X)+h2g1(X)+h2h1(X)". This is because the first term "g2g1(X)" of Expression (27) represents the distribution of the primary ray components after being transmitted through the object, and the sum of the second to fourth terms "g2h1(X)+h2g1(X)+h2h1(X)" represents the distribution of the scattered ray components after being transmitted through the object. In the seventh embodiment, the second derivation unit 98 obtains the distribution g2g1(X) of the primary ray components after being transmitted through the object, and outputs the obtained distribution g2g1(X) as the result of derivation.

The image generation unit 99 uses the result of derivation of the second derivation unit 98 to generate the processed radiation image that forms the image of the subject H by the radiation transmitted through the subject H and the object. In a case in which the second derivation unit 98 estimates the primary ray component of the radiation transmitted through the subject H and the object, the image generation unit 99 images a second result of derivation, which is the result of derivation of the second derivation unit 98, to generate the processed radiation image. In addition, in a case in which the second derivation unit 98 estimates the scattered ray component of the radiation scattered by the subject H or the object, the image generation unit 99 subtracts the second result of derivation, which is the result of derivation of the second derivation unit 98, from the first radiation image G1 to generate the processed radiation image.

In the seventh embodiment, since the second derivation unit 98 outputs the distribution of the primary ray component after being transmitted through the object, the image generation unit 99 generates the processed radiation image by imaging the output distribution of the primary ray component. Therefore, the distribution g2g1(X) of the primary ray component output by the second derivation unit 98 is the processed radiation image in which the scattered ray component is substantially removed. Note that the image generation unit 99 can perform various pieces of image processing (for example, contrast adjustment processing or structure emphasis processing) on the generated processed radiation image, as needed.

Note that the scattered ray removal processing according to the sixth and seventh embodiments may be performed in the first to fifth embodiments. In this case, the information derivation devices 50A to 50D include the scattered ray removal unit 62A or the scattered ray removal unit 62B instead of the scattered ray removal unit 62.

Figure 43:
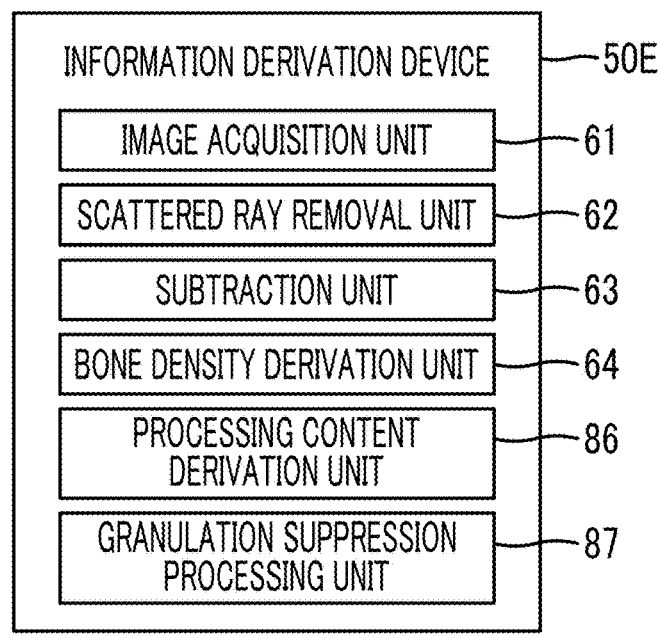
FIG. 43 is a diagram showing a functional configuration of an information derivation device according to an eighth embodiment.

Then, an eighth embodiment of the present disclosure will be described. FIG. 43 is a diagram showing a functional configuration of an information derivation device according to the eighth embodiment. Note that in FIG. 43, the same reference numerals are assigned to the same configurations as those in FIG. 7, and the detailed description thereof will be omitted. In the seventh embodiment of the present disclosure, the first and second radiation images G1 and G2 are subjected to granulation suppression processing, and the energy subtraction processing is performed by using the first and second radiation images G1 and G2 to which the granulation suppression processing is performed. Therefore, as shown in FIG. 43, an information derivation device 50E according to the eighth embodiment further comprises a processing content derivation unit 86 and a granulation suppression processing unit 87 with respect to the information derivation device 50 according to the first embodiment.

The processing content derivation unit 86 derives a processing content of first granulation suppression processing on the first radiation image G1, and derives a processing content of second granulation suppression processing on the second radiation image G2 based on the processing content of the first granulation suppression processing.

Here, in the present embodiment, the subject H is imaged by the one-shot method to acquire the first and second radiation images G1 and G2. In the case of the one-shot method, the radiation transmitted through the subject H is emitted to the two radiation detectors 5 and 6 stacked with the radiation energy conversion filter 7 interposed therebetween. Therefore, the emitted dose of the second radiation detector 6 on the side away from the radiation source 3 is smaller than that of the first radiation detector 5 on the side closer to the radiation source 3. As a result, the second radiation image G2 has more radiation quantum noise and lower S/N than the first radiation image G1. Therefore, particularly for the second radiation image G2, it is necessary to perform the granulation suppression processing of suppressing granulation caused by quantum noise.

The processing content derivation unit 86 derives the processing content of the first granulation suppression processing on the first radiation image G1 having higher S/N among the first radiation image G1 and the second radiation image G2. Further, the processing content derivation unit 86 derives the processing content of the second granulation suppression processing on the second radiation image G2 based on the processing content of the first granulation suppression processing. Hereinafter, the derivation of the processing content will be described.

Examples of the granulation suppression processing include filtering processing by using a smoothing filter, such as a Gaussian filter, having a predetermined size such as 3×3 or 5×5 centered on an attention pixel. However, in a case in which the Gaussian filter is used, the edges of the structures included in the first and second radiation images G1 and G2 may be blurred. Therefore, in the eighth embodiment, the granulation suppression processing is performed by using an edge storage smoothing filter that suppresses the granulation while preventing edge blurriness. As the edge storage smoothing filter, a bilateral filter, which weights the normal distribution in which the weight of the pixel adjacent to the attention pixel is smaller as the distance from the attention pixel is larger, and the weight is reduced as the difference in the pixel value from the attention pixel is larger, is used.

Figure 44:
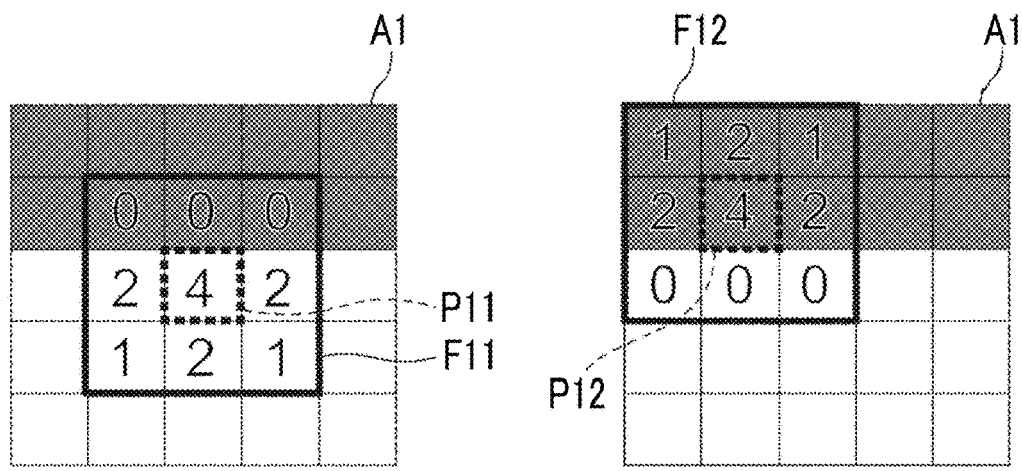
FIG. 44 is a diagram showing a bilateral filter for a first radiation image.

FIG. 44 is a diagram showing an example of the bilateral filter on the first radiation image G1. Note that FIG. 44 shows two local regions A1 having 5×5 pixels in the vicinity of the edge included in the first radiation image G1 side by side. In addition, the two local regions A1 shown in FIG. 44 are the same, but the positions of the attention pixels are different from each other. In the local region A1 on the left side of FIG. 44, the low-concentration pixel in contact with the boundary of the edge is an attention pixel P11. As described above, the bilateral filter weights the normal distribution in which the weight of the pixel adjacent to the attention pixel is smaller as the distance from the attention pixel is larger, and the weight is reduced as the difference in the pixel value from the attention pixel is larger.

Therefore, the processing content derivation unit 86 determines a filter size of the bilateral filter based on the difference between the pixel value of the attention pixel and the pixel value of the pixels around the attention pixel. For example, as the difference between the pixel value of the attention pixel and the pixel value around the attention pixel is smaller, the filter size is larger. In addition, the processing content derivation unit 86 determines the weight of the bilateral filter based on the difference between the pixel value of the attention pixel and the pixel value of the pixels around the attention pixel. For example, as the difference between the pixel value of the attention pixel and the pixel value around the attention pixel is smaller, the weight of the pixel closer to the attention pixel is larger than the weight of the pixel away from the attention pixel.

As a result, the processing content derivation unit 86 derives a 3×3 bilateral filter F11 having a weight as shown on the left side of FIG. 44 for the attention pixel P11 in the local region A1 on the left side of FIG. 44 as the processing content of the first granulation suppression processing.

In the local region A1 on the right side of FIG. 44, the high-concentration pixel in contact with the boundary of the edge is an attention pixel P12. Therefore, the processing content derivation unit 86 derives a 3×3 bilateral filter F12 having a weight as shown on the right side of FIG. 44 for the attention pixel P12 in the local region A1 on the right side of FIG. 44 as the processing content of the first granulation suppression processing.

Figure 45:
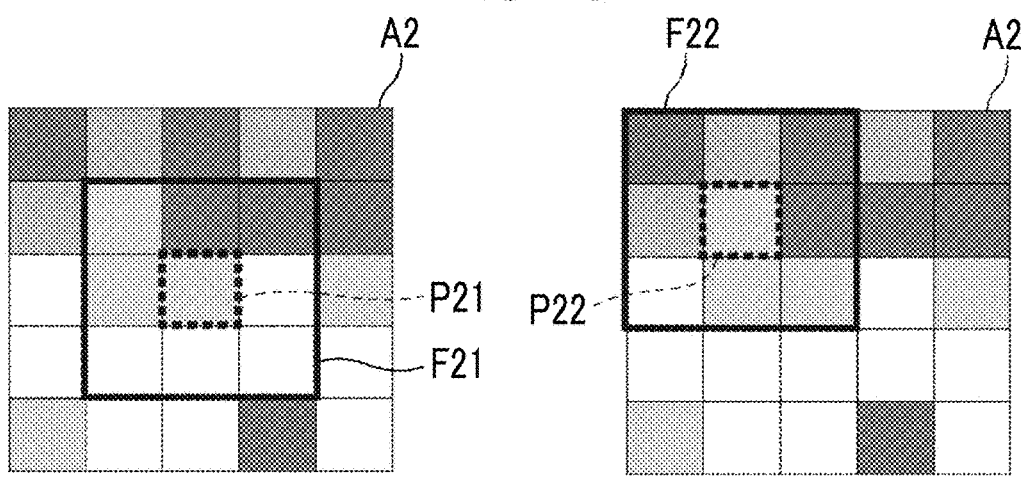
FIG. 45 is a diagram showing a local region of a second radiation image corresponding to a local region of the first radiation image shown in FIG. 44.

FIG. 45 is a diagram showing a local region A2 of the second radiation image corresponding to the local region A1 of the first radiation image shown in FIG. 44. Note that FIG. 45 shows the local region A2 having 5×5 pixels in the vicinity of the edge included in the second radiation image G2. The local region A2 is a region at the same position as the local region A1 in the first radiation image G1 shown in FIG. 44. Two local regions A2 shown in FIG. 45 are the same, but the positions of the attention pixels are different from each other. In the local region A2 on the left side of FIG. 45, the pixel corresponding to the attention pixel P11 shown in the local region A1 on the left side of FIG. 44 is an attention pixel P21. In the local region A2 on the right side of FIG. 45, the pixel corresponding to the attention pixel P12 shown in the local region A1 on the right side of FIG. 44 is an attention pixel P22.

Here, the dose of the radiation emitted to the second radiation detector 6 from which the second radiation image G2 is acquired is lower than the dose of the radiation emitted to the first radiation detector 5 from which the first radiation image G1 is acquired. Therefore, the second radiation image G2 has more radiation quantum noise than the first radiation image G1 and has poor granulation, so that the edges do not clearly appear. In addition, due to the influence of the quantum noise, the low-concentration pixels may be included in the high-concentration region in the vicinity of the boundary of the edge, or the high-concentration pixels may be included in the low-concentration region. Therefore, from the second radiation image G2, it is not possible to appropriately determine the bilateral filter that suppresses granulation while storing the edges, unlike the first radiation image G1.

In this case, it is conceivable to use the smoothing filter, such as the Gaussian filter. However, in a case in which the smoothing filter is used, it is not possible to achieve both noise suppression and edge storage, and as a result, the edges are buried in the noise, and the edges of the structure included in the second radiation image G2 cannot be restored.

Therefore, in the eighth embodiment, the processing content derivation unit 86 derives the processing content of second granulation suppression processing on the second radiation image based on the processing content of the first granulation suppression processing on the first radiation image G1. That is, the processing content derivation unit 86 derives the processing content of the second granulation suppression processing such that the processing content of the second granulation suppression processing performed on each pixel of the second radiation image G2 is the same as the processing content of the first granulation suppression processing performed on the pixel of the first radiation image G1 corresponding to each pixel of the second radiation image G2. Specifically, the processing content derivation unit 86 derives the bilateral filter having the same size and the same weight as the bilateral filter determined for each pixel of the first radiation image G1 as the processing content of the second granulation suppression processing on the second radiation image G2.

Figure 46:
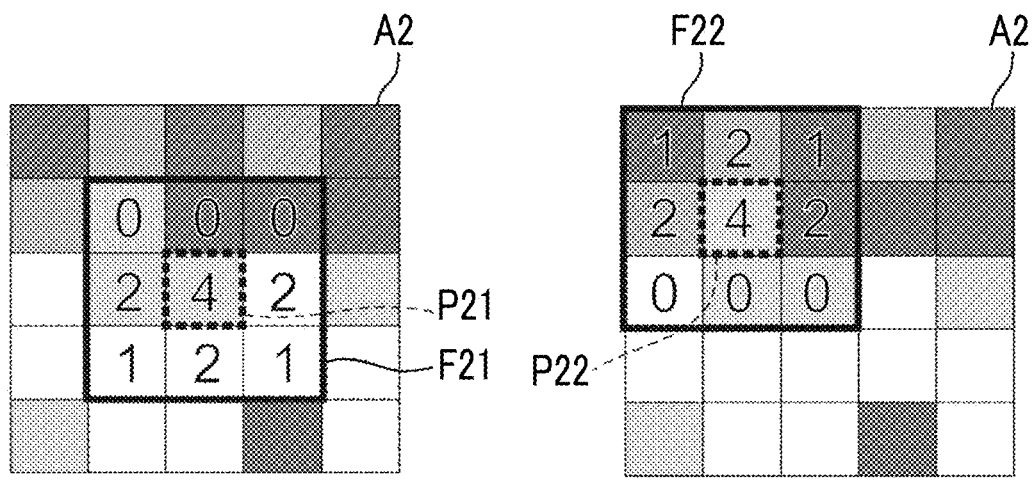
FIG. 46 a diagram showing an example of a bilateral filter for a second radiation image.

FIG. 46 a diagram showing an example of the bilateral filter for the second radiation image G2. Note that FIG. 46 shows the local region A2 having 5×5 pixels in the vicinity of the edge included in the second radiation image G2, as in FIG. 44. As shown in FIG. 46, the processing content derivation unit 86 derives a bilateral filter F21 having the same size and the same weight as the bilateral filter F11 derived for the attention pixel P11 of the local region A1 of the first radiation image G1 as the processing content of the second granulation suppression processing, for the attention pixel P21 of the local region A2 of the second radiation image G2.

In addition, the processing content derivation unit 86 derives a bilateral filter F22 having the same size and the same weight as the bilateral filter F12 derived for the attention pixel P12 of the local region A1 of the first radiation image G1 as the processing content of the second granulation suppression processing, for the attention pixel P22 of the local region A2 of the second radiation image G2.

Note that the processing content of the second granulation suppression processing is derived, it is necessary to associate the pixel positions of the first radiation image G1 and the second radiation image G2 with each other. Therefore, it is preferable to perform registration of the first radiation image G1 and the second radiation image G2.

The granulation suppression processing unit 87 performs the granulation suppression processing on the first radiation image G1 and the second radiation image G2. That is, the granulation suppression processing is performed on the first radiation image G1 and the second radiation image G2 based on the processing content derived by the processing content derivation unit 86. Specifically, the first radiation image G1 is subjected to the filtering processing by the bilateral filter derived for the first radiation image G1. In addition, the second radiation image G2 is subjected to the filtering processing by the bilateral filter derived based on the first radiation image G1.

In the eighth embodiment, the subtraction unit 63 derives the bone part image Gb by Expression (1) by using the first and second radiation images G1 and G2 that are subjected to the granulation suppression processing. Further, the bone density derivation unit 64 derives the bone density B and the representative value of the bone density B in the target bone.

Figure 47:
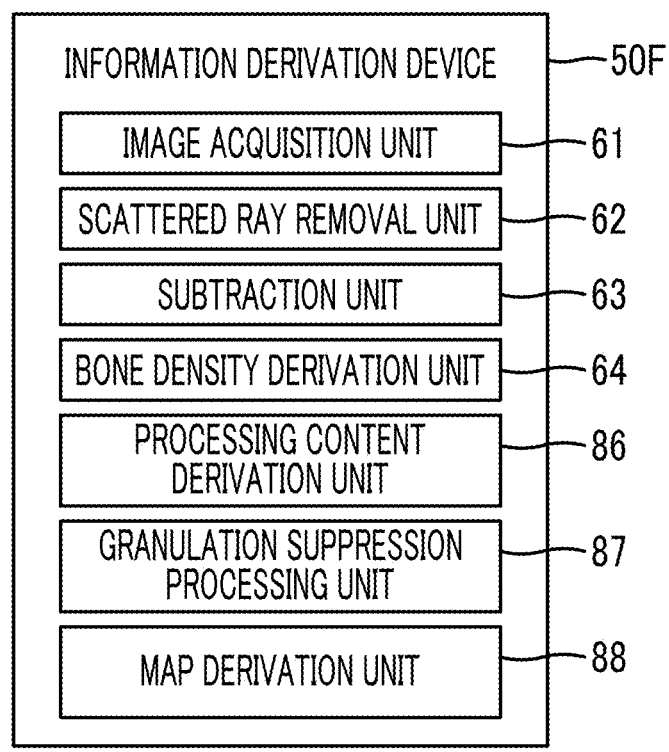
FIG. 47 is a diagram showing a functional configuration of an information derivation device according to a ninth embodiment.

Then, a ninth embodiment of the present disclosure will be described. FIG. 47 is a diagram showing a functional configuration of an information derivation device according to the ninth embodiment. Note that in FIG. 47, the same reference numerals are assigned to the same configurations as those in FIG. 43, and the detailed description thereof will be omitted. An information derivation device 50F according to the ninth embodiment of the present disclosure further comprises a map derivation unit 88 that derives a physical quantity map of the subject H based on at least one of the first radiation image G1 or the second radiation image G2 with respect to the information derivation device 50E according to the eighth embodiment, and is different from the eighth embodiment in that the processing content derivation unit 86 derives the processing content of the second granulation suppression processing on the second radiation image G2 based on the physical quantity map.

The map derivation unit 88 derives the physical quantity map for the subject H. Examples of the physical quantity include the body thickness and the bone density of the subject H. As the body thickness, the body thickness distribution in a case in which the scattered ray removal unit 62 satisfies the termination condition can be used. As the bone density, the bone density derived by the bone density derivation unit 64 can be used.

Here, the contrasts of the structures included in the first and second radiation images G1 and G2, which are the targets of the granulation suppression processing, vary depending on the imaging conditions. Therefore, in a case in which the edge storage smoothing processing is performed by using the bilateral filter, it is necessary to control the intensity of the edge to be stored depending on the imaging conditions. On the other hand, in a body thickness map representing the body thickness of the subject H, the contrast of the structure included in the map is represented by the thickness (mm) that does not depend on the imaging conditions.

Figure 48:
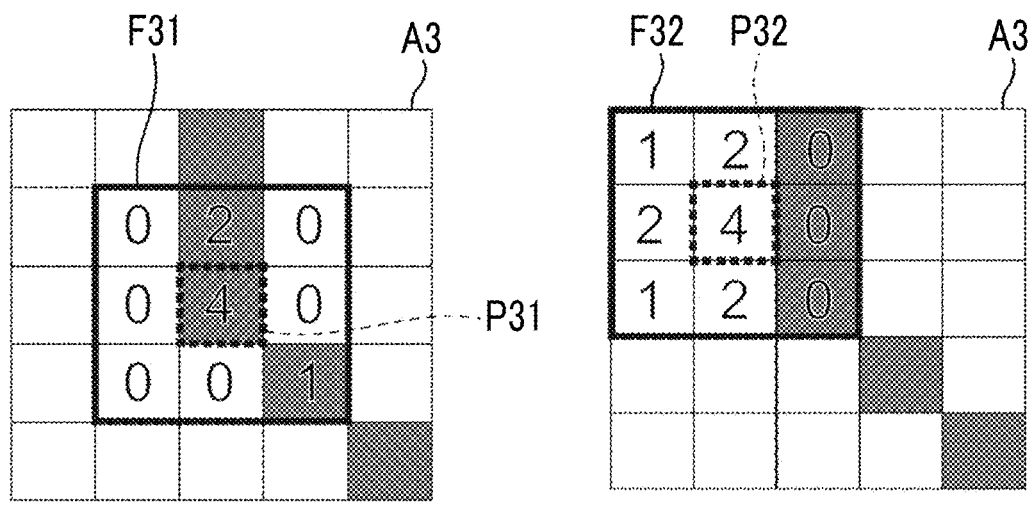
FIG. 48 is a diagram showing an example of a bilateral filter for a physical quantity map.

Therefore, in the ninth embodiment, the processing content derivation unit 86 derives the processing content of the first granulation suppression processing on the first radiation image G1 based on the physical quantity map. FIG. 48 is a diagram showing an example of the bilateral filter for the physical quantity map. Note that FIG. 48 shows two 5×5 pixel local regions A3 in the vicinity of the edges included in the physical quantity map side by side. The two local regions A3 shown in FIG. 48 are the same, but the positions of the attention pixels are different from each other. In the local region A3 on the left side of FIG. 48, the high-concentration pixel on the edge is an attention pixel P31. Therefore, for the attention pixel P31 in the local region A3 on the left side of FIG. 48, a 3×3 bilateral filter F31 having the weight as shown on the left side of FIG. 48 is derived as the processing content of the first granulation suppression processing.

In the local region A3 on the right side of FIG. 48, the low-concentration pixel in contact with the boundary of the edge is an attention pixel P32. Therefore, for the attention pixel P32 in the local region A3 on the right side of FIG. 48, a 3×3 bilateral filter F32 having the weight as shown on the right side of FIG. 48 is derived as the processing content of the first granulation suppression processing.

Also in the ninth embodiment, the processing content derivation unit 86 derives the bilateral filter having the same bilateral filter determined for each pixel of the first radiation image G1 as the processing content of the second granulation suppression processing on the second radiation image G2. That is, in the local region of the second radiation image G2 corresponding to the local region A3 of the first radiation image G1, for the pixel corresponding to the attention pixel P31 in the local region A3, the bilateral filter having the same size and the same weight as the bilateral filter F31 is derived as the processing content of the second granulation suppression processing. In addition, for the pixel of the second radiation image G2 corresponding to the attention pixel P32 of the local region A3 of the first radiation image G1, the bilateral filter having the same size and the same weight as the bilateral filter F32 is derived as the processing content of the second granulation suppression processing.

Further, in the ninth embodiment, the granulation suppression processing is performed on the first radiation image G1 and the second radiation image G2 based on the processing content derived by the processing content derivation unit 86 by the granulation suppression processing unit 87. The subtraction unit 63 derives the bone part image Gb by Expression (1) by using the first and second radiation images G1 and G2 that are subjected to the granulation suppression processing. Further, the bone density derivation unit 64 derives the bone density B and the representative value of the bone density B in the target bone.

Note that the granulation suppression processing performed in the eighth and ninth embodiments may be performed in the first to seventh embodiments.

In addition, in each of the embodiments described above, the bone density of the simple radiation image G0 is estimated as the information relating to the bone density, but the present disclosure is not limited to this. For example, the evaluation value of the fracture risk may be derived as the result of estimation relating to the bone density. Hereinafter, this case will be described as a tenth embodiment. For the derivation of the evaluation value of the fracture risk, for example, a method disclosed in WO2020/166561A can be used.

Figure 49:
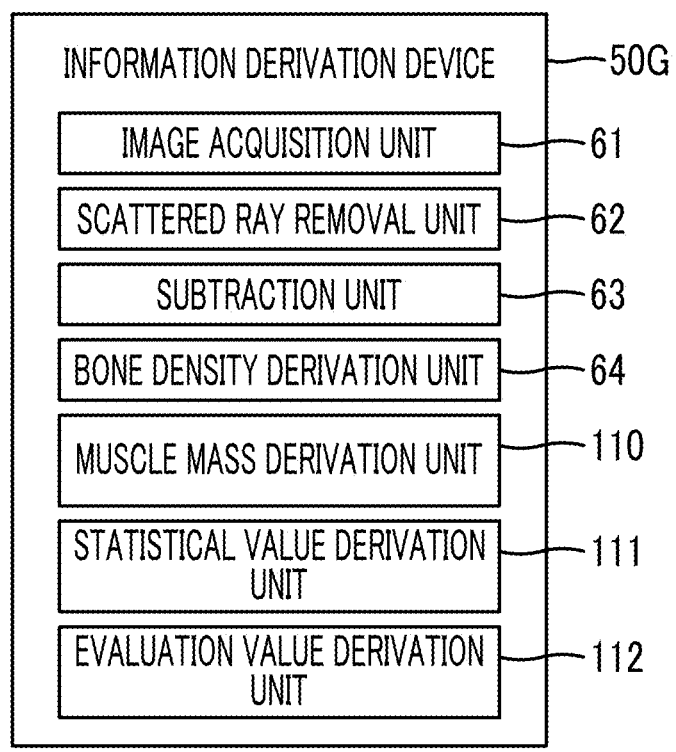
FIG. 49 is a diagram showing a functional configuration of an information derivation device according to a tenth embodiment.

FIG. 49 is a diagram showing a functional configuration of an information derivation device according to the tenth embodiment. Note that in FIG. 49, the same reference numerals are assigned to the same configurations as those in FIG. 7, and the detailed description thereof will be omitted. In the tenth embodiment of the present disclosure, instead of the derivation of the bone density as the correct answer data 42, the evaluation value of the fracture risk is derived. Therefore, as shown in FIG. 49, an information derivation device 50G according to the tenth embodiment further comprises a muscle mass derivation unit 110, a statistical value derivation unit 111, and an evaluation value derivation unit 112 with respect to the information derivation device 50 according to the first embodiment.

Note that the subtraction unit 63 of the information derivation device 50G according to the tenth embodiment derives a soft part image Gs obtained by extracting the soft tissue of the subject H from the first and second radiation images G1 and G2 in addition to the bone part image Gb. The soft part image Gs is derived by Expression (28). In Expression (25), β is a weighting coefficient for extracting the soft tissue.

$$Gs(x,y)=G1(x,y)-\beta \times G2(x,y) \quad (28)$$

The muscle mass derivation unit 110 derives the muscle mass for each pixel in the soft region in the soft part image Gs based on the pixel value. The soft tissue includes the muscle tissue, the fat tissue, the blood, and the water. In the muscle mass derivation unit 110 according to the tenth embodiment, a tissue other than the fat tissue in the soft tissue is regarded as the muscle tissue. That is, in the muscle mass derivation unit 110 according to the tenth embodiment, a non-fat tissue including the blood and the water in the muscle tissue is handled as the muscle tissue.

Figure 50:
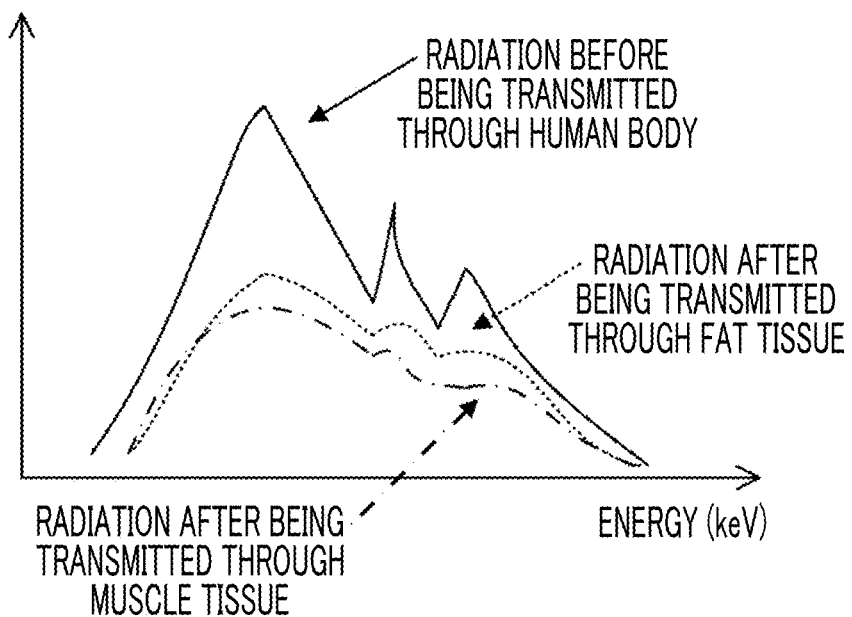
FIG. 50 is a diagram showing an example of energy spectra of the radiation after being transmitted through a muscle tissue and radiation after being transmitted through a fat tissue.

The muscle mass derivation unit 110 separates the muscle and the fat from the soft part image Gs by using a difference in an energy characteristic between the muscle tissue and the fat tissue. As shown in FIG. 50, the dose of the radiation after being transmitted through the subject H is lower than the dose of the radiation before being incident on the subject H, which is a human body. In addition, since the energy absorbed by the muscle tissue and the energy absorbed by the fat tissue is different and attenuation coefficients are different, the energy spectra of the radiation after being transmitted through the muscle tissue and the radiation after being transmitted through the fat tissue in the radiation after being transmitted through the subject H are different. As shown in FIG. 50, the energy spectrum of the radiation transmitted through the subject H and emitted to each of the first radiation detector 5 and the second radiation detector 6 depends on a body composition of the subject H, specifically, a ratio between the muscle tissue and the fat tissue. Since the fat tissue is more likely to transmit the radiation than the muscle tissue, the dose of the radiation after being transmitted through the human body is smaller in a case in which the ratio of the muscle tissue is larger than the ratio of the fat tissue.

Therefore, the muscle mass derivation unit 110 separates the muscle and the fat from the soft part image Gs by using the difference in the energy characteristic between the muscle tissue and the fat tissue described above. That is, the muscle mass derivation unit 110 generates a muscle image from the soft part image Gs. In addition, the muscle mass derivation unit 110 derives the muscle mass of each pixel based on the pixel value of the muscle image.

Note that a specific method by which the muscle mass derivation unit 110 separates the muscle and the fat from the soft part image Gs is not limited, but as an example, the muscle mass derivation unit 110 according to the tenth embodiment generates the muscle image from the soft part image Gs by Expression (29) and Expression (30). Specifically, first, the muscle mass derivation unit 110 derives a muscle ratio rm(x,y) at each pixel position (x,y) in the soft part image Gs by Expression (29). Note that in Expression (29), μm is a weighting coefficient depending on an attenuation coefficient of the muscle tissue, and μf is a weighting coefficient depending on an attenuation coefficient of the fat tissue. In addition, Δ(x,y) indicates a concentration difference distribution. The concentration difference distribution is a distribution of a concentration change on the image, which is seen from a concentration obtained by making the radiation reach the first radiation detector 5 and the second radiation detector 6 without transmitted through the subject H. The distribution of the concentration change on the image is calculated by subtracting the concentration of each pixel in the region of the subject H from the concentration in a blank region obtained by directly emitting the radiation in the soft part image Gs to the first radiation detector 5 and the second radiation detector 6.

$$rm(x,y) = \{\mu f - \Delta(x,y)/T(x,y)\}/(\mu f - \mu m) \qquad (29)$$

Moreover, the muscle mass derivation unit 110 generates a muscle image Gm from the soft part image Gs by Expression (30). Note that x and y in Expression (30) are the coordinates of each pixel of the muscle image Gm.

$$Gm(x,y) = rm(x,y) \times Gs(x,y) \qquad (30)$$

Further, as shown in Expression (31), the muscle mass derivation unit 110 derives muscle mass $M(x,y)$ (g/cm$^2$) for each pixel of the muscle image Gm by multiplying each pixel (x,y) of the muscle image Gm by the coefficient $C1(x,y)$ representing a relationship between a predetermined pixel value and the muscle mass.

$$M(x,y) = C1(x,y) \times Gm(x,y) \qquad (31)$$

The statistical value derivation unit 111 obtains a statistical value relating to the subject based on the bone density and the muscle mass derived by the bone density derivation unit 64. The statistical value is used for calculation of the evaluation value of the fracture risk for evaluating the fracture risk, as will be described below. Specifically, as shown in Expression (32), the statistical value derivation unit 111 derives a statistical value Q based on a bone density distribution index value Bd relating to the spatial distribution of bone density and a muscle mass distribution index value Md relating to the spatial distribution relating to the muscle mass.

$$Q = W1 \times Bd + W2 \times Md \qquad (32)$$

W1 and W2 in Expression (32) are weighting coefficients, respectively, and a large amount of the bone density distribution index values and the muscle mass distribution index values are collected and determined depending on regression analysis.

The bone density distribution index value is a value representing a spread aspect of the bone density value. Examples of the bone density distribution index value include a value of the bone density per unit area, an average value thereof, an intermediate value thereof, a maximum value thereof, a minimum value thereof, and the like. The muscle mass distribution index value is a value representing a spread aspect of the muscle mass value. Examples of the muscle mass distribution index value include an average value of the muscle mass, an intermediate value thereof, a maximum value thereof, a minimum value thereof, and the like.

In addition, the statistical value derivation unit 111 may obtain the statistical value Q based on at least one of the height, the weight, the age, or the fracture history of the subject in addition to the bone density and the muscle mass. For example, in a case of obtaining the statistical value based on the bone density, the muscle mass, and the age, the statistical value Q is calculated by Expression (33) based on the bone density distribution index value Bd, the muscle mass distribution index value Md, and an age Y.

$$Q = W1 \times Bd + W2 \times Md + W3 \times Y \qquad (33)$$

W1, W2, and W3 of Expression (33) are weighting coefficients, respectively, a large amount of data relating to the bone density distribution index value, the muscle mass distribution index value, and the age of the subject corresponding to the index values are collected, and the weighting coefficients W1, W2, and W3 are determined based on the regression analysis based on the data. Note that in a case in which the height, the weight, and the fracture history of the subject are added in addition to the age to obtain the statistical value, it is preferable to perform addition by multiplying by the weighting coefficient.

In a case in which Expression (33) is used, in a case in which the weighting coefficient obtained by the regression analysis based on a large amount of data is "W1=2.0, W2=0.1, W3=-0.01", assuming that the bone density distribution index value Bd of a certain subject H is "1.0 g/cm$^2$", the muscle mass distribution index value is "20 kg", and the age Y is "40 years old", the statistical value Q is "3.6" by Expression (34).

$$Q = 2.0 \times 1.0 + 0.1 \times 20 + (-0.01) \times 40 = 3.6 \qquad (34)$$

The evaluation value derivation unit 112 calculates the evaluation value of the fracture risk for evaluating the fracture risk of the subject H based on the statistical value Q. Since the relationship between the statistical value Q and the evaluation value of the fracture risk is obtained from a large amount of diagnostic data, the evaluation value derivation unit 112 calculates the evaluation value of the fracture risk using this relationship. The relationship between the statistical value Q and the evaluation value of the fracture risk need only be derived in advance and stored in the storage 53 as a table.

Figure 51:
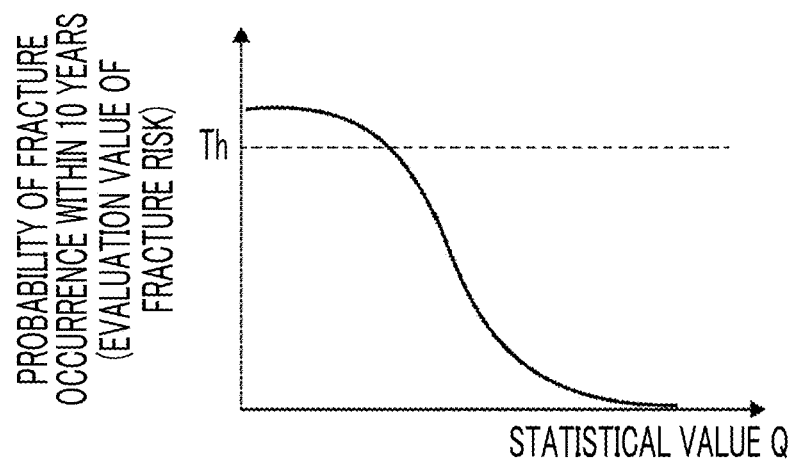
FIG. 51 is a graph showing a relationship between a statistical value and a probability of fracture occurrence within 10 years.

For example, as the evaluation value of the fracture risk, there is a probability of fracture occurrence within 10 years from the time of diagnosis of the subject H (at the time of acquisition of the first and second radiation images G1 and G2). Further, as described above, in a case in which the statistical value Q is calculated by using Expression (33) and the weighting coefficient obtained by the regression analysis based on a large amount of data is "W1=2.0, W2=0.1, W3=-0.01", the relationship between the "probability of fracture occurrence within 10 years" and the "statistical value Q" is represented such that the probability of fracture occurrence is lower as the statistical value Q is larger, as shown in FIG. 51.

Figure 52:
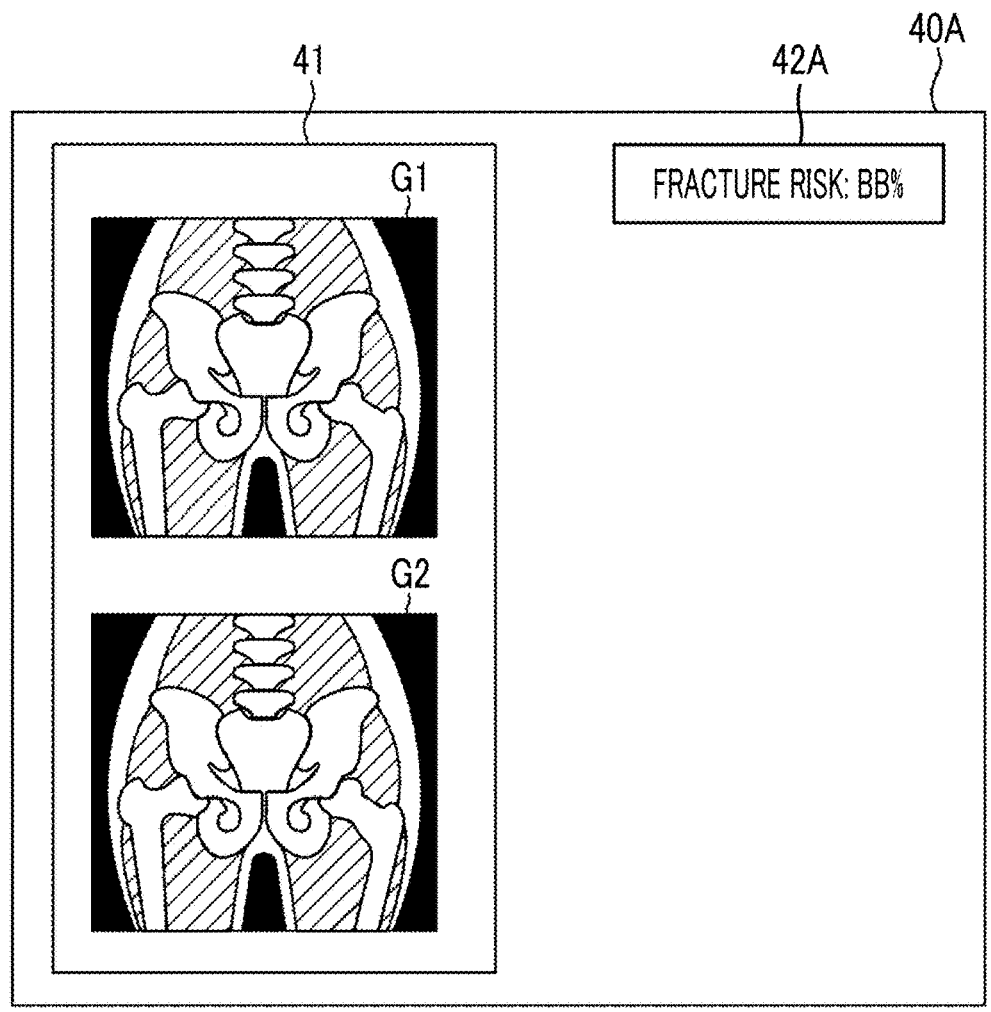
FIG. 52 is a diagram showing another example of the teacher data.

In the tenth embodiment, the evaluation value of the fracture risk derived by the information derivation device 50G is used as the correct answer data of the teacher data. FIG. 52 is a diagram showing the teacher data derived in the tenth embodiment. As shown in FIG. 52, teacher data 40A consists of the learning data 41 including the first and second radiation images G1 and G2, and correct answer data 42A which is the evaluation value of the fracture risk.

By learning the neural network by using the teacher data 40A shown in FIG. 52, it is possible to construct the learned neural network 23A that outputs the evaluation value of the fracture risk as the result of estimation relating to the bone density in a case in which the simple radiation image G0 is input.

Figure 53:
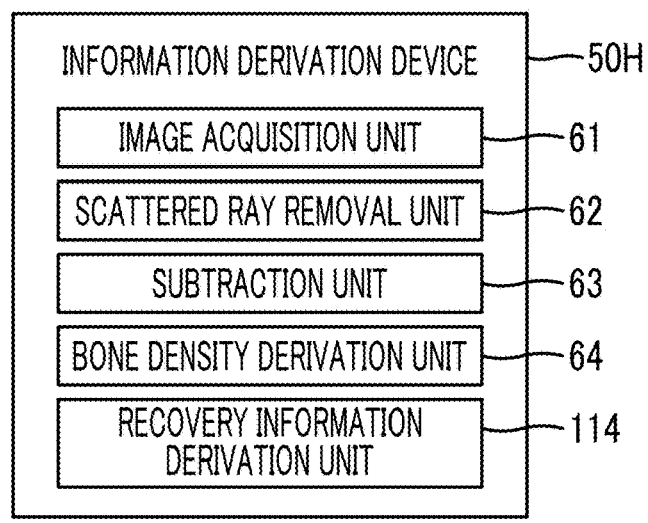
FIG. 53 is a diagram showing a functional configuration of an information derivation device according to an eleventh embodiment.

Then, an eleventh embodiment of the present disclosure will be described. FIG. 53 is a diagram showing a functional configuration of an information derivation device according to the eleventh embodiment. Note that in FIG. 53, the same reference numerals are assigned to the same configurations as those in FIG. 7, and the detailed description thereof will be omitted. In the eleventh embodiment of the present disclosure, instead of deriving the bone density as the correct answer data 42, information representing a recovery state of the bone part after a treatment is derived. Therefore, as shown in FIG. 53, an information derivation device 50H according to the eleventh embodiment further comprises a recovery information derivation unit 114 with respect to the information derivation device 50 according to the first embodiment. Note that in the eleventh embodiment, as the treatment for the bone part, a surgery for embedding an artificial material, such as an artificial bone, in the bone part is performed.

The recovery information derivation unit 114 derives the information representing a state of the bone part of the subject after the artificial material is embedded in the bone part of the subject H as the recovery information based on the bone density in the vicinity of the artificial material, such as the artificial bone, embedded in the bone part of the subject H. The artificial material, such as the artificial bone, is surgically embedded in the living body to replace bone lost due to pulverization fracture, tumor, or the like.

Figure 54:
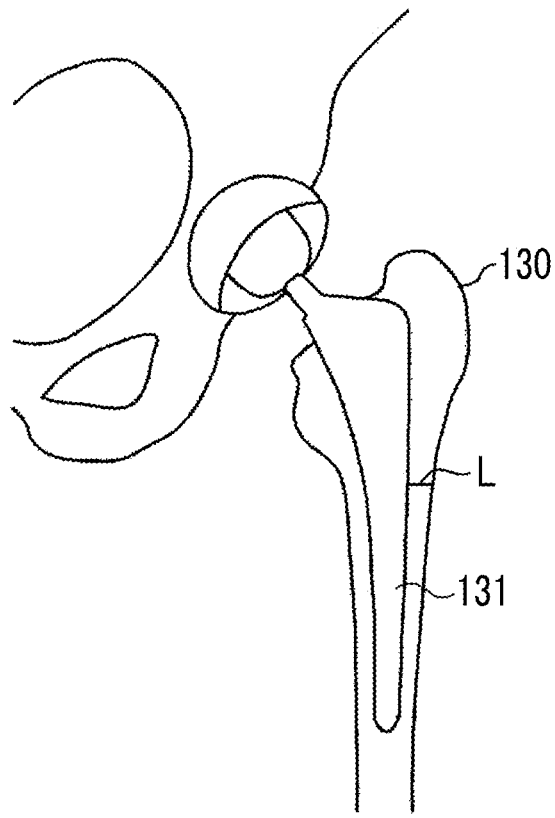
FIG. 54 is a diagram showing an example of an artificial bone embedded in the bone part of the subject.

FIG. 54 is a diagram showing an example of the artificial bone embedded in the bone part of the subject. FIG. 54 shows the bone part of the subject H that subjected to artificial hip joint replacement therapy, and a stem 131 of the artificial joint is embedded in a femur 130 of the subject H.

As a method for fixing the stem 131, a direct fixation method (cementless fixation) and an indirect fixation method (cement fixation) are known. In the direct fixation method, the stem 131 is inserted into an internal cavity of the femur 130 without the use of cement. The internal cavity of the femur 130 is shaped in advance to fit the stem 131. A surface of the stem 131 is roughened, and the bone tissue grows so as to permeate the inside of the stem 131. That is, immediately after embedding the stem 131 in the femur 130, the cavity is present between the stem 131 and the femur 130, but in a case in which the femur 130 is recovered, the cavity shrinks and disappears as the bone tissue grows. Therefore, by acquiring the bone density in the vicinity of the stem 131, it is possible to grasp the degree of recovery of the femur 130 after the surgery.

Figure 55:
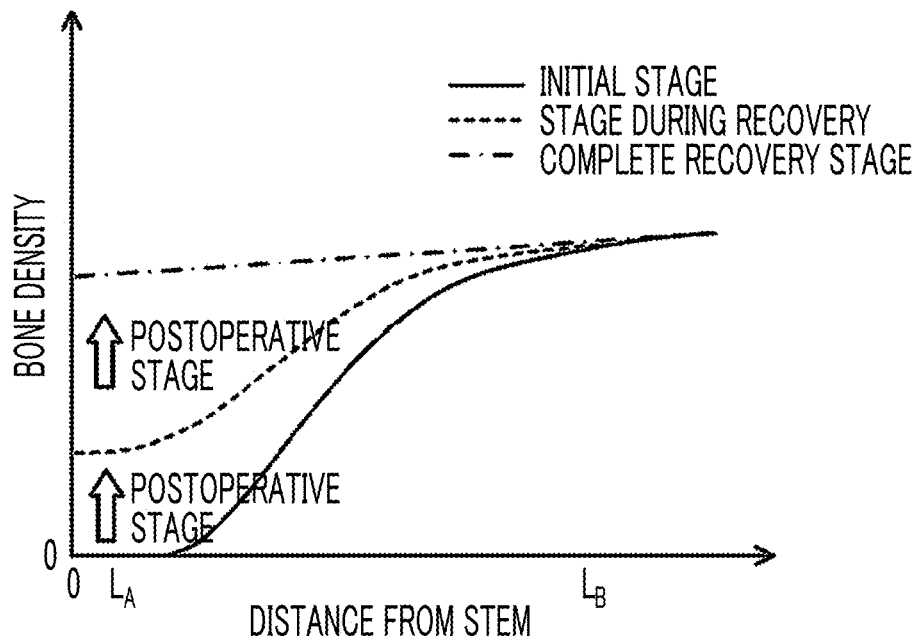
FIG. 55 is a graph showing an example of a relationship between a distance from a stem and the bone mineral density in the inside of a femur at each postoperative stage.

FIG. 55 is a graph showing an example of the relationship between the distance from the stem 131 and the bone density in the inside of the femur 130 at each postoperative stage. A horizontal axis of the graph shown in FIG. 55 is a position along a straight line L in FIG. 54. In FIG. 55, a solid line corresponds to an initial stage immediately after the stem 131 is embedded in the femur 130, a dotted line corresponds to a stage during recovery, and a long dashed short dashed line corresponds to a complete recovery stage. As shown in FIG. 55, in the initial stage after the surgery, the femur 130 and the stem 131 are not closely attached to each other, and the bone density in the vicinity of the stem 131 is extremely low. As the bone tissue grows so as to permeate the inside of the stem 131 with recovery, the bone density in the vicinity of the stem 131 is increased. On the other hand, the bone density at the distant position from the stem 131 is substantially fixed at each postoperative stage. At the complete recovery stage, the bone density in the vicinity of the stem 131 and the bone density at the distant position are substantially equivalent.

Hereinafter, an aspect in which the recovery information derivation unit 114 derives the recovery information will be described by taking a case in which the total hip joint replacement therapy shown in FIG. 54 is performed as an example. The recovery information derivation unit 114 derives a numerical value $\Delta B$ depending on a difference between a bone density $B_A$ at a position $L_A$ at which the distance from the stem 131 is relatively short and a bone density $B_B$ at a position $X_B$ at which the distance from the stem 131 is relatively long, as the recovery information. For example, the recovery information derivation unit 114 may derive the difference in the bone density ($\Delta B = B_B - B_A$) as the recovery information. In this case, the numerical value derived as the recovery information is reduced with recovery and reaches 0. In addition, the recovery information derivation unit 114 may derive the bone density ratio ($\Delta B = B_A/B_B$) as the recovery information. In this case, the numerical value $\Delta B$ derived as the recovery information is increased with the recovery of the bone part and approaches 1. That is, it can be said that the numerical value $\Delta B$ depending on the difference between the bone density $B_A$ and the bone density $B_B$ is the numerical value representing the degree of recovery of the bone part after the surgery. Therefore, by deriving the numerical value $\Delta B$ as the recovery information, it is possible to quantitatively grasp the degree of recovery of the femur 130 after the surgery.

Note that the recovery information derivation unit 114 derives the recovery information by using the bone density B for each pixel of the bone part image Gb derived by the bone density derivation unit 64. In any of the first radiation image G1, the second radiation image G2, or the bone part image Gb, the pixel value of the stem 131 is significantly different from the pixel value in the bone region, and thus it is possible to specify the region in which the stem 131 is present in each of the above images. Therefore, the recovery information derivation unit 114 can specify the distance from the stem 131 based on any one of the first radiation image G1, the second radiation image G2, or the bone part image Gb.

Figure 56:
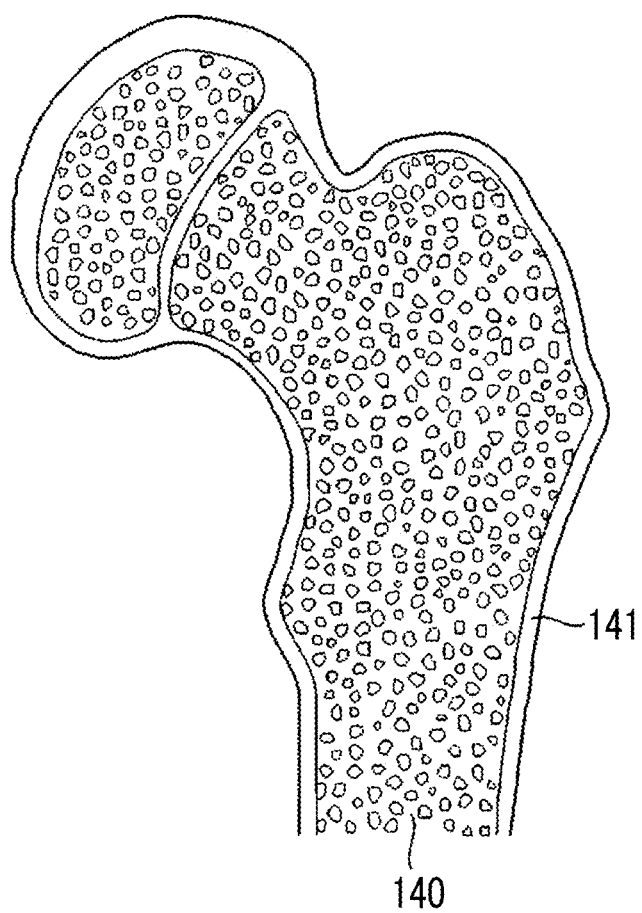
FIG. 56 is a cross-sectional view showing an example of a cross-sectional structure of a human bone.

FIG. 56 is a cross-sectional view showing an example of a cross-sectional structure of a human bone. As shown in FIG. 56, the human bone is composed of a cancellous bone 140 and a cortical bone 141 that covers the outside of the cancellous bone 140. The cortical bone 141 is harder and denser than the cancellous bone 140. The cancellous bone 140 is a collection of small bone columns called bone trabeculae that extend into the bone marrow cavity. The form of the bone trabecula includes a plate-like structure and a rod-like structure, which are connected to each other. Since the bone density of the cancellous bone 140 and the bone density of the cortical bone 141 are significantly different from each other, it is possible to distinguish the cortical bone 141 and the cancellous bone 140 from the bone density B for each pixel of the bone part image Gb.

In a case in which the artificial material is embedded in the cancellous bone 140, the recovery information derivation unit 114 may specify the region of the cancellous bone 140 based on the bone density B for each pixel of the bone part image Gb, and may derive the recovery information based on the bone density of the cancellous bone 140 in the vicinity of the artificial material. Specifically, the recovery information derivation unit 114 may derive the numerical value $\Delta B$ depending on the difference between the bone density $B_A$ at a position $X_A$ in the cancellous bone 140 at which the distance from the artificial material is relatively short and the bone density $B_B$ at a position $X_B$ in the cancellous bone 140 at which the distance from the artificial material is relatively long, as the recovery information.

On the other hand, in a case in which the artificial material is embedded in the cortical bone 141, it is preferable that the recovery information derivation unit 114 specify the region of the cortical bone 141 based on the bone density B for each pixel of the bone part image Gb, and derive the recovery information based on the bone density of the cortical bone 141 in the vicinity of the artificial material. Specifically, the recovery information derivation unit 114 may derive the numerical value $\Delta B$ depending on the difference between the bone density $B_A$ at a position $X_A$ in the cortical bone 141 at which the distance from the artificial material is relatively short and the bone density $B_B$ at a position $X_B$ in the cortical bone 141 at which the distance from the artificial material is relatively long, as the recovery information.

In a case in which the artificial material embedded in the bone part of the subject H extends to both the cancellous bone 140 and the cortical bone 141, the regions of the cancellous bone 140 and the cortical bone 141 may be specified based on the bone density B for each pixel of the bone part image Gb, and the recovery information may be derived based on both the bone density of the cancellous bone 140 and the bone density of the cortical bone 141 in the vicinity of the artificial material. Specifically, the recovery information derivation unit 114 may derive the numerical value ΔB1 depending on the difference between the bone density $B_{A1}$ at a position $L_{A1}$ in the cancellous bone 140 at which the distance from the artificial material is relatively short and the bone density $B_{B1}$ at a position $L_{B1}$ in the cancellous bone 140 at which the distance from the artificial material is relatively long, as the recovery information, and may derive the numerical value ΔB2 depending on the difference between the bone density $B_{A2}$ at a position $L_{A2}$ in the cortical bone 141 at which the distance from the artificial material is relatively short and the bone density $B_{B2}$ at a position $L_{B2}$ in the cortical bone 141 at which the distance from the artificial material is relatively long, as the recovery information. Note that in a case in which the artificial material embedded in the bone part of the subject H extends to both the cancellous bone 140 and the cortical bone 141, the recovery information may be derived based on one of the bone density of the cancellous bone 140 and the bone density of the cortical bone 141 in the vicinity of the artificial material. That is, one of the numerical value ΔB1 or the numerical value ΔB2 may be derived as the recovery information.

Figure 57:
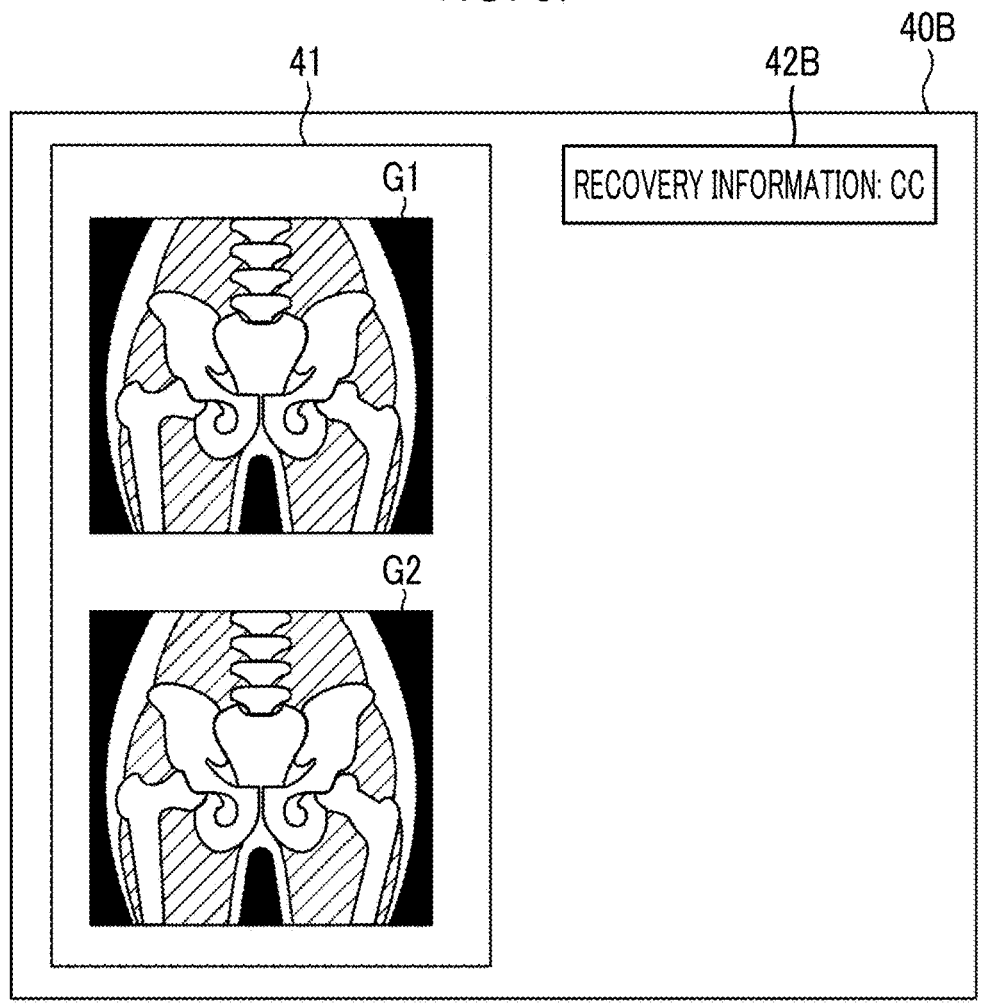
FIG. 57 is a diagram showing still another example of the teacher data.

In the eleventh embodiment, the recovery information derived by the information derivation device 50H according to the eleventh embodiment is used as the correct answer data of the teacher data. FIG. 57 is a diagram showing the teacher data derived in the eleventh embodiment. As shown in FIG. 57, teacher data 40B consists of the learning data 41 including the first and second radiation images G1 and G2, and correct answer data 42B which is the numerical value of the recovery information.

By learning the neural network by using the teacher data 40B shown in FIG. 57, it is possible to construct the learned neural network 23A that outputs the information representing the recovery state as the recovery information in a case in which the simple radiation image G0 is input.

Then, an information derivation device according to a twelfth embodiment of the present disclosure will be described. Note that a configuration of the information derivation device according to the twelfth embodiment is the same as the configuration of the information derivation device according to the first embodiment, and only the processing performed by the scattered ray removal unit 62 is different, so that the detailed description will be omitted here. Note that in the twelfth embodiment, the first and second radiation images G1 and G2 acquired by imaging the subject H by using the imaging apparatus 1A shown in FIG. 30 are used as the teacher data 40 as in the sixth embodiment.

Figure 58:
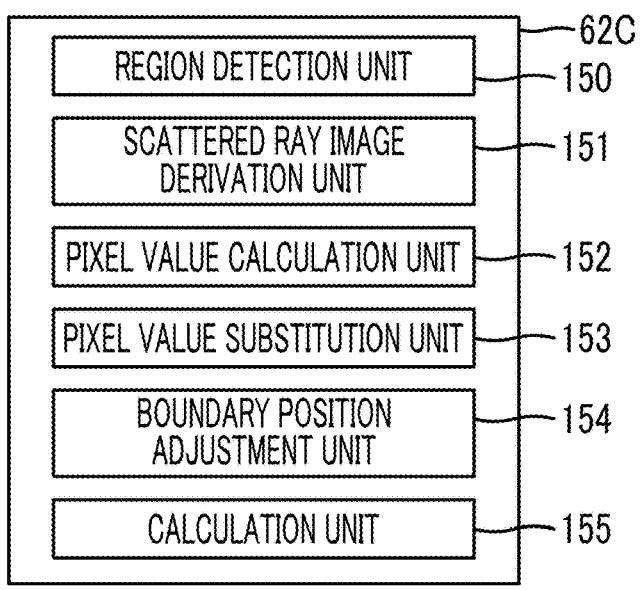
FIG. 58 is a diagram showing a functional configuration of a scattered ray removal unit of an information derivation device according to a twelfth embodiment.

FIG. 58 is a diagram showing a functional configuration of the scattered ray removal unit of the information derivation device according to the twelfth embodiment. As shown in FIG. 58, a scattered ray removal unit 62C of the information derivation device according to the twelfth embodiment comprises a region detection unit 150, a scattered ray image derivation unit 151, a pixel value calculation unit 152, a pixel value substitution unit 153, a boundary position adjustment unit 154, and a calculation unit 155.

The region detection unit 150 obtains the region detection image by detecting a subject region in which the radiation is transmitted through the subject H and reaches the first and second radiation detectors 5 and 6, and a direct radiation region in which the radiation is transmitted through only the top plate 4A and directly reaches the first and second radiation detectors 5 and 6 without being transmitted through the subject H in the first and second radiation images G1 and G2.

Figure 59:
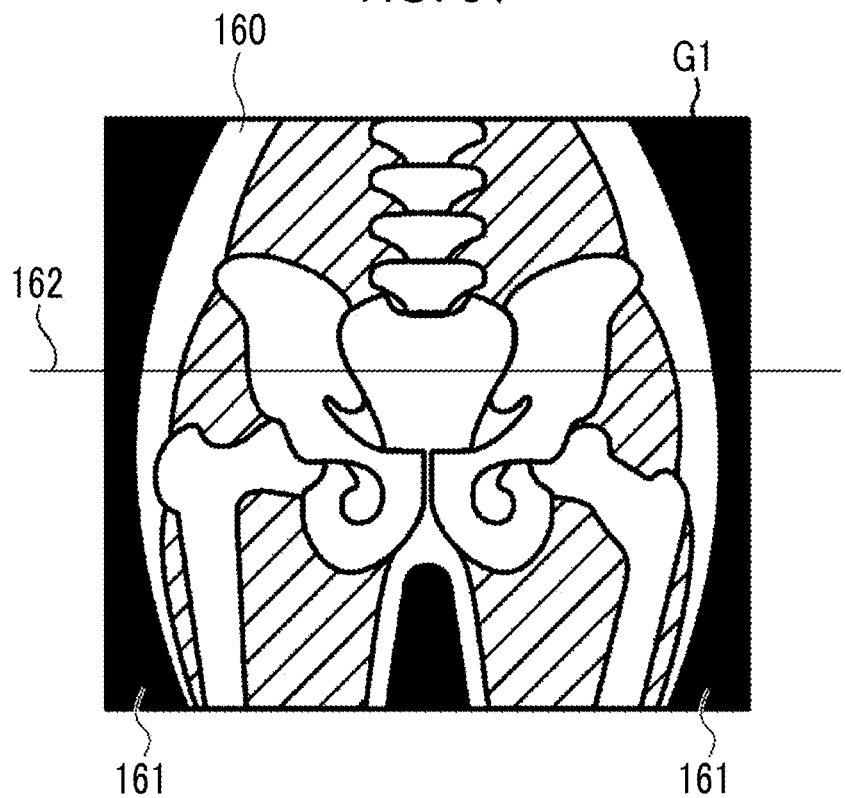
FIG. 59 is a diagram for describing detection of a subject region and a direct radiation region.
Figure 60:
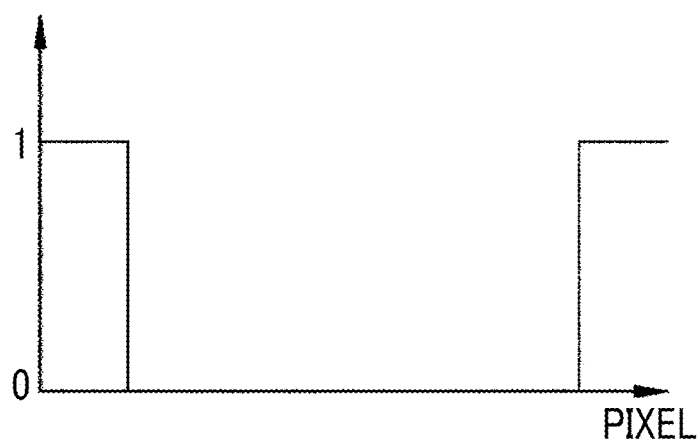
FIG. 60 is a diagram showing a region detection image of a specific line portion.

Specifically, as shown in FIG. 59, the region detection unit 150 detects the region in which the pixel value of the first radiation image G1 is smaller than a region threshold value as a subject region 160, and detects the region in which the pixel value of the first radiation image G1 is equal to or larger than the region threshold value as a direct radiation region 161. For example, in a case in which the region detection image is a binarized image in which the subject region 160 is "0" and the direct radiation region 161 is "1", the distribution shown in FIG. 60 is obtained in a specific line 162 of the first radiation image G1. Note that the region detection unit 150 may use the learned neural network that is learned to detect the subject region and the direct radiation region instead of the region detection by threshold value processing.

Note that the region threshold value is determined for each imaging condition, and it is preferable to use the region threshold value corresponding to the imaging condition in a case of imaging the subject H. In addition, region detection processing may be performed on both the first radiation image G1 and the second radiation image G2, but may be performed on any one of the first radiation image G1 or the second radiation image G2.

The scattered ray image derivation unit 151 obtains the scattered ray image relating to the scattered ray component based on the region detection image and scattered ray spread information relating to the spread of the scattered ray. The calculation unit 155 obtains the radiation image from which the scattered ray component is removed by subtracting the scattered ray image from the first and second radiation images G1 and G2. Note that as the scattered ray spread information used in the scattered ray image derivation unit 151, for example, the information shown in FIG. 41 can be used.

Further, the scattered ray image derivation unit 151 obtains the scattered ray image including the scattered ray component by the calculation of "region detection image*PSF (* is a convolution operator)" that convolves the region detection image and the PSF. Note that the scattered ray image derivation unit 151 derives the scattered ray image for each of the first radiation image G1 and the second radiation image G2.

In the scattered ray image, as the pixel value of the scattered ray component in the direct radiation region, the pixel value of the direct radiation region 161 of the first and second radiation images G1 and G2 may be used as it is, but the pixel value of the direct radiation region 161 is often saturated (exceeding the pixel value that imaging sensors of the first and second radiation detectors 5 and 6 can receive). Therefore, as the pixel value in the direct radiation region of the scattered ray image, it is preferable theoretically calculate an unsaturated scattered ray pixel value, which is a unsaturated pixel value in which the pixel value is not saturated and the influence of the scattered ray is taken into consideration, and to substitute the theoretically calculated unsaturated scattered ray pixel value with the pixel value in the direct radiation region of the scattered ray image.

Figure 61:
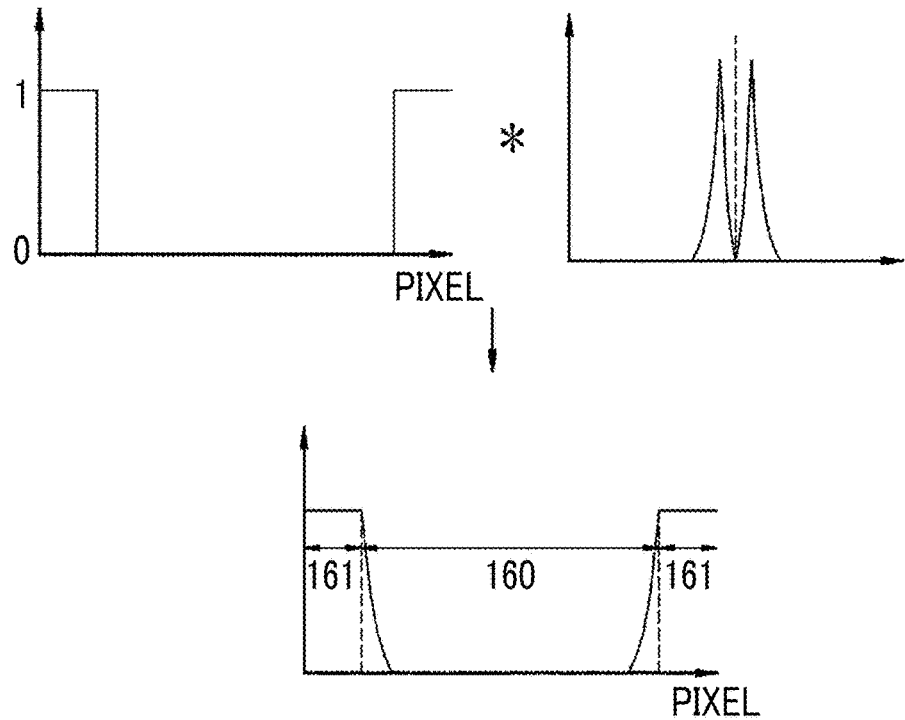
FIG. 61 is a diagram showing a scattered ray image of the specific line portion.

The pixel value calculation unit 152 calculates the unsaturated scattered ray pixel value corresponding to the imaging dose by referring to an unsaturated scattered ray pixel value relationship representing a relationship between the dose of the radiation and the unsaturated scattered ray pixel value, which is the unsaturated pixel value in which the pixel value is not saturated and the influence of the scattered ray is taken into consideration. Further, the pixel value substitution unit 153 substitutes the pixel value in the direct radiation region with the unsaturated scattered ray pixel value. Specifically, as shown in FIG. 61, in the scattered ray image derived by the scattered ray image derivation unit 151, the pixel value of the direct radiation region 161 is substituted by the unsaturated scattered ray pixel value obtained by the pixel value calculation unit 152.

The unsaturated scattered ray pixel value relationship is predetermined in a table (not shown) for the direct radiation region for each imaging condition, and is stored in the storage 53. The pixel value calculation unit 152 refers to the table for the direct radiation region to use any of the unsaturated scattered ray pixel value relationships corresponding the imaging condition in a case of imaging the subject H, or use a plurality of the unsaturated scattered ray pixel value relationships satisfying the imaging condition in a case of imaging the subject H in combination. In addition, it is preferable to calculate the unsaturated scattered ray pixel value by, for example, "unsaturated scattered ray pixel value=unsaturated pixel value obtained in a case in which the pixel value is not saturated×scattered fraction in the direct radiation region".

As described above, the region detection unit 150 distinguishes the subject region 160 and the direct radiation region 161 by using the region threshold value, but the direct radiation region 161 detected by the region threshold value may include the region transmitted through the soft region close to the skin in the subject H. In a case in which the scattered ray is also emitted from such a soft region, in a case in which the scattered ray image is subjected to the subtraction processing from the first and second radiation images G1 and G2, the scattered ray component is excessively removed. Therefore, a boundary position between the subject region 160 and the direct radiation region 161 can be adjusted by a specific width, and the scattered ray image can be obtained based on the region detection image and the scattered ray spread information after adjusting the boundary position.

The boundary position adjustment unit 154 adjusts the boundary position between the subject region 160 and the direct radiation region 161 by the specific width. It is preferable to perform adjustment of the boundary position in a case in which the pixel value of the direct radiation region exceeds the pixel value threshold value or in a case in which the dose of the radiation exceeds a dose threshold value. In addition, it is preferable to determine the specific width based on at least one of the part of the subject H, the imaging method for the subject H, or the imaging conditions. In addition, it is preferable to determine the specific width based on the pixel value in the vicinity of the boundary position in the radiation image.

Figure 62:
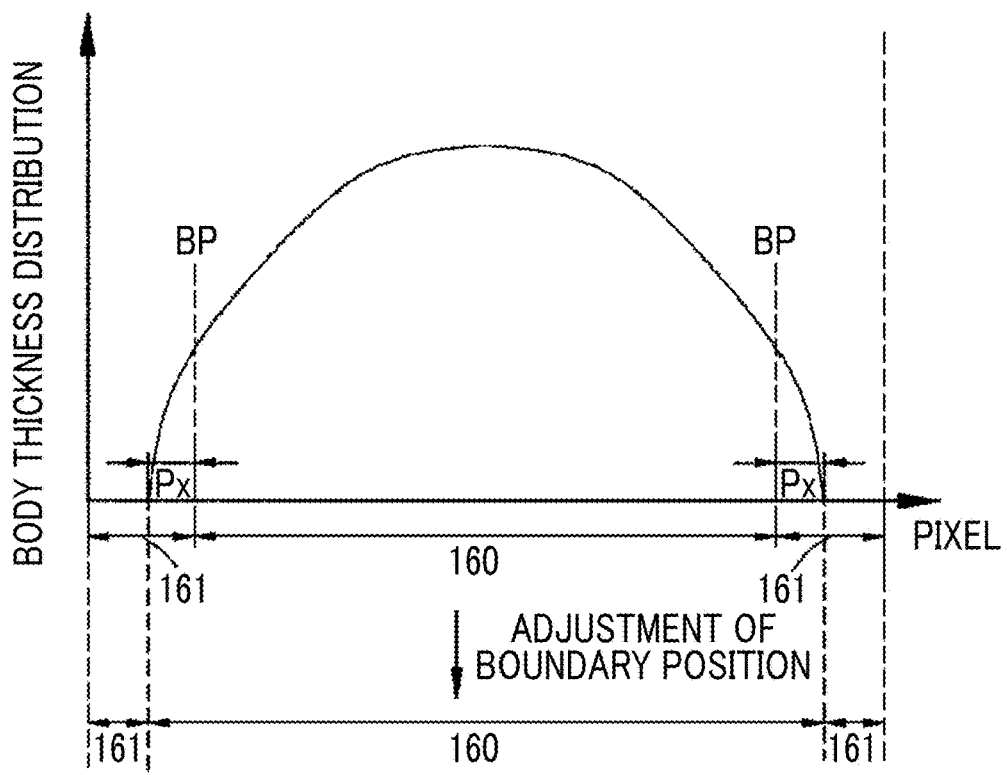
FIG. 62 is a diagram showing the body thickness distribution of the specific line portion.

Specifically, in a case in which the specific width is determined from the shape of the subject H among the parts of the subject H, that is, the body thickness distribution of the subject H, as shown in the body thickness distribution of the specific line 162 portion in FIG. 62, a portion Px in the direct radiation region 161 detected by the region threshold value, in which the body thickness exceeds 0, is used as the specific width. By adjusting a boundary position BP by the specific width corresponding to the portion Px, the subject region 160 is expanded by the specific width, while the direct radiation region 161 is narrowed by the specific width. In addition, in a case in which the specific width is determined based on the pixel value in the vicinity of the boundary position, it is preferable to determine the specific width based on the pixel-to-pixel distance between the pixel at the boundary position and the pixel within a specific range from the boundary position, which is a vicinity pixel of which the pixel value has the specific range.

In the twelfth embodiment, the subtraction unit 63 derives the bone part image Gb by using the processed first and second radiation images G1 and G2. Further, the bone density derivation unit 64 derives the bone density B and the representative value of the bone density B in the target bone by using the bone part image Gb derived by the subtraction unit 63.

Note that the scattered ray removal processing according to the twelfth embodiment may be performed in the first to fifth and eighth to eleventh embodiments.

Figure 63:
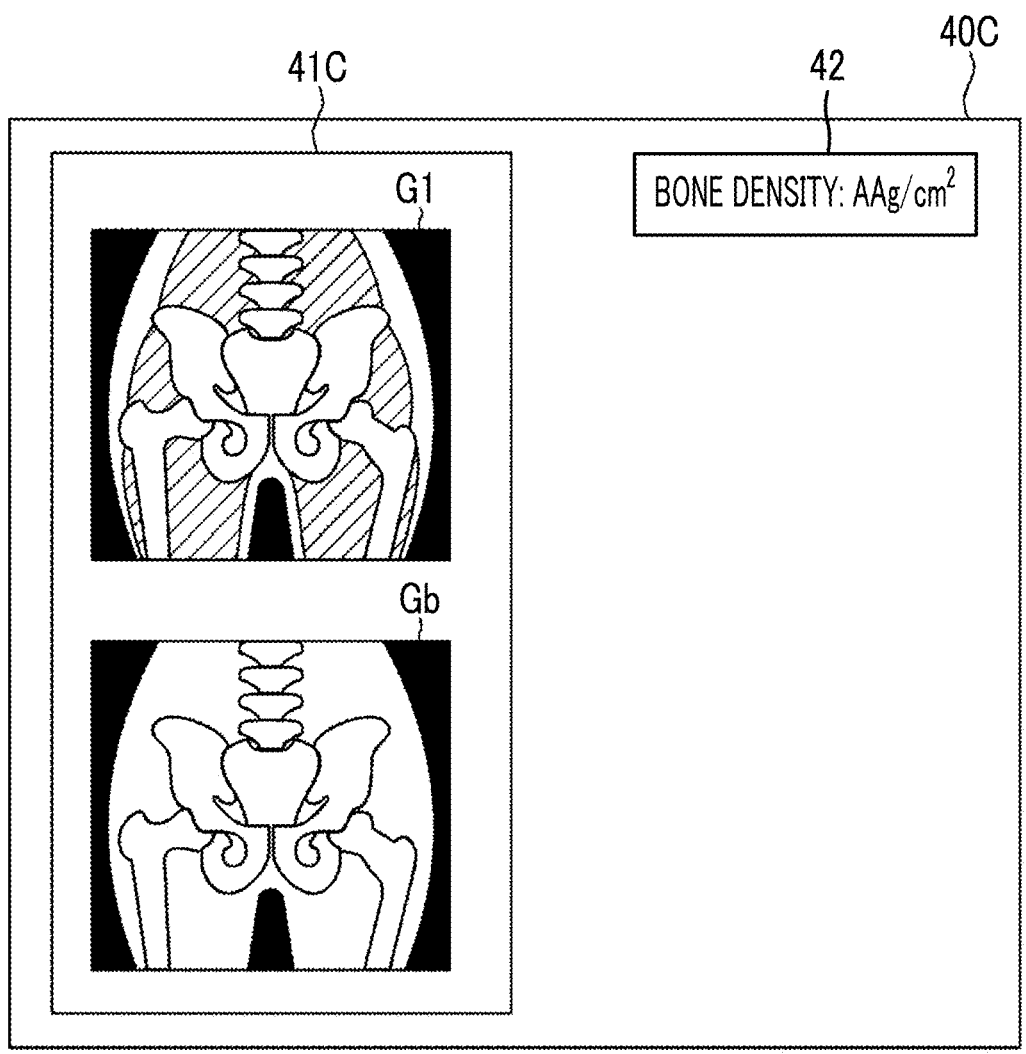
FIG. 63 is a diagram showing still another example of the teacher data.
Figure 64:
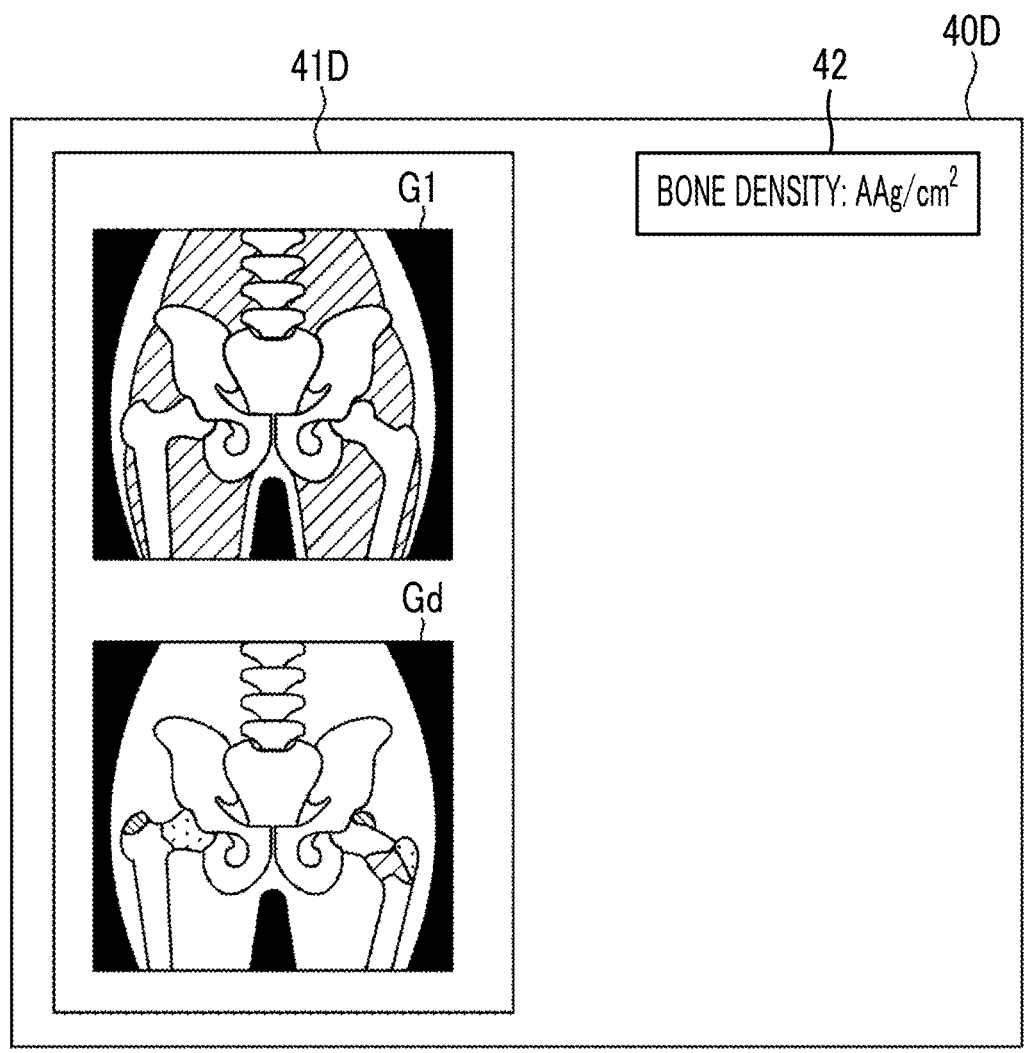
FIG. 64 is a diagram showing still another example of the teacher data.

Note that in each of the embodiments described above, the first and second radiation images G1 and G2 are used as the learning data 41 of the teacher data 40, but the present disclosure is not limited to this. As shown in teacher data 40C of FIG. 63, the bone part image Gb may be used as learning data 41C instead of the second radiation image G2. In this case, the bone part image Gb may be derived by any of the first to eleventh embodiments described above. In addition, as shown in teacher data 40D of FIG. 64, the bone density image Gd in which each pixel is the value of the bone density may be used as learning data 41D instead of the second radiation image G2. In this case, the bone density image Gd may use the value of bone density derived in any of the first to twelfth embodiments as the pixel value.

In addition, in each of the embodiments described above, as the correct answer data 42 of the teacher data 40, the bone density image in which the bone density B derived by the bone density derivation unit 64 is used as the pixel value may be used. In this case, the estimation unit 23 of the estimation device 10 derives the bone density image from the simple radiation image G0 as the result of estimation relating to the bone density. In this way, in a case in which the bone density image is derived, the bone density image may be displayed on the display screen.

Figure 65:
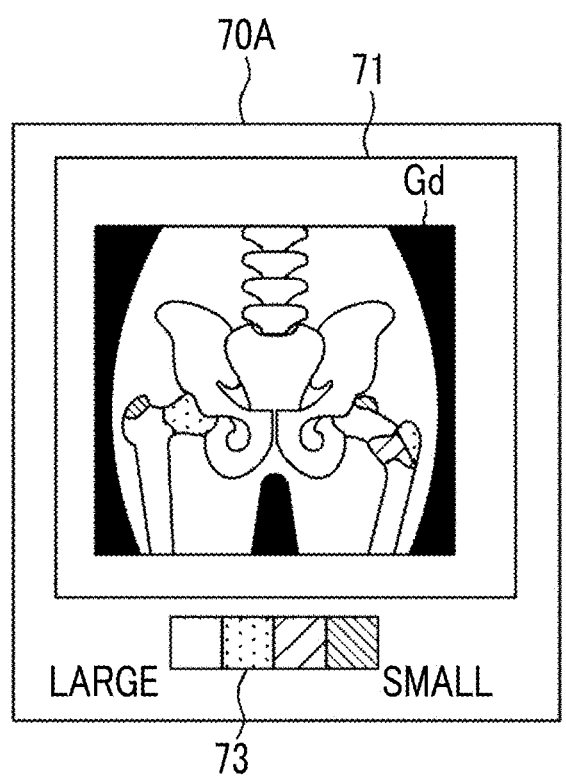
FIG. 65 is a diagram showing another example of the display screen of the result of estimation.

FIG. 65 is a diagram showing another example of the display screen of the result of estimation. As shown in FIG. 65, a display screen 70A has the image display region 71 similar to the display screen 70 shown in FIG. 13. In the image display region 71, the bone density image Gd, which is the result of estimation of the bone density in the simple radiation image G0 of the subject H, is displayed. In the bone density image Gd, a pattern is added to the bone region depending on the bone density. Note that in FIG. 65, for the sake of simplicity, the pattern representing the bone mineral density is added only to the femur. Below the image display region 71, a reference 73 representing the magnitude of the bone mineral density for the added pattern is displayed. The operator can easily recognize the bone density of the patient by interpreting the bone density image Gd with reference to the reference 73. Note that different colors may be added to the bone density image Gd depending on the bone density instead of the pattern.

In addition, in each of the embodiments described above, the information relating to the bone density of the femur in the vicinity of the hip joint is estimated, but the target bone is not limited to the femur. The technology of the present disclosure can also be applied in estimating the information relating to the bone density for any bone part, such as the femur and tibia in the vicinity of a knee joint, a vertebra, such as a lumbar vertebra, a heel bone, and a metacarpal bone.

In addition, in each of the embodiments described above, the bone density, the fracture risk, and the recovery information are used as the correct answer data included in the teacher data for learning the neural network. Therefore, the information relating to the bone density estimated by the estimation unit 23 from the simple radiation image G0 is the bone density, the fracture risk, and the recovery information in the simple radiation image G0, but the present disclosure is not limited to this. The learned neural network 23A may be constructed using YAM, T score, or Z score as the correct answer data, and the YAM, the T score, and the Z score may be estimated as the information relating to the bone density from the simple radiation image G0. In addition, in the estimation unit 23, as the estimated information relating to the bone density, a result of detection of the presence or absence of the fracture, the presence or absence of the tumor, and the presence or absence of the implant may be used, or a determination result of the osteoporosis may be used. In addition, a bone disease relating to the bone density, such as multiple myeloma, rheumatism, arthritis, and cartilage hardening, may be estimated as the information relating to the bone density. In this case, the learned neural network 23A need only be constructed by using the teacher data including the information relating to the bone density as the correct answer data.

In addition, in each of the embodiments described above, the first radiation image G1 and the second radiation image G2 itself are used in a case in which the bone density as the correct answer data is derived, but the present disclosure is not limited to this. For each pixel of the first radiation image G1 and the second radiation image G2, a movement average with the surrounding pixels is calculated, and the first radiation image G1 and the second radiation image G2 in which the movement average is used as the pixel value of each pixel may be used to derive the bone density. Here, since a cortical bone is important information in a case in which the bone density is determined, the movement average with the surrounding pixels need only be calculated for each pixel such that a resolution at which the cortical bone can be visually recognized, for example, a resolution of equal to or smaller than 2 mm in the actual size of the subject is held. In this case, the pixels to be used as the movement average need only be appropriately determined from information on a mutual distance between the radiation source 3, the subject H, and the radiation detectors 5 and 6, information on a pixel size of the radiation detectors 5 and 6, and the like.

Note that in each of the embodiments described above, the estimation device 10 learns the neural network to construct the learned neural network 23A, but the present disclosure is not limited to this. The learned neural network 23A constructed in a device other than the estimation device 10 may be used for the estimation unit 23 of the estimation device 10 in the present embodiment.

In addition, in each of the embodiments described above, the first and second radiation images G1 and G2 are acquired by the one-shot method in a case in which the energy subtraction processing is performed for deriving the bone density, but the present disclosure is not limited to this. The first and second radiation images G1 and G2 may be acquired by a so-called two-shot method in which imaging is performed twice by using only one radiation detector. In a case of the two-shot method, a position of the subject H included in the first radiation image G1 and the second radiation image G2 may shift due to a body movement of the subject H. Therefore, in the first radiation image G1 and the second radiation image G2, it is preferable to perform the processing according to the present embodiment after registration of the subject is performed.

As registration processing, for example, a method disclosed in JP2011-255060A can be used. In the method disclosed in JP2011-255060A, for each of the first and second radiation images G1 and G2, a plurality of first band images and a plurality of second band images representing structures having different frequency bands are generated, a misregistration amount of the positions corresponding to each other in the first band image and the second band image of the corresponding frequency band is acquired, and the registration of the first radiation image G1 and the second radiation image G2 is performed based on the misregistration amount.

In addition, in each of the embodiments described above, the derivation of the bone density as the correct answer data of the teacher data and the estimation processing of the information relating to the bone density are performed by using the radiation image acquired by the system that images the subject H by using the first and second radiation detectors 5 and 6, it is needless to say that the technology of the present disclosure can be applied to even in a case in which the first and second radiation images G1 and G2 are acquired by using an accumulative phosphor sheet instead of the radiation detector. In this case, the first and second radiation images G1 and G2 need only be acquired by stacking two accumulative phosphor sheets, emitting the radiation transmitted through the subject H, accumulating and recording radiation image information of the subject H in each of the accumulative phosphor sheets, and photoelectrically reading the radiation image information from each of the accumulative phosphor sheets. Note that the two-shot method may also be used in a case in which the first and second radiation images G1 and G2 are acquired by using the accumulative phosphor sheet.

In addition, the radiation in the embodiments described above is not particularly limited, and α-rays or γ-rays can be used in addition to X-rays.

In addition, in the embodiments described above, various processors shown below can be used as the hardware structures of processing units that execute various pieces of processing, such as the image acquisition unit 21, the information acquisition unit 22, the estimation unit 23, the learning unit 24, and the display controller 25 of the estimation device 10, and the image acquisition unit 61, the scattered ray removal unit 62, the subtraction unit 63, and the bone density derivation unit 64 of the information derivation device 50. As described above, the various processors include, in addition to the CPU that is a general-purpose processor which executes software (program) and functions as various processing units, a programmable logic device (PLD) that is a processor whose circuit configuration can be changed after manufacture, such as a field programmable gate array (FPGA), and a dedicated electric circuit that is a processor having a circuit configuration which is designed for exclusive use in order to execute specific processing, such as an application specific integrated circuit (ASIC).

One processing unit may be configured by one of these various processors, or may be a combination of two or more processors of the same type or different types (for example, a combination of a plurality of FPGAs or a combination of the CPU and the FPGA). In addition, a plurality of the processing units may be configured by one processor.

As an example of configuring the plurality of processing units by one processor, first, as represented by a computer, such as a client and a server, there is an aspect in which one processor is configured by a combination of one or more CPUs and software and this processor functions as a plurality of processing units. Second, as represented by a system on chip (SoC) or the like, there is an aspect of using a processor that realizes the function of the entire system including the plurality of processing units by one integrated circuit (IC) chip. In this way, as the hardware structure, the various processing units are configured by using one or more of the various processors described above.

Moreover, as the hardware structures of these various processors, more specifically, it is possible to use an electrical circuit (circuitry) in which circuit elements, such as semiconductor elements, are combined.

EXPLANATION OF REFERENCES

What is claimed is:
1. An estimation device comprising:
at least one processor,
wherein the processor functions as a learned neural network that derives a result of estimation relating to a bone density of a bone part from a simple radiation image acquired by simply imaging a subject including the bone part, and
the learned neural network is learned by using, as teacher data, (i) two radiation images acquired by imaging the subject including the bone part with radiation having different energy distributions, (ii) the radiation image of the subject and a bone part image representing the bone part of the subject, or (iii) the radiation image of the subject and a bone density image representing the bone density of the bone part of the subject, and information relating to the bone density of the bone part of the subject,
wherein the information relating to the bone density is derived based on a body thickness distribution of the subject estimated based on at least one radiation image of the two radiation images acquired by imaging the subject including the bone part and a soft part with the radiation having different energy distributions, an imaging condition in a case in which the two radiation images are acquired, and a pixel value of a bone region in the bone part image obtained by extracting the bone part, the bone part image being derived by energy subtraction processing of performing weighting subtraction on the two radiation images, and
wherein the bone part image is derived by deriving a new weighting coefficient used for the weighting subtraction based on a pixel value of the bone part included in the bone part image, deriving a new bone part image by performing the weighting subtraction on the two radiation images by using the new weighting coefficient, and repeating derivation of a further new weighting coefficient based on the new bone part image and derivation of a further new bone part image based on the further new weighting coefficient.
2. An estimation device comprising:
at least one processor,
wherein the processor functions as a learned neural network that derives a result of estimation relating to a bone density of a bone part from a simple radiation image acquired by simply imaging a subject including the bone part, and
the learned neural network is learned by using, as teacher data, (i) two radiation images acquired by imaging the subject including the bone part with radiation having different energy distributions, (ii) the radiation image of the subject and a bone part image representing the bone part of the subject, or (iii) the radiation image of the subject and a bone density image representing the bone density of the bone part of the subject, and information relating to the bone density of the bone part of the subject,
wherein the information relating to the bone density is derived based on a body thickness distribution of the subject estimated based on at least one radiation image of the two radiation images acquired by imaging the subject including the bone part and a soft part with the radiation having different energy distributions, an imaging condition in a case in which the two radiation images are acquired, and a pixel value of a bone region in the bone part image obtained by extracting the bone part, the bone part image being derived by energy subtraction processing of performing weighting subtraction on the two radiation images, and
wherein the bone part image is derived by deriving, for each of different energy distributions, a difference between a value of an attenuation coefficient of the soft part×a thickness of the soft part+an attenuation coefficient of the bone part×a thickness of the bone part, and each pixel value of the radiation image while changing, from initial values, the attenuation coefficient of the soft part for each of different energy distributions, the thickness of the soft part, the attenuation coefficient of the bone part for each of different energy distributions, and the thickness of the bone part, deriving the attenuation coefficient of the soft part and the attenuation coefficient of the bone part for each of different energy distributions, at which the difference is minimized or the difference is smaller than a predetermined threshold value, and performing the energy subtraction processing by using a weighting coefficient derived based on the attenuation coefficient of the soft part and the attenuation coefficient of the bone part.
3. An estimation device comprising:
at least one processor,
wherein the processor functions as a learned neural network that derives a result of estimation relating to a bone density of a bone part from a simple radiation image acquired by simply imaging a subject including the bone part, and
the learned neural network is learned by using, as teacher data, (i) two radiation images acquired by imaging the subject including the bone part with radiation having different energy distributions, (ii) the radiation image of the subject and a bone part image representing the bone part of the subject, or (iii) the radiation image of the subject and a bone density image representing the bone density of the bone part of the subject, and information relating to the bone density of the bone part of the subject,
wherein the information relating to the bone density is derived based on a body thickness distribution of the subject estimated based on at least one radiation image of the two radiation images acquired by imaging the subject including the bone part and a soft part with the radiation having different energy distributions, an imaging condition in a case in which the two radiation images are acquired, and a pixel value of a bone region in the bone part image obtained by extracting the bone part, the bone part image being derived by energy subtraction processing of performing weighting subtraction on the two radiation images, and wherein the bone part image is derived by deriving a composition ratio of a plurality of compositions included in the soft part of the subject, deriving, for each pixel of the two radiation images, an attenuation coefficient of the soft part for each of different energy distributions depending on the composition ratio, and performing the energy subtraction processing by using a weighting coefficient derived based on the derived attenuation coefficient of the soft part and a predetermined attenuation coefficient of the bone part.

4. The estimation device according to claim 3, wherein the composition ratio is obtained by deriving a body thickness of the subject as a first body thickness and a second body thickness for each pixel of each of the two radiation images and deriving the composition ratio for each pixel of the radiation image based on the first body thickness and the second body thickness.

5. The estimation device according to claim 4, wherein the composition ratio is obtained by deriving the first body thickness and the second body thickness based on an attenuation coefficient of each of the plurality of compositions for each of different energy distributions, deriving the first body thickness and the second body thickness while changing a thickness of the composition and the attenuation coefficient of each composition, and deriving the composition ratio based on the thickness of the composition in which a difference between the first body thickness and the second body thickness is equal to or smaller than a predetermined threshold value.

6. An estimation device comprising:

at least one processor, wherein the processor functions as a learned neural network that derives a result of estimation relating to a bone density of a bone part from a simple radiation image acquired by simply imaging a subject including the bone part, and the learned neural network is learned by using, as teacher data, (i) two radiation images acquired by imaging the subject including the bone part with radiation having different energy distributions, (ii) the radiation image of the subject and a bone part image representing the bone part of the subject, or (iii) the radiation image of the subject and a bone density image representing the bone density of the bone part of the subject, and information relating to the bone density of the bone part of the subject, wherein the information relating to the bone density is derived based on a body thickness distribution of the subject estimated based on at least one radiation image of the two radiation images acquired by imaging the subject including the bone part and a soft part with the radiation having different energy distributions, an imaging condition in a case in which the two radiation images are acquired, and a pixel value of a bone region in the bone part image obtained by extracting the bone part, the bone part image being derived by energy subtraction processing of performing weighting subtraction on the two radiation images, wherein the bone part image is derived by performing scattered ray removal processing of removing a scattered ray component of the radiation emitted to the subject, which is scattered by the subject, from the two radiation images, and performing the energy subtraction processing on the two radiation images from which the scattered ray component is removed, and wherein the scattered ray removal processing is performed by acquiring a radiation characteristic of an object interposed between the subject and a radiation detector that detects the radiation image depending on the body thickness distribution, deriving a primary ray distribution and a scattered ray distribution of the radiation included in each of the two radiation images by using the imaging condition, the body thickness distribution, and the radiation characteristic of the object, deriving an error between a sum of the primary ray distribution and the scattered ray distribution of each of the two radiation images and a pixel value at each position of the two radiation images, updating the body thickness distribution such that the error is smaller than a predetermined threshold value, repeating derivation of the radiation characteristic based on the updated body thickness distribution and derivation of the primary ray distribution and the scattered ray distribution included in each of the two radiation images, and subtracting the scattered ray distribution in a case in which the error is smaller than the predetermined threshold value from each of the two radiation images.

7. An estimation device comprising:

at least one processor, wherein the processor functions as a learned neural network that derives a result of estimation relating to a bone density of a bone part from a simple radiation image acquired by simply imaging a subject including the bone part, and the learned neural network is learned by using, as teacher data, (i) two radiation images acquired by imaging the subject including the bone part with radiation having different energy distributions, (ii) the radiation image of the subject and a bone part image representing the bone part of the subject, or (iii) the radiation image of the subject and a bone density image representing the bone density of the bone part of the subject, and information relating to the bone density of the bone part of the subject, wherein the information relating to the bone density is derived based on a body thickness distribution of the subject estimated based on at least one radiation image of the two radiation images acquired by imaging the subject including the bone part and a soft part with the radiation having different energy distributions, an imaging condition in a case in which the two radiation images are acquired, and a pixel value of a bone region in the bone part image obtained by extracting the bone part, the bone part image being derived by energy subtraction processing of performing weighting subtraction on the two radiation images, wherein the bone part image is derived by performing scattered ray removal processing of removing a scattered ray component of the radiation emitted to the subject, which is scattered by the subject, from the two radiation images, and performing the energy subtraction processing on the two radiation images from which the scattered ray component is removed, and wherein the scattered ray removal processing is performed by deriving a first primary ray distribution and a scattered ray distribution of the radiation transmitted through the subject by using the two radiation images, deriving a second primary ray distribution and a scattered ray distribution of the radiation transmitted through an object interposed between the subject and a radiation detector that detects the radiation image by using the first primary ray distribution, the scattered ray distribution, and a radiation characteristic of the object, and deriving the radiation images after transmission through the subject and the object by using the second primary ray distribution and the scattered ray distribution.

8. An estimation device comprising:
at least one processor,
wherein the processor functions as a learned neural network that derives a result of estimation relating to a bone density of a bone part from a simple radiation image acquired by simply imaging a subject including the bone part, and
the learned neural network is learned by using, as teacher data, (i) two radiation images acquired by imaging the subject including the bone part with radiation having different energy distributions, (ii) the radiation image of the subject and a bone part image representing the bone part of the subject, or (iii) the radiation image of the subject and a bone density image representing the bone density of the bone part of the subject, and information relating to the bone density of the bone part of the subject,
wherein the information relating to the bone density is derived based on a body thickness distribution of the subject estimated based on at least one radiation image of the two radiation images acquired by imaging the subject including the bone part and a soft part with the radiation having different energy distributions, an imaging condition in a case in which the two radiation images are acquired, and a pixel value of a bone region in the bone part image obtained by extracting the bone part, the bone part image being derived by energy subtraction processing of performing weighting subtraction on the two radiation images,
wherein the bone part image is derived by performing scattered ray removal processing of removing a scattered ray component of the radiation emitted to the subject, which is scattered by the subject, from the two radiation images, and performing the energy subtraction processing on the two radiation images from which the scattered ray component is removed, and
wherein the scattered ray removal processing is performed by deriving a region detection image by detecting a subject region in which the radiation is transmitted through the subject and reaches a radiation detector and a direct radiation region in which the radiation directly reaches the radiation detector without being transmitted through the subject in the two radiation images, deriving a scattered ray image relating to the scattered ray component based on the region detection image and scattered ray spread information relating to spread of a scattered ray, and subtracting the scattered ray image from the two radiation images.

9. An estimation device comprising:
at least one processor,
wherein the processor functions as a learned neural network that derives a result of estimation relating to a bone density of a bone part from a simple radiation image acquired by simply imaging a subject including the bone part, and
the learned neural network is learned by using, as teacher data, (i) two radiation images acquired by imaging the subject including the bone part with radiation having different energy distributions, (ii) the radiation image of the subject and a bone part image representing the bone part of the subject, or (iii) the radiation image of the subject and a bone density image representing the bone density of the bone part of the subject, and information relating to the bone density of the bone part of the subject,
wherein the information relating to the bone density is derived based on a body thickness distribution of the subject estimated based on at least one radiation image of the two radiation images acquired by imaging the subject including the bone part and a soft part with the radiation having different energy distributions, an imaging condition in a case in which the two radiation images are acquired, and a pixel value of a bone region in the bone part image obtained by extracting the bone part, the bone part image being derived by energy subtraction processing of performing weighting subtraction on the two radiation images, and
wherein the bone part image is obtained by deriving a processing content of first granulation suppression processing on a first radiation image having higher S/N among the two radiation images, deriving a processing content of second granulation suppression processing on a second radiation image having lower S/N based on the processing content of the first granulation suppression processing, performing granulation suppression processing on the first radiation image based on the processing content of the first granulation suppression processing, performing granulation suppression processing on the second radiation image based on the processing content of the second granulation suppression processing, and deriving the bone part image by using the two radiation images subjected to the granulation suppression processing.

10. The estimation device according to claim 9,
wherein the processing content of the first granulation suppression processing is derived based on a physical quantity map of the subject derived based on at least one of the first radiation image or the second radiation image.

11. The estimation device according to claim 1,
wherein the information relating to the bone density includes at least one of the bone density, an evaluation value of a fracture risk of the subject, or information representing a recovery state of the bone part after treatment.

12. The estimation device according to claim 1,
wherein the information relating to the bone density includes at least one of the bone density, an evaluation value of a fracture risk of the subject, or information representing a recovery state of the bone part after treatment.

13. The estimation device according to claim 3,
wherein the information relating to the bone density includes at least one of the bone density, an evaluation value of a fracture risk of the subject, or information representing a recovery state of the bone part after treatment.

14. The estimation device according to claim 6,
wherein the information relating to the bone density includes at least one of the bone density, an evaluation value of a fracture risk of the subject, or information representing a recovery state of the bone part after treatment.

15. The estimation device according to claim 7,
wherein the information relating to the bone density includes at least one of the bone density, an evaluation value of a fracture risk of the subject, or information representing a recovery state of the bone part after treatment.

16. The estimation device according to claim 8,
wherein the information relating to the bone density includes at least one of the bone density, an evaluation value of a fracture risk of the subject, or information representing a recovery state of the bone part after treatment.

17. The estimation device according to claim 9,
wherein the information relating to the bone density includes at least one of the bone density, an evaluation value of a fracture risk of the subject, or information representing a recovery state of the bone part after treatment.

\* \* \* \* \*